(12) United States Patent
Svetlov et al.

(10) Patent No.: US 8,048,638 B2
(45) Date of Patent: Nov. 1, 2011

(54) BIOMARKERS OF LIVER INJURY

(75) Inventors: Stanislav Svetlov, Gainesville, FL (US); Ronald L. Hayes, Gainesville, FL (US); Ka-Wang (Kevin) Wang, Gainesville, FL (US); Monika Oli, Gainesville, FL (US)

(73) Assignees: University of Florida Research Foundation, Inc., Gainesville, FL (US); Banyan Biomakers, Alachua, FL (US)

( * ) Notice: Subject to any disclaimer, the term of this patent is extended or adjusted under 35 U.S.C. 154(b) by 12 days.

(21) Appl. No.: 12/685,822

(22) Filed: Jan. 12, 2010

(65) Prior Publication Data

US 2010/0196942 A1 Aug. 5, 2010

Related U.S. Application Data

(63) Continuation-in-part of application No. 11/396,406, filed on Mar. 31, 2006, now Pat. No. 7,645,584.

(60) Provisional application No. 60/668,121, filed on Apr. 1, 2005.

(51) Int. Cl.
*G01N 33/53* (2006.01)
(52) U.S. Cl. ............... 435/7.1; 435/7.2; 436/518
(58) Field of Classification Search .................. None
See application file for complete search history.

(56) References Cited

U.S. PATENT DOCUMENTS

| | | | |
|---|---|---|---|
| 4,366,241 A | 12/1982 | Tom et al. |
| 4,376,110 A | 3/1983 | David et al. |
| 4,517,288 A | 5/1985 | Giegel et al. |
| 4,702,909 A | 10/1987 | Villarejos et al. |
| 4,837,168 A | 6/1989 | de Jaeger et al. |
| 5,045,694 A | 9/1991 | Beavis et al. |
| 5,118,937 A | 6/1992 | Hillenkamp et al. |
| 5,710,132 A | 1/1998 | Moller et al. |
| 5,719,060 A | 2/1998 | Hutchens et al. |
| 5,792,664 A | 8/1998 | Chait et al. |
| 6,183,977 B1 | 2/2001 | Doyle et al. |
| 6,225,047 B1 | 5/2001 | Hutchens et al. |
| 2005/0063942 A1 | 3/2005 | Clark et al. |
| 2005/0136489 A1 | 6/2005 | Tseng et al. |
| 2005/0260654 A1 | 11/2005 | Hayes et al. |
| 2005/0260697 A1 | 11/2005 | Wang et al. |
| 2007/0003982 A1 | 1/2007 | Hayes et al. |
| 2007/0027634 A1 | 2/2007 | Mendrick et al. |

FOREIGN PATENT DOCUMENTS

| | | |
|---|---|---|
| JP | 2000-505544 | 5/2000 |
| WO | WO 93/24834 | 12/1993 |
| WO | WO 99/51773 | 10/1999 |
| WO | WO 00/04389 | 1/2000 |
| WO | WO 00/56934 | 9/2000 |
| WO | WO 03/085083 | 10/2003 |

OTHER PUBLICATIONS

Kohler, G., et al. "Continuous Cultures of Fused Cells Secreting Antibody of Predefined Specificity" *Nature*, Aug. 7, 1975, pp. 495-497, vol. 256, No. 5517.
Wang, K., et al. "Proteomics Studies of Traumatic Brain Injury" *International Review of Neurobiology*, 2004, pp. 215-240; vol. 61, Elsevier, Inc.
Ward, E.S. "Binding Activities of a Repertoire of Single Immunoglobulin Variable Domains Secreted from *Escherichia coli*" *Nature*, Oct. 12, 1989, pp. 544-546, vol. 341, No. 12.
Weinberger, S., et al. "Time-of-Flight Mass Spectrometry" *Encyclopedia of Analytical Chemistry*, 2000, pp. 11915-11918, ed. R.A. Meyers, John Wiley & Sons.
Isselbacher, K. J. et al. "Biologic and Clinical Approaches to Liver Disease", *Harrison's Principles of Internal Medicine*, 1983, pp. 1301-1311, 12th Edition, McGraw-Hill, Inc.
Miura, T., et al., "An Enzymatic Method for the Assay of Serum Argininosuccinate Lyase", *Analytical Biochemistry*, 1987, pp. 482-487, vol. 164, No. 2.
Miura, T., et al., "Serum Argininosuccinate Synthetase as a Specific Marker for Liver Diseases", *Clinical Chemistry and Enzymology Communications*, 1989, pp. 153-157, vol. 1, No. 3.
Ozaki, M., et. al., "Enzyme-Linked Innunosorbent Assay of Carbamoylphosphate Synthetase I: Plasma Enzyme in Rat Experimental Hepatitis and Its Clearance", *Enzyme Protein*, 1994, pp. 213-221, vol. 48, No. 4.
Tabuchi, S., et al., "Regulation of Genes for Inducible Nitric Oxide Synthase and Urea Cycle Enzymes in Rat Liver in Endotoxin Shock", *Biochemical and Biophysical Research Communications*, 2000, pp. 221-224, vol. 268, No. 1.
Kuramitsu, Y., et al., "9.2 Proteomic Studies on Hepatitis C Virus-related Human Hepatocellular Carcinoma", *Molecular & Cellular Proteomics*, 2004, p. S115, vol. 3, No. 10.
Kim, W. et al. "Comparison of Proteome Between Hepatitis B Virus- and Hepatitis C Virus-Associated Hepatocelluar Carcinoma " *Clinical Cancer Research*, Nov. 15, 2003, pp. 5493-5500, vol. 9.
Jain, K. K. "The Role of Protein-Chip technology in molecular diagnostics" *IVD Technology*, Jul./Aug. 2002, pp. 1-5.

*Primary Examiner* — Jacob Cheu
(74) *Attorney, Agent, or Firm* — Saliwanchik, Lloyd & Eisenschenk

(57) ABSTRACT

Novel, sensitive and specific markers for diagnostics and monitoring of liver injuries, including, but not limited to ischemic liver damage, are provided. This includes identification of several enzymes of arginine/urea/nitric oxide cycle, sulfuration enzymes and spectrin breakdown related products, among others.

19 Claims, 35 Drawing Sheets

LIVER TISSUE

Alpha-spectrin

ASS gammaGTP

ASS in rat plasma

Predicted molecular weight – 46 kDa

Experiment 1: ECL staining

Experiment 2: Alkaline phosphatase Staining (color)

Alc- chronic alcohol treatment rats
I/R- liver ischemia/reperfusion
S-sham operatated rats, no vena portae ligation
Control- intact rats
M- molecular weight markers Reperfusion time-course of ASS in rat plasma in serum after 30 min of ischemia.

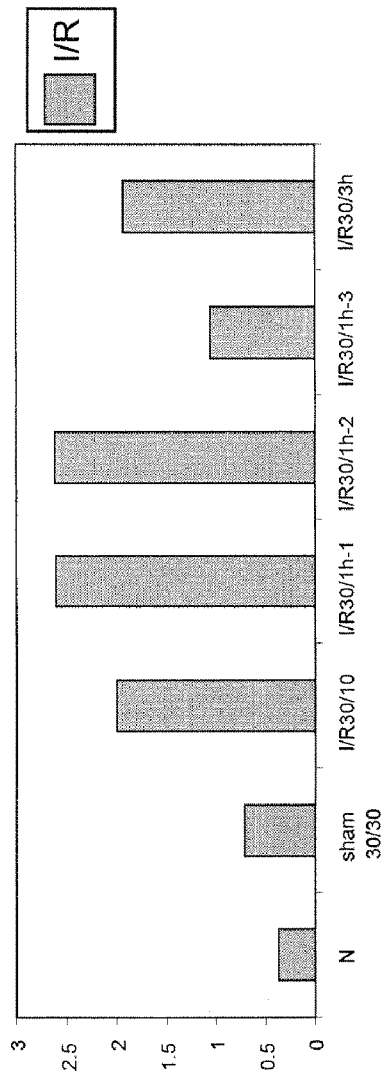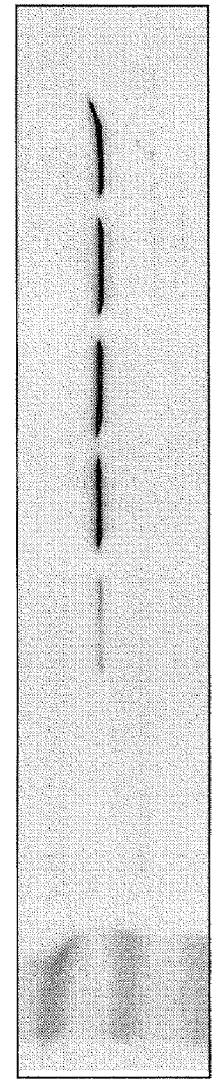
FIGURE 23A
FIGURE 23B

| No | sample | OD | predicted value(ng) |
|---|---|---|---|
| 1 | S3A | 0.5398 | 33.3 |
| 2 | S3B | 0.2858 | 11.5 |
| 3 | S3m1 | 2.1513 | >100 |
| 4 | S30 | 2.2721 | >100 |
| 5 | S60 | 2.2711 | >100 |
| 6 | S4A | 0.5796 | 35.6 |
| 7 | S4B | 0.4339 | 23.6 |
| 8 | S430 | 2.7562 | 150 |
| 9 | S460 | 2.8713 | 150 |
| 10 | HSTAB mio1 | 0.9153 | 63.1 |
| 11 | HS1BS1 | 0.5582 | 33.8 |
| 12 | HS 3m1 | 1.5022 | 111.3 |
| 13 | HS1 30min1 | 2.1874 | >100 |
| 14 | HS1 60min1 | 2.2189 | >100 |
| 15 | HS1 120min1 | 2.4606 | >100 |
| 16 | HS2 Ahe PI | 0.9717 | 67.8 |
| 17 | HS2 BS2 | 0.8652 | 59 |
| 18 | HS2 3m1 | 0.92 | 63.5 |
| 19 | HS2 60min | 1.465 | 108.2 |
| 20 | HS2 120min1 | 1.5942 | 118.2 |
| 21 | P3 60 | 1.4534 | 107.3 |
| 22 | P4 30 | 1.2797 | 93 |
| 23 | P4 60 | 1.5434 | 114.7 |
| 24 | S2 control | 0.156 | 0.82 |
| 25 | S2 45 | 0.1602 | 1.16 |
| 26 | S1 15 | 0.1876 | 3.4 |
| 27 | S1 45 | 0.1956 | 4.1 |
| 28 | S1 6h | 1.3353 | 97.6 |
| 29 | S3 1h | 0.195 | 4 |

SEQUENCE LISTING

```
<160> NUMBER OF SEQ ID NOS: 2

<210> SEQ ID NO 1
<211> LENGTH: 13
<212> TYPE: PRT
<213> ORGANISM: Homo sapiens

<400> SEQUENCE: 1

Ala Arg Lys Lys Ala Leu Lys Leu Gly Ala Lys Lys Val
1               5                   10

<210> SEQ ID NO 2
<211> LENGTH: 16
<212> TYPE: PRT
<213> ORGANISM: Homo sapiens

<400> SEQUENCE: 2

Ala Lys Ala Pro Asn Thr Pro Asp Ile Leu Glu Ile Glu Phe Lys Lys
1               5                   10                  15
```

BIOMARKERS OF LIVER INJURY

CROSS REFERENCE TO RELATED APPLICATIONS

The present application is a continuation-in-part of U.S. Ser. No. 11/396,406, filed Mar. 31, 2006, now U.S. Pat. No. 7,645,584, which claims the benefit of U.S. provisional Ser. No. 60/668,121, filed Apr. 1, 2005. The foregoing is incorporated herein by reference in its entirety.

This invention was made with government support under National Institutes of Health, NIDDK grant number DK 061649 and U.S. Army Medical Research & Material Command/DoD, grant number DAMD17-03-1-0066. The government has certain rights in the invention.

FIELD OF THE INVENTION

The invention relates to a panel of biomarkers and methods for diagnosis of liver injury. In particular, sensitive, specific and reliable detection and identification of biomarkers that are uniquely produced in liver injury are provided.

BACKGROUND

The liver is an extremely important organ. As the major metabolic organ of the body, the liver plays some role in almost every biochemical process, including the deamination of amino acids and the formation of urea, the regulation of blood sugar through the formation of glycogen, the production of plasma proteins, the production and secretion of bile, phagocytosis of particulate matter from the splachnic (intestinal) circulation, and the detoxification and elimination of both endogenous and exogenous toxins.

The many functions of the liver depend on its intimate association with circulating blood. Each liver cell is exposed on at least one face to a blood sinusoid which contains oxygenated arterial blood mixed with venous blood from the splachnic circulation. This profuse blood supply is necessary for the liver to function. The blood from the sinusoids supplies the hepatocytes with oxygen and nutrients. The hepatocytes use the nutrients both for their own metabolic needs and for the synthesis of the liver's many essential products. Abnormalities in the blood or vasculature can have immediate and severe effects on the liver. For example, liver cells are exposed to high concentrations of any toxic compounds that are ingested orally, such as ethyl alcohol. Even when the ingested compound is not itself toxic, intermediate derivatives produced during hepatic metabolism of the compound may damage the hepatocytes. This phenomenon occurs, for example, in carbon tetrachloride poisoning. Since the blood moves slowly through hepatic sinusoids, liver cells are also quite vulnerable to blood-borne infectious agents such as viruses and bacteria. Furthermore, derangements in hepatic blood pressure can damage liver tissue. Right-sided cardiac failure increases hepatic blood pressure and can lead to pressure necrosis (hepatocellular death) and fibrosis. Left-sided cardiac failure can reduce hepatic perfusion and lead to hepatocellular anoxia and death.

Liver damage from any source may result in liver regeneration, necrosis (cell death), degeneration, inflammation, fibrosis, or mixtures of these processes, depending on the type and extent of injury and its location within the liver. The liver has great functional reserves, but with progressive injury, disruption of liver function can have life-threatening consequences. Cirrhosis, which is a type of end-stage liver disease, is one of the top ten causes of death in the Western world.

There are a few markers of liver injury (e.g. ALT, LDH), which have been used for diagnostics or monitoring of clinical conditions where liver injury, such as, ischemia/reperfusion is a major pathogenic cause of liver damage. These conditions are traumatic and thermal injury, abdominal surgery, hemorrhagic and septic shock, abdominal gunshot wounds, and liver transplantation. However, ALT, LDH and other classic markers are either not sensitive or not specific.

There is thus a need in the art for specific, sensitive and reliable detection of biomarkers that are diagnostic of liver injury and disease.

SUMMARY

Novel, sensitive and specific markers for diagnostics and monitoring of multiple liver ischemia-induced injury are provided. In particular, identification of biomarkers is based on identification of several enzymes of arginine/urea/nitric oxide cycle, sulfuration enzymes and spectrin breakdown related products. These include, but not limited to argininosuccinate synthetase (ASS) and argininosuccinate lyase (ASL), sulfuration (estrogen sulfotransferase (EST), squalene synthase (SQS), liver glycogen phosphorylase (GP), carbamoyl-phosphate synthetase (CPS-1), a-enolase 1 and glucose-regulating protein (GRP).

In a preferred embodiment, a composition comprises enzymes of arginine/urea/nitric oxide cycle, sulfuration enzymes and spectrin breakdown related products.

In another preferred embodiment, the composition comprises argininosuccinate synthetase (ASS) and argininosuccinate lyase (ASL), sulfuration (estrogen sulfotransferase (EST), squalene synthase (SQS), liver glycogen phosphorylase (GP), carbamoyl-phosphate synthetase (CPS-1), a-enolase 1, glucose-regulated protein (GRP) and spectrin breakdown products.

In another preferred embodiment, a method of detecting liver ischemic injury comprises detection of one or more enzymes of the arginine, urea and/or nitric oxide cycle.

In another preferred embodiment, a method of detecting liver ischemic injury comprises detection of at least one marker of liver injury comprising: argininosuccinate synthetase (ASS) and argininosuccinate lyase (ASL), sulfuration (estrogen sulfotransferase (EST), squalene synthase (SQS), liver glycogen phosphorylase (GP), carbamoyl-phosphate synthetase (CPS-1), a-enolase 1, glucose-regulated protein (GRP) and spectrin breakdown products.

In another preferred embodiment, kits for detection of liver injury are provided. Preferably, the kits provide a composition of biomarkers comprising at least one of the following markers: argininosuccinate synthetase (ASS) and argininosuccinate lyase (ASL), sulfuration (estrogen sulfotransferase (EST), squalene synthase (SQS), liver glycogen phosphorylase (GP), carbamoyl-phosphate synthetase (CPS-1), a-enolase 1, glucose-regulated protein (GRP) and spectrin breakdown products.

In another preferred embodiment, liver damage of any origin can be diagnosed and monitored by detection of one or more biomarkers disclosed herein and in conjunction with other known tests such as assessment of hepatic blood flow or prothrombin clotting time, or serum markers, such as serum bilirubin, serum transaminase, and serum alkaline phosphatase levels. The level of biomarkers detected can be correlated with histological evaluation of liver tissue, which is helpful in determining the type and extent of liver damage; in vitro biochemical tests measuring liver function or serum markers and/or results from liver tissue biopsy. If desired, detection of the biomarkers can be combined with biochemical tests, tissue biopsy, patient medical history, and assessment of means inducing liver damage is used in determining the extent of liver damage.

In another preferred embodiment, therapeutic strategies are directed to targeting of argininosuccinate synthetase (ASS) and argininosuccinate lyase (ASL), sulfuration (estrogen sulfotransferase (EST).

In another preferred embodiment, absence of ASS is diagnostic of liver enzyme diseases. For example, lack of ASS (Argininosuccinate Synthetase Deficiency) is a genetic disease: Maple Syrup Urine Disease (MSUD) and Citrullinemia. Baseline levels in healthy controls are detectable with the methods of the invention and would expect to see below normal values in humans affected by the condition.

In a preferred embodiment, a method of detecting and diagnosing liver enzyme disorders comprises determining absence of at least one or more biomarkers in a subject sample, and; correlating the detection or absence thereof, of one or more biomarkers with a diagnosis of liver enzyme disorders, wherein the correlation takes into account the detection, or absence thereof, of one or more biomarkers in each diagnosis, as compared to normal subjects wherein the one or more protein markers are selected from: argininosuccinate synthetase (ASS), argininosuccinate lyase (ASL), sulfuration (estrogen sulfotransferase (EST), squalene synthase (SQS), liver glycogen phosphorylase (GP), carbamoyl-phosphate synthetase (CPS-1), α-enolase 1, glucose-regulated protein (GRP) and spectrin breakdown products, and; correlating the detection of one or more protein biomarkers with a diagnosis of liver enzyme disorders, wherein the correlation takes into account the absence of detection of one or more protein biomarkers in each diagnosis, as compared to normal subjects.

In another preferred embodiment, a method of detecting patients at risk of developing liver enzyme disorders comprises determining absence of at least one or more biomarkers in a subject sample, and; correlating the detection or absence thereof, of one or more biomarkers with a diagnosis of patients at-risk of developing liver enzyme disorders, wherein the correlation takes into account the detection, or absence thereof, of one or more biomarker in each diagnosis, as compared to normal subjects wherein the one or more protein markers are selected from: argininosuccinate synthetase (ASS), argininosuccinate lyase (ASL), sulfuration (estrogen sulfotransferase (EST), squalene synthase (SQS), liver glycogen phosphorylase (GP), carbamoyl-phosphate synthetase (CPS-1), a-enolase 1, glucose-regulated protein (GRP) and spectrin breakdown products, and; correlating the detection or absence thereof, of one or more protein biomarkers with a diagnosis of at-risk liver enzyme disorder patients, wherein the correlation takes into account the absence of detection of one or more protein biomarkers in each diagnosis, as compared to normal subjects.

In another preferred embodiment, liver damage or injury can be detected shortly after exposure to various liver toxins, including chlorinated hydrocarbons such as chloroform, trichloroethylene, chlorofoim and the like. A significant marker of injury, ASS, is detectable as early as 1 hr after exposure, indicative of liver injury. Hepatic injury due to drugs, such as Ecstasy (MDMA), can be detected shortly after exposure at certain levels. Other drugs such as psychotropic agents and acetaminophen are also known to affect the liver and ASS is expected to be an early marker of injury due to these classes of drugs. After repeated intake of ecstasy, significant increases in ASS, SULT2A1 and CPS-1 are detected and can be used to detect onset of liver injury.

ASS levels increase almost immediately after exposure to a bacterial endotoxin such as LPS, providing a rapid indication of liver injury and a basis for initiating intervention. ALT and AST do not measurably increase after exposure to LPS and therefore are not good candidates for early establishment of bacterial hepatotoxicity. On the other hand, in the presence of a liver priming agent such as D-galactosamine, LPS induces significantly increased levels of ASS and ALT in serum.

Other aspects of the invention are described infra.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

FIG. 3A shows detection of a-spectrin. FIG. 3B shows detection of argininosuccinate synthetase (ASS).

FIG. 11A shows the control rat livers; FIG. 11B shows rat livers subjected to 30 min of normothermic ischemia followed by 30 min reperfusion (I/R, 30/30); FIGS. 11 C and 11D show control rat livers treated with recombinant caspase-3 (FIG. 11C), or calpain-2 (FIG. 11D) in vitro. Representative blot from 2 runs of identical samples is shown. Red squares depict proteins up- or down regulated in I/R, caspase-3 and calpain-2 treated livers vs. control. The numbers indicate the lane numbers on the blot. Lanes marked: #2-Nitric Oxide Synthase (nNOS); #8-arginase-I; #9-Squalene Synthase (SQS); #12-β-catenin; #13-α-actinin; #16-MEK5; #27-ASS; #31-Ninjurin.

FIG. 16A: accumulation of αII-spectrin breakdown products in I/R livers similar to caspase-3 (120 kDa) and calpain-2 (145 kDa) dependent cleavage fragments; FIG. 16B: appearance of caspase-3-dependent ASS cleavage fragments within 10 min after reperfusion; FIGS. 16C and 16D: hepatic levels of arginase-I and EST-1 after 10 and 30 min of reperfusion. Representative Western blot images from 3 different caspase-3 and calpain-2 treatments of pooled intact liver tissues (FIG. 16A) and from 4 experimental rats in each group of I/R injury are shown.

FIG. 18A—Blood was withdrawn from rat heart after 30 min of ischemia followed by 30 of reperfusion and from chronic alcoholic rats as described in Experimental Procedures. FIG. 18B—Rats were treated with LPS/D-galactosamine or saline as described in Materials and Methods. Serum or plasma was collected and equal volumes (10 μl) were processed as described in Materials and Methods in detail. Proteins were separated by SDS-PAGE and immunoblotted with antibody against ASS, EST-1 or alanine aminotransferase ALT. Membranes were developed by ECL, and images were scanned. Representative blots out from 4 or 5 performed using at least 3 different experiments are shown (FIG. 18A). N-intact, naïve rats (N1, N2), S-sham operated rats (S1, S2); I/R-30 min ischemia followed by 30 min reperfusion rats (I/R1, I/R2); A1, A2 and A3—chronic alcoholic rats (n=3). Representative blot out from 3 performed is shown for LPS/D-Gal treatment using 3 rats for each time point; I/R sample (30/30) was included for comparison (FIG. 18B).

FIG. 23A-23B show the results of rat I/R serum samples probed with ASS2 antibody. FIG. 23A is a graph showing the results from a sandwich ELISA (SW-ELISA). The capture antibody is ASS2 rabbit; detection antibody is ASS2 mouse (BD-biotrasduction). The assay was conducted in a 384 well plate, in a volume of 20 μl/well. FIG. 23 is a Western Immunoblot. The reaction was carried out at in a volume of 5 μl/well and probed with ASS2 anti-rabbit antibody (1:1000).

DETAILED DESCRIPTION

Figure 1:
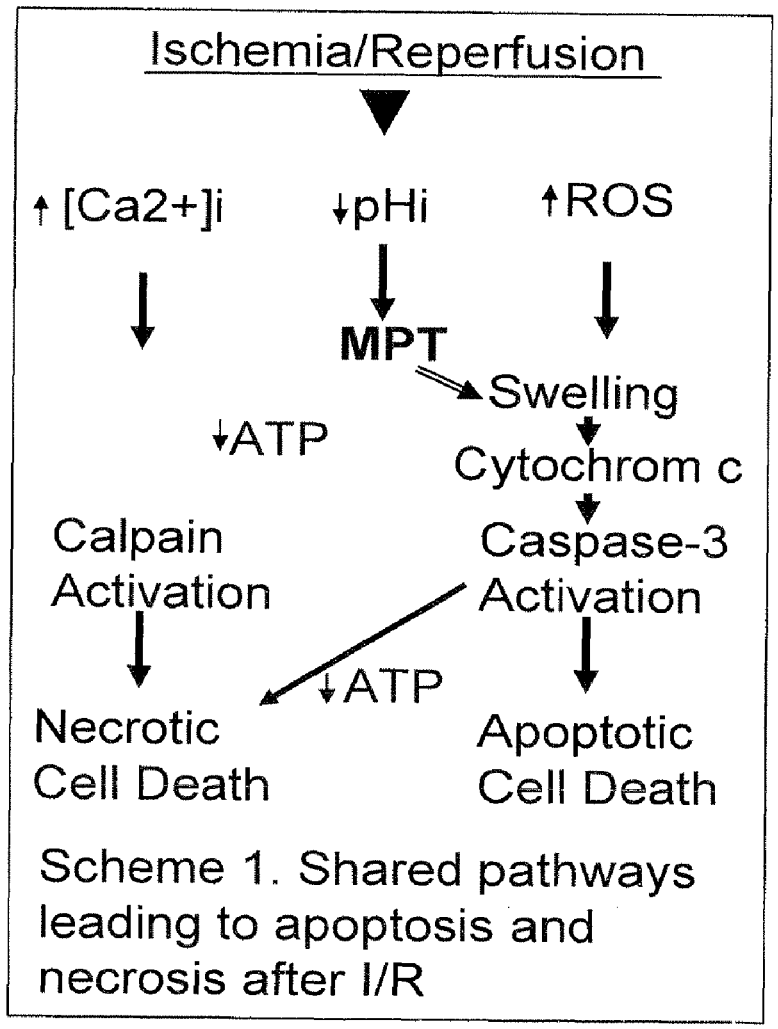
FIG. 1 is a schematic illustration of the pathways leading to apoptosis and necrosis after ischemia/reperfusion.
Figure 2:
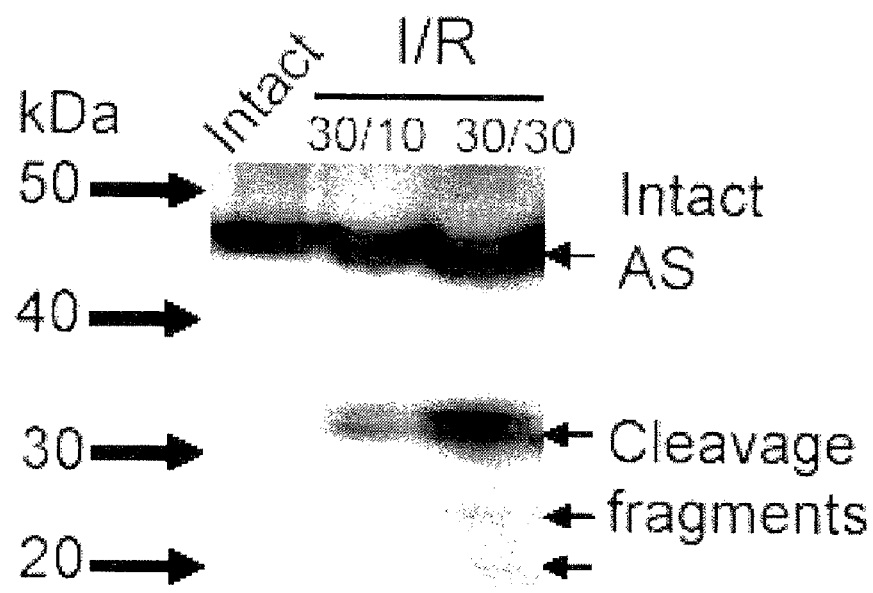
FIG. 2 is a blot showing expression of ASS and its cleavage fragments in normal and I/R liver. 30/10-30 min. ischemia, 10 min reperfusion; 30/30-30 min ischemia, 30 min reperfusion.

A panel of sensitive and specific biomarkers diagnostic of liver injury are provided. In particular, ASS, ASL, SQS and EST are shown to be pathogenically relevant biomarkers of liver ischemia/reperfusion-induced injury. In these studies, liver proteomic approach for initial discovery of novel biomarkers of liver ischemia/reperfusion injury was employed. ASS, ASL, SQS and EST appear in plasma and serum in a very early stage of experimental ischemia/reperfusion-induced liver injury, and therefore have a high diagnostic and prognostic value, including the monitoring of liver transplantation.

Definitions

Prior to setting forth the invention, it may be helpful to an understanding thereof to set forth definitions of certain terms that are used hereinafter.

The phrase "liver injury" is used herein in the broadest sense, and indicates any structural or functional liver injury resulting, directly or indirectly, from internal or external factors or their combinations. Liver injury can be induced by a number of factors including, but not limited to, ischemia, exposure to hepatotoxic compounds, radiation exposure, mechanical liver injuries, genetic predisposition, viral infections, alcohol and drug abuse, autoimmune disease, such as, autoimmune chronic hepatitis and as a result of elevated in vivo levels of proteins, such as activin and TGF-β. The tell "liver injury" includes rejection of a transplanted liver.

The term "prevention" as used in the context of the present invention includes the complete or partial blocking of the occurrence of anticipated liver damage and the interception or moderation of the progress of liver damage already occurred. Whereas it is foreseen that existing liver damage may be completely or partially reversed, this is not a requirement under this definition.

The term "preventatively effective amount" is used to designate an amount effective in achieving prevention as hereinabove defined.

Patients "at risk of developing liver damage" include those patients who are anticipated to be exposed to or who have been exposed to any factor known to have the potential of inducing liver damage. This includes exposure to hepatotoxic compounds (whether as part of a therapy or due to accidental exposure), in doses conventionally considered safe or in doses conventionally considered unsafe, radiation, or any clinical therapy useful in the treatment of a disease, wherein said clinical therapy is known to induce liver damage. The definition further includes actual or potential sustained liver injury through physical trauma including, blunt trauma, gunshot wounds, or surgery. Patients at risk of developing liver damage include those patients having inborn errors of metabolism and who are genetically predisposed to induction of liver damage, or those mammalian patients susceptible to liver damage due to other risk factors including genetic factors, age, sex, nutritional status, exposure to other drugs, and systemic diseases. Patients at risk of developing liver damage also includes those patients who are anticipated to be exposed to or who have been exposed to viruses such as hepatitis A, B, C, D, or E, or autoimmune chronic hepatitis.

"Ischemia" occurs when the supply of oxygenated blood to a tissue is reduced or interrupted.

"Marker" or "biomarker" are used interchangeably herein, and in the context of the present invention refers to a polypeptide (of a particular apparent molecular weight) which is differentially present in a sample taken from patients having liver injury and/or liver disorders as compared to a comparable sample taken from control subjects (e.g., a person with a negative diagnosis, normal or healthy subject).

"Activity" of an enzyme is the amount of product produced per unit time at a fixed temperature and pH.

"Specific activity" of an enzyme is the amount of product produced per unit time per mg protein.

"Substrate" is the target protein that the enzyme catalyzes. The International Union of Biochemistry (I.U.B.) initiated standards of enzyme nomenclature which recommend that enzyme names indicate both the substrate acted upon and the type of reaction catalyzed.

"Complementary" in the context of the present invention refers to detection of at least two biomarkers, which when detected together provides increased sensitivity and specificity as compared to detection of one biomarker alone.

The phrase "differentially present" refers to differences in the quantity and/or the frequency of a marker present in a sample taken from patients having for example, liver injury as compared to a control subject. For example, a marker can be a polypeptide which is present at an elevated level or at a decreased level in samples of patients with liver injury compared to samples of control subjects. Alternatively, a marker can be a polypeptide which is detected at a higher frequency or at a lower frequency in samples of patients compared to samples of control subjects. A marker can be differentially present in terms of quantity, frequency or both.

A polypeptide is differentially present between the two samples if the amount of the polypeptide in one sample is statistically significantly different from the amount of the polypeptide in the other sample. For example, a polypeptide is differentially present between the two samples if it is present at least about 120%, at least about 130%, at least about 150%, at least about 180%, at least about 200%, at least about 300%, at least about 500%, at least about 700%, at least about 900%, or at least about 1000% greater than it is present in the other sample, or if it is detectable in one sample and not detectable in the other.

Alternatively or additionally, a polypeptide is differentially present between the two sets of samples if the frequency of detecting the polypeptide in samples of patients' suffering from liver injury and/or liver disorders is statistically significantly higher or lower than in the control samples. For example, a polypeptide is differentially present between the two sets of samples if it is detected at least about 120%, at least about 130%, at least about 150%, at least about 80%, at least about 200%, at least about 300%, at least about 500%, at least about 700%, at least about 900%, or at least about 1000% more frequently or less frequently observed in one set of samples than the other set of samples.

"Diagnostic" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

A "test amount" of a marker refers to an amount of a marker present in a sample being tested. A test amount can be either in absolute amount (e.g., µg/ml) or a relative amount (e.g., relative intensity of signals).

A "diagnostic amount" of a marker refers to an amount of a marker in a subject's sample that is consistent with a diagnosis of liver injury and/or liver disorder. A diagnostic amount can be either in absolute amount (e.g., µg/ml) or a relative amount (e.g., relative intensity of signals).

A "control amount" of a marker can be any amount or a range of amount which is to be compared against a test amount of a marker. For example, a control amount of a marker can be the amount of a marker in a person without liver injury and/or liver disorder. A control amount can be either in absolute amount (e.g., µg/ml) or a relative amount (e.g., relative intensity of signals).

"Probe" refers to a device that is removably insertable into a gas phase ion spectrometer and comprises a substrate having a surface for presenting a marker for detection. A probe can comprise a single substrate or a plurality of substrates.

"Substrate" or "probe substrate" refers to a solid phase onto which an adsorbent can be provided (e.g., by attachment, deposition, etc.).

"Adsorbent" refers to any material capable of adsorbing a marker. The term "adsorbent" is used herein to refer both to a single material ("monoplex adsorbent") (e.g., a compound or functional group) to which the marker is exposed, and to a plurality of different materials ("multiplex adsorbent") to which the marker is exposed. The adsorbent materials in a multiplex adsorbent are referred to as "adsorbent species." For example, an addressable location on a probe substrate can comprise a multiplex adsorbent characterized by many different adsorbent species (e.g., anion exchange materials, metal chelators, or antibodies), having different binding characteristics. Substrate material itself can also contribute to adsorbing a marker and may be considered part of an "adsorbent."

"Adsorption" or "retention" refers to the detectable binding between an absorbent and a marker either before or after washing with an eluant (selectivity threshold modifier) or a washing solution.

"Eluant" or "washing solution" refers to an agent that can be used to mediate adsorption of a marker to an adsorbent. Eluants and washing solutions are also referred to as "selectivity threshold modifiers." Eluants and washing solutions can be used to wash and remove unbound materials from the probe substrate surface.

"Resolve," "resolution," or "resolution of marker" refers to the detection of at least one marker in a sample. Resolution includes the detection of a plurality of markers in a sample by separation and subsequent differential detection. Resolution does not require the complete separation of one or more markers from all other biomolecules in a mixture. Rather, any separation that allows the distinction between at least one marker and other biomolecules suffices.

"Gas phase ion spectrometer" refers to an apparatus that measures a parameter which can be translated into mass-to-charge ratios of ions formed when a sample is volatilized and ionized. Generally ions of interest bear a single charge, and mass-to-charge ratios are often simply referred to as mass. Gas phase ion spectrometers include, for example, mass spectrometers, ion mobility spectrometers, and total ion current measuring devices.

"Mass spectrometer" refers to a gas phase ion spectrometer that includes an inlet system, an ionization source, an ion optic assembly, a mass analyzer, and a detector.

"Laser desorption mass spectrometer" refers to a mass spectrometer which uses laser as means to desorb, volatilize, and ionize an analyte.

"Detect" refers to identifying the presence, absence or amount of the object to be detected.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

"Detectable moiety" or a "label" refers to a composition detectable by spectroscopic, photochemical, biochemical, immunochemical, or chemical means. For example, useful labels include $^{32}$P, $^{35}$S, fluorescent dyes, electron-dense reagents, enzymes (e.g., as commonly used in an ELISA), biotin-streptavidin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantify the amount of bound detectable moiety in a sample. Quantitation of the signal is achieved by, e.g., scintillation counting, densitometry, or flow cytometry.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'$_2$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, $CH_1$, $CH_2$ and $CH_3$, but does not include the heavy chain variable region.

"Immunoassay" is an assay that uses an antibody to specifically bind an antigen (e.g., a marker). The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to marker argininosuccinate synthetase (ASS) from specific species such as rat, mouse, or human can be selected to obtain only those polyclonal antibodies that are specifically immunoreactive with marker ASS and not with other proteins, except for polymorphic variants and alleles of marker ASS. This selection may be achieved by subtracting out antibodies that cross-react with marker ASS molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction is at least twice background signal or noise and more typically more than 10 to 100 times background.

"Energy absorbing molecule" or "EAM" refers to a molecule that absorbs energy from an ionization source in a mass spectrometer thereby aiding desorption of analyte, such as a marker, from a probe surface. Depending on the size and nature of the analyte, the energy absorbing molecule can be optionally used. Energy absorbing molecules used in MALDI are frequently referred to as "matrix." Cinnamic acid derivatives, sinapinic acid ("SPA"), cyano hydroxy cinnamic acid ("CHCA") and dihydroxybenzoic acid are frequently used as energy absorbing molecules in laser desorption of bioorganic molecules.

"Sample" is used herein in its broadest sense. A sample comprising polynucleotides, polypeptides, peptides, antibodies fragments and derivatives thereof. may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; fragments and derivatives thereof.

"Substantially purified" refers to nucleic acid molecules or proteins that are removed from their natural environment and are isolated or separated, and are at least about 60% free, preferably about 75% free, and most preferably about 90% free, from other components with which they are naturally associated.

"Substrate" refers to any rigid or semi-rigid support to which nucleic acid molecules or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

As used herein, the term "fragment or segment", as applied to a nucleic acid sequence, gene or polypeptide, will ordinarily be at least about 5 contiguous nucleic acid bases (for nucleic acid sequence or gene) or amino acids (for polypeptides), typically at least about 10 contiguous nucleic acid bases or amino acids, more typically at least about 20 contiguous nucleic acid bases or amino acids, usually at least about 30 contiguous nucleic acid bases or amino acids, preferably at least about 40 contiguous nucleic acid bases or amino acids, more preferably at least about 50 contiguous nucleic acid bases or amino acids, and even more preferably at least about 60 to 80 or more contiguous nucleic acid bases or amino acids in length. "Overlapping fragments" as used herein, refer to contiguous nucleic acid or peptide fragments which begin at the amino terminal end of a nucleic acid or protein and end at the carboxy terminal end of the nucleic acid or protein. Each nucleic acid or peptide fragment has at least about one contiguous nucleic acid or amino acid position in common with the next nucleic acid or peptide fragment, more preferably at least about three contiguous nucleic acid bases or amino acid positions in common, most preferably at least about ten contiguous nucleic acid bases amino acid positions in common.

A significant "fragment" in a nucleic acid context is a contiguous segment of at least about 17 nucleotides, generally at least 20 nucleotides, more generally at least 23 nucleotides, ordinarily at least 26 nucleotides, more ordinarily at least 29 nucleotides, often at least 32 nucleotides, more often at least 35 nucleotides, typically at least 38 nucleotides, more typically at least 41 nucleotides, usually at least 44 nucleotides, more usually at least 47 nucleotides, preferably at least 50 nucleotides, more preferably at least 53 nucleotides, and in particularly preferred embodiments is at least 56 or more nucleotides.

As used herein, the terms "polypeptide" or "peptide" encompasses amino acid chains of any length, including full length proteins recited herein.

As used herein, "peptides or epitopes with longer amino sequences" encompasses amino acid chains of any length, including full length proteins recited herein.

As used herein, "variant" or "derivative" of polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, LASERGENE software (DNASTAR).

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) or single base mutations in which the polynucleotide sequence varies by one base.

"Stringency" is meant the combination of conditions to which nucleic acids are subject that cause the duplex to dissociate, such as temperature, ionic strength, and concentration of additives such as formamide. Conditions that are more likely to cause the duplex to dissociate are called "higher stringency", e.g. higher temperature, lower ionic strength and higher concentration of formamide.

For applications requiring high selectivity, one will typically desire to employ relatively stringent conditions to form the hybrids, e.g., one will select relatively low salt and/or high temperature conditions, such as provided by about 0.02 M to about 0.10 M NaCl at temperatures of about 50° C. to about 70° C.

For certain applications, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated depending on the desired results.

The phrase "hybridizing conditions" and its grammatical equivalents, when used with a maintenance time period, indicates subjecting the hybridization reaction admixture, in context of the concentration of the reactants and accompanying reagents in the admixture, to time, temperature, pH conditions sufficient to allow the polynucleotide probe to anneal with the target sequence, typically to form the nucleic acid duplex. Such time, temperature and pH conditions required to accomplish the hybridization depend, as is well known in the art on the length of the polynucleotide probe to be hybridized, the degree of complementarity between the polynucleotide probe and the target, the guanidine and cytosine content of the polynucleotide, the stringency of the hybridization desired, and the presence of salts or additional reagents in the hybridization reaction admixture as may affect the kinetics of hybridization. Methods for optimizing hybridization conditions for a given hybridization reaction admixture are well known in the art.

Liver Biomarkers

In a preferred embodiment, detection of one or more enzymes of arginine/urea/nitric oxide cycle, sulfuration enzymes and spectrin breakdown related products is diagnostic of liver injury. Examples of these markers include, but not limited to: argininosuccinate synthetase (ASS) and argininosuccinate lyase (ASL), sulfuration, estrogen sullotransferase (EST), squalene synthase (SQS), liver glycogen phosphorylase (GP), carbamoyl-phosphate synthetase (CPS-1), α-enolase 1, glucose-regulated protein (GRP) and spectrin breakdown products.

In another preferred embodiment, detection of one or more biomarkers can be correlated to known diagnostic tests of liver injury. Examples include: liver function tests—assessment of hepatic clearance of organic anions, such as, bilirubin, indocyanine green sulfobromophthalein (BSP) and bile acids; assessment of hepatic blood flow by measurements of galactose and ICG clearance; and assessment of hepatic microsomal function, through the use of the aminopyrine breath test and caffeine clearance test.

In a preferred embodiment, detection of the biomarkers is diagnostic of liver injury. Liver injury is a result of any factors. For example, liver ischemic injury; liver damage induced by hepatotoxic compounds including direct cytotoxicity including drug hypersensitivity reactions, cholestasis, and injury to the vascular endothelium (Sinclair et al., Textbook of Internal Medicine, 569-575 (1992) (editor, Kelley; Publisher, J. B. Lippincott Co.).

A number of hepatotoxic compounds, including certain therapeutics, induce cytotoxicity. Hepatotoxic compounds can produce liver cytotoxicity by direct chemical attack or by the production of a toxic metabolite. Although the exact mechanism of hepatotoxicity is uncertain, the products of reductive metabolism are highly reactive species that bind to cellular macromolecules and cause lipid peroxidation and inactivation of drug metabolizing and other enzymes. The membrane injury provokes release of calcium from mitochondria and smooth endoplasmic reticulum and appears to interfere with the calcium ion pump, which normally prevents cytosolic accumulation of calcium. The deleterious effect on cell metabolism with resultant calcium accumulation, the loss of potassium and enzymes from the cytoplasm, and the loss of essential energy that results from mitochondrial injury all contribute to the necrosis of hepatic tissue.

Many hepatotoxic compounds unpredictably produce liver damage in a small proportion of recipients. In some patients, the liver damage is referred to as a hypersensitivity reaction and is like that of a drug reaction, where the patient presents with fever, rash and eosinophilia and has a recurrence of symptoms upon rechallenge of the drug. In other situations, the mechanism for injury is unknown and may represent aberrant metabolism in susceptible patients that permits the production or accumulation of hepatotoxic metabolites.

Those drug inducing cytotoxicity by direct chemical attack include the following: Anesthetics, such as, Enflurane, Fluoroxene, Halothane, and Methoxyflurane; Neuropsychotropics, such as, Cocaine, Hydrazides, Methylphenidate, and Tricyclics; Anticonvulsants, such as, Phenyloin and Valproic acid; Analgesics, such as, Acetaminophen, Chlorzoxazone, Dantrolene, Diclofenac, Ibuprofen, Indomethacin, Salicylates, Tolmetin, and Zoxazolamine; Hormones, such as, Acetohexamide, Carbutamide, Glipizide, Metahexamide, Propylthiouracil, Tamoxifen, Diethylstilbestrol; Antimicrobials, such as, Amphotericin B, Clindamycin, Ketoconazole, Mebendazole, Metronidazole, Oxacillin, Paraminosalicylic acid, Penicillin, Rifampicin, Sulfonamides, Tetracycline, and Zidovudine; Cardiovascular drugs, such as, Amiodarone, Dilitiazem, a-Methyldopa, Mexiletine, Hydrazaline, Nicotinic acid, Papaverine, Perhexyline, Procainamide, Quinidine, and Tocainamide; and Immunosuppressives and Antineoplastics, such as, Asparaginase, Cisplatin, Cyclophosphamide, Dacarbazine, Doxorubicin, Fluorouracil, Methotrexate, Mithramycin, 6-MP, Nitrosoureas, Tamoxifen, Thioguanine, and Vincristine; and Miscellaneous drugs, such as, Disulfuram, Iodide ion, Oxyphenisatin, Vitamin A and Paraminobenzoic acid.

Those hepatotoxic compounds producing hypersensitivity reaction in the liver include the following: Phenyloin, Paramino salicylic acid, Chlorpromazine, Sulfonamides, Erythromycin estolate, Isoniazid, Halothane, Methyldopa, and Valproic acid.

Hepatotoxic compounds inducing cholestasis, an arrest in the flow of bile, may take several forms. Centribular cholestasis is accompanied by portal inflammatory changes. Bile duct changes have been reported with some drugs such as erythromycin, while pure canalicular cholestasis is characteristic of other drugs such as the anabolic steroids. Chronic cholestasis has been linked to such drugs as methyltestosterone and estradiol.

Those hepatotoxic compounds inducing cholestatic disease include the following: Contraceptive steroids, androgenic steroids, anabolic steroids, Acetylsalicylic acid, Azathioprine, Benzodiazepine, Chenodeoxycholic acid, Chlordiazepoxide, Erythromycin estolate, Fluphenazine, Furosemide, Griseofulvin, Haloperidol, Imipramine, 6-Mercaptopurine, Methimazole, Methotrexate, Methyldopa, Methylenediamine, Methyltestosterone, Naproxen, Nitrofurantoin, Penicillamine, Perphenazine, Prochlorperazine, Promazine, Thiobendazole, Thioridazine, Tolbutamide, Trim ethoprimsulfamethoxazole, Arsenic, Copper, and Paraquat.

Some drugs, although primarily cholestatic, can also produce hepatoxicity, and therefore the liver injury they cause is mixed. The drugs causing mixed liver injury include, for example, the following: Chlorpromazine, Phenylbutazone, Halothane, Chlordiazepoxide, Diazepam, Allopurinol, Phenobarbital, Naproxen, Propylthiouracil, Chloramphenicol, Trimethoprimsulfamethoxazxole, Amrinone, Disopyramide, Azathioprine, Cimetidine, and Ranitidine.

Vascular lesions of the liver, including thrombosis of the hepatic veins, occlusion of the hepatic venules or veno occlusive disease (VOD), and peliosis hepatitis, can be produced by drugs. In addition, lesions including sinusoidal dilatation, perisinusoidal fibrosis, and hepatoportal sclerosis can occur. Midzonal and pericentral sinusoidal dilatation was first reported as a complication of oral contraceptive therapy. Peliosis hepatitis is a condition consisting of large blood-filled cavities that results from leakage of red blood cells through the endothelial barrier, followed by perisinusoidal fibrosis. It has been described in patients taking oral contraceptives, anabolic steroids, azathioprine and danazol. Injury and occlusion of the central hepatic venules is also known to be related to the ingestion of pyrrolizidine alkaloids, such as bush teas. The initial lesion is central necrosis accompanied by a progressive decrease in venule caliber. All of these lesions may be only partially reversible when the drug is stopped and cirrhosis can develop.

Several types of benign and malignant hepatic neoplasm can result from the administration of hepatotoxic compounds. Adenomas, a lesion restricted to women in the childbearing years, is related to the use of contraceptive steroids and the risk increases with duration of use. Hepatocellular carcinoma may also be seen in patients taking androgenic hormones for aplastic anemia or hypopituitarism.

Hepatotoxic compounds known to cause hepatic lesions include the following: Contraceptive steroids, Pyrriolizidine alkaloids, Urethane, Azathioprine, 6-Mercaptopurine, 6-Thioguanine, Mitomycin, BCNU, Vincristine, Adriamycin, Intravenous Vitamin E, Anabolicandrogenic steroids, Azathioprine, Medroxyprogesterone acetate, Estrone sulfate, Tamoxifen, inorganic arsenicals, Thorium dioxide, Vitamin A, methotrexate, Methylamphetamine hydrochloride, Vitamin A, Corticosteroids, Thorium dioxide, and Radium therapy.

Liver damage caused by other factors usually takes similar forms. Liver damage, whether caused by the hepatotoxicity of a compound, radiation therapy, genetic predisposition, mechanical injury or any combination of such and other factors, can be detected by the biomarkers disclosed herein.

In other preferred embodiments, detection of biomarkers as diagnostic of liver injury, such as injury due to ischemia can be correlated with existing tests. These can include, but not limited to: alkaline phosphatase (AP); 5'-nucleotidase (5'-ND); and a-glutamyl transpeptidase (G-GT); leucine aminopeptidase (LAP); aspartate transaminase (AST); alanine transaminase (ALT); fructose-1,6-diphosphate aldolase (ALD); lactate dehydrogenase (LDH); isocitrate dehydrogenase (ICDH); ornithine-carbamoyltransferase (OCT); and sorbitol dehydrogenase (SDH) arginase; guanase; creatine phosphokinase (CPK); cholinesterase (ChE); procollagen type III peptide levels (PIIIP); ammonia blood levels in hepatoencephalopathies; ligand in levels in necrosis and hepatoma; hyaluronate levels due to hepatic endothelial cell damage; a-1-fetoprotein (AFP) levels to detect hepatoma; carcinoembryonic antigen (CEA) levels to detect cancer metastasis to the liver; elevations of antibodies against a variety of cellular components, such as, mitochondrial, and nuclear and specific liver membrane protein; and detection of proteins, such as, albumin, globin, amino acids, cholesterol, and other lipids. Also, biochemical analysis of a variety of minerals, metabolites, and enzymes obtained from liver biopsies can be useful in identifying further biomarkers in inherited, acquired, and experimentally induced liver disorders.

In other embodiments, the amount of detected biomarkers can be correlated to liver function tests to further assess liver injury. Liver function tests include the following: assessment of hepatic clearance of organic anions, such as, bilirubin, indocyanine green (ICG), sulfobromophthalein (BSP) and bile acids; assessment of hepatic blood flow by measurements of galactose and ICG clearance; and assessment of hepatic microsomal function, through the use of the aminopyrine breath test and caffeine clearance test. For example, serum bilirubin can be measured to confirm the presence and severity of jaundice and to determine the extent of hyperbilirubinemia, as seen in parenchymal liver disease. Aminotransferase (transaminase) elevations reflect the severity of active hepatocellular damage, while alkaline phosphatase elevations are found with cholestasis and hepatic infiltrates (Isselbacher, K. and Podolsky, D. in Hartison's Principles of Internal Medicine, $12^{th}$ edition. Wilson et al. eds., 2: 1301-1308 (1991)).

Enzyme Deficiencies

In another preferred embodiment, lack of detection (i.e. absence) of liver enzymes, e.g. ASS, is diagnostic of liver enzyme diseases. For example, lack of ASS (Argininosuccinate Synthetase Deficiency) is a genetic disease: Maple Syrup Urine Disease (MSUD) and Citrullinemia. Baseline levels in healthy controls are detectable with the methods of the invention and would expect to see below normal values in humans affected by the condition. In one embodiment, the compositions and methods of the invention identify at risk individuals. The identification can be determined in families, pregnant females by extracting samples such as blood, serum, amniotic fluid and the like. This would allow identification of risk and/or diagnosis of disease in an infant or fetus.

In a preferred embodiment, detection of the absence of one or more enzymes of arginine/urea/nitric oxide cycle, sulfuration enzymes and spectrin breakdown related products is diagnostic of liver enzyme deficiency associated diseases. Examples of these markers include, but not limited to: argininosuccinate synthetase (ASS) and argininosuccinate lyase (ASL), sulfuration (estrogen sulfotransferase (EST), squalene synthase (SQS), liver glycogen phosphorylase (GP), carbamoyl-phosphate synthetase (CPS-1), a-enolase 1, glucose-regulated protein (GRP) and spectrin breakdown products.

Maple Syrup Urine Disease: Maple Syrup Urine Disease (MSUD) or branched chain ketoaciduria is an autosomal recessive metabolic disorder of panethnic distribution. The neonatal screening for MSUD is performed either by the Guthrie bacterial inhibition assay or by tandem mass spectrometry (MS/MS). The worldwide incidence of MSUD is estimated to be approximately 1:185,000. MSUD is caused by a deficiency in activity of the branched chain a-keto acid dehydrogenase (BCKAD) complex. This metabolic block results in the accumulation of the branched chain amino acids (BCAA), such as leucine, isoleucine and valine and the corresponding branched chain a-keto acids (BCKA). These infants appear normal at birth, but after a few days they develop a poor appetite, become apathetic and lethargic, and then manifest neurologic signs, such as loss of normal reflexes. Alternating periods of atonia and hypertonicity appear, followed by convulsions and respiratory irregularities. MSUD is most often accompanied by a characteristic odor in the urine, perspiration and earwax. If left untreated, the disease is almost always fatal in the first weeks of life. Severe MSUD is characterized by plasma BCAA concentrations of: about $\geq 500$ micromoles/dL leucine; about $\geq 100$ micromole/dL isoleucine and about $\geq 100$ micromole/dL valine; and plasma BCKA concentrations of: about 60 to 460 micromoles/dL a.-ketoisocaproic acid, about 20 to 150 micromole/dL a-keto-$\beta$-methylvaleric acid, and about 2 to 35 micromole/dL a-ketoisovaleric acid. Preventing severe MSUD in a patient means that these levels are not reached in a patient who is diagnosed using the methods of the present invention and, who can then be treated immediately. Moderate MSUD is characterized by moderately elevated BCAA; for instance, about 60 to 100 micromoles/dL instead of $\geq 100$ micromoles/dL leucine.

The determination of at-risk patients and/or diagnosis using the present methods can be coupled with known tests such as BCAA levels.

Urea Cycle Disorders: The urea cycle consists of a series of five biochemical reaction and serves two purposes: (1) it incorporates nitrogen atoms not retained for net biosynthetic purposes into which serves as a waste nitrogen product, in order to prevent the accumulation of toxic nitrogenous compounds; and (2) it contains several of the biochemical reactions required for the de novo biosynthesis and degradation of arginine. Interruptions in the metabolic pathway for urea synthesis are caused by the deficiency or inactivity of any one of several enzymes involved in specific steps in the cascade. A defect in the ureageneic pathway has two consequences: arginine becomes an essential amino acid (except in arginase deficiency, where the enzyme defect results in a failure of degradation of arginine) and nitrogen atoms accumulate in a variety of molecules the pattern of which varies according to the specific enzymatic defect although plasma levels of ammonium and glutamine are increased in all urea cycle disorders not under metabolic control. Urea cycle disorders include: (a) carbamyl phosphate synthetase deficiency (CPSD), (b) N-acetyl glutamate synthetase deficiency, (c) ornithine transcarbamylase deficiency (OTCD), (d) argininosuccinic acid synthetase deficiency (ASD), (e) argininosuccinate lyase deficiency (ALD), and (f) arginase deficiency.

Except ornithine transcarbamylase deficiency, which is an X-linked generic disorder, urea cycle disorders are inherited by autosomal recessive fashion. Newborn screening using MS/MS technology can detect argininosuccinate synthetase deficiency (citrullinemia), argininosuccinate lyase deficiency (argininosuccinicaciduria), arginase deficiency and hyperammonemia-hyperomithinemia-homocitrullinemia syndrome (HHH).

In a preferred embodiment, detection of the absence of one or more enzymes of arginine/urea/nitric oxide cycle, sulfuration enzymes and spectrin breakdown related products is diagnostic of urea cycle disorders. Examples of these markers include, but not limited to: argininosuccinate synthetase (ASS) and argininosuccinate lyase (ASL), sulfuration (estrogen sulfotransferase (EST), squalene synthase (SQS), liver glycogen phosphorylase (GP), carbamoyl-phosphate synthetase (CPS-1), a-enolase 1, glucose-regulated protein (GRP) and spectrin breakdown products.

Severe urea cycle disorders are characterized by plasma ammonia level of about 2,000 to about 2,500 micrograms/dL ammonia and the patient requires a medical emergency for artificial respiration and hemodialysis in addition to the provision of alternative metabolism of ammonia. Preventing severe urea cycle disorders means that these levels are not reached in a patient treated with the method of the present invention and later diagnosed with a urea cycle disorder.

Moderate urea cycle disorders are characterized by plasma ammonia levels less than about 500 micromoles/dL and may not require such aggressive therapy. Thus, detection of hyperammonemia is most important for early diagnosis and effective treatment. Typically associated with this increase in ammonia buildup are acute episodes of vomiting, lethargy, convulsions and abnormal liver enzyme levels. Exposure to high levels of plasma ammonia is fatal typically following a period of lethargy, convulsions and coma. Even treated, protracted severe hyperammonemia leads to mental and physical retardation.

For fetuses at risk, antenatal diagnosis is available by a number of methods, particular to each disease, including enzyme analysis of fibroplasts cultured from aminocytes, in utero liver biopsy, and DNA techniques.

In a preferred embodiment, the absence of these enzymes is diagnostic of or identifies at-risk fetuses and newborns, using the methods and compositions of the invention.

Immunoassays

Antibodies directed against any one of the liver biomarkers (e.g., argininosuccinate synthetase (ASS) and argininosuccinate lyase (ASL), sulfuration (estrogen sulfotransferase (EST), squalene synthase (SQS), liver glycogen phosphorylase (GP), carbamoyl-phosphate synthetase (CPS-1), a-enolase 1, glucose-regulated protein (GRP) and spectrin breakdown products) can be used, as taught by the present invention, to detect and diagnose liver injury disease. Various histological staining methods, including immunohistochemical staining methods, may also be used effectively according to the teaching of the invention.

One screening method for determining whether a sample contains, for example, argininosuccinate lyase (ASL) proteins, peptides or fragments thereof comprises, for example, immunoassays employing radioimmunoassay (RIA) or enzyme-linked immunosorbent assay (ELISA) methodologies, based on the production of specific antibodies (monoclonal or polyclonal) to ASL protein. Any sample can be used, however, preferred samples comprising the liver biomarkers are blood, serum, plasma. Venipuncture (blood), urine and other body secretions, such as sweat and tears, can also be used as biological samples. For example, in one form of RIA, the substance under test is mixed with diluted antiserum in the presence of radiolabeled antigen. In this method, the concentration of the test substance is inversely proportional to the amount of labeled antigen bound to the specific antibody and directly related to the amount of free labeled antigen. Other suitable screening methods are readily apparent to those of skill in the art.

The present invention also relates to methods of detecting liver biomarker proteins or fragments thereof, in a sample or subject. For example, antibodies specific for ASL protein, or a fragment thereof, may be detectably labeled with any appropriate marker, for example, a radioisotope, an enzyme, a fluorescent label, a paramagnetic label, or a free radical.

Methods of making and detecting such detectably labeled antibodies or their functional derivatives are well known to those of ordinary skill in the art. The term "antibody" refers both to monoclonal antibodies, which are a substantially homogeneous population and to polyclonal antibodies, which are heterogeneous populations. Polyclonal antibodies are derived from the sera of animals immunized with an antigen. Monoclonal antibodies (MAbs) to specific antigens may be obtained by methods known to those skilled in the art. See, for example, U.S. Pat. No. 4,376,110. Such antibodies may be of any immunoglobulin class including IgG, IgM, IgE, IgA, IgD and any subclass thereof. It is appreciated that Fab and $F(ab')_2$ and other fragments of the antibodies useful in the present invention may be used for the detection and quantitation of an for example, ASL proteins, peptides or fragments thereof, according to the methods disclosed herein in order to detect and diagnose liver disease in the same manner as an intact antibody. Such fragments are typically produced by proteolytic cleavage, using enzymes such as papain (to produce Fab fragments) or pepsin (to produce $F(ab')_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody that can also be recognized by that antibody. Epitopic determinants usually consist of chemically active surface groupings of molecules such as amino acids or sugar side chains and have specific three dimensional structural characteristics as well as specific charge characteristics.

An "antigen" is a molecule capable of being bound by an antibody that is additionally capable of inducing an animal to produce antibody capable of binding to an epitope of that antigen. An antigen may have one, or more than one epitope. The specific reaction referred to above is meant to indicate that the antigen will react, in a highly selective manner, with its corresponding antibody and not with the multitude of other antibodies that may be evoked by other antigens. The antibodies, or fragments of antibodies, useful in the present invention may be used to quantitatively or qualitatively detect the liver biomarkers or used in histological stains to detect the presence of cells that contain, for example ASL proteins and fragment antigens. Thus, the antibodies (or fragments thereof) useful in the present invention may be employed histologically to detect or visualize the presence of argininosuccinate synthetase (ASS) and argininosuccinate lyase (ASL), sulfuration (estrogen sulfotransferase (EST), squalene synthase (SQS), liver glycogen phosphorylase (GP), carbamoyl-phosphate synthetase (CPS-1), a-enolase 1, glucose-regulated protein (GRP) and spectrin breakdown products, proteins, peptides, or fragments thereof.

Such an assay for detecting liver biomarkers, typically comprises incubating a biological sample from a subject suspected of having such a condition in the presence of a detectably labeled binding molecule (e.g., antibody) capable of identifying a biomarker and detecting the binding molecule which is bound in a sample.

Thus, in this aspect of the invention, a biological sample may be treated with nitrocellulose, or other solid support that is capable of immobilizing cells, cell particles or soluble proteins. The support may then be washed with suitable buffers followed by treatment with the detectably labeled, with for example, anti-ASL specific antibody. The solid phase support may then be washed with the buffer a second time to remove unbound antibody. The amount of bound label on said solid support may then be detected by conventional means. By "solid phase support" is intended any support capable of binding antigen or antibodies. Well-known supports, or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will note many other suitable carriers for binding monoclonal antibody or antigen, or are able to ascertain the same by use of routine experimentation.

One embodiment for carrying out the diagnostic assay of the present invention on a biological sample containing liver biomarkers, comprises contacting a detectably labeled antibody specific for a desired biomarker. For illustrative purposes, ASL is used as a non-limiting example. A detectably labeled anti-ASL specific antibody is bound to a solid support to effect immobilization of anti-ASL specific antibody; contacting a sample suspected of containing ASL or fragments thereof on the said solid support; incubating the detectably labeled anti-ASL specific antibody with the support for a time sufficient to allow the immobilized anti-ASL specific antibody to bind to ASL and fragments thereof. These steps are followed by washing and detecting the bound label and thereby detecting and quantifying ASL and fragments thereof.

Alternatively, labeled anti-ASL specific antibody and/or ASL protein complexes in a sample may be separated from a reaction mixture by contacting the complex with an immobilized antibody or protein which is specific for an immunoglobulin, e.g., Staphylococcus protein A, Staphylococcus protein G, anti-IgM or anti-IgG antibodies. Such anti-immunoglobulin antibodies may be polyclonal or preferably monoclonal. The solid support may then be washed with a suitable buffer to give an immobilized ASL/labeled anti-ASL specific antibody complex. The label may then be detected to give a measure of ASL protein. The specific concentrations of detectably labeled antibody and ASL, the temperature and time of incubation, as well as other assay conditions may be varied, depending on various factors including the concentration of protein in the sample, the nature of the sample, and the like. The binding activity of a given lot of anti-ASL antibody may be determined according to well-known methods. Those skilled in the art are able to determine operative and optimal assay conditions for each determination by employing routine experimentation. Other such steps as washing, stirring, shaking, filtering and the like may be added to the assays as is customary or necessary for the particular situation.

One of the ways in which the anti-ASL specific antibody can be detectably labeled is by linking the same to an enzyme. This enzyme, in turn, when later exposed to its substrate, will react with the substrate in such a manner as to produce a chemical moiety that can be detected, for example, by spectrophotometric, fluorometric or by visual means. Enzymes which can be used to detectably label the anti-ASL specific antibody include, but are not limited to, malate dehydrogenase, staphylococcal nuclease, d-V-steroid isomerase, yeast alcohol dehydrogenase, a-glycerophosphate dehydrogenase, triose phosphate isomerase, horseradish peroxidase, alkaline phosphatase, asparaginase, glucose oxidase, β-galactosidase, ribonuclease, urease, catalase, glucose-VI-phosphate dehydrogenase, glucoamylase and acetyl cholinesterase.

Detection may be accomplished using any of a variety of immunoassays. For example, by radioactively labeling the anti-ASL specific antibodies or antibody fragments, it is possible to detect ASL protein or fragments thereof, through the use of radioimmunoassays.

The radioactive isotope can be detected by such means as the use of a gamma counter or a scintillation counter or by autoradiography. Isotopes that are particularly useful for the purpose of the present invention are: $^3H$, $^{125}I$, $^{131}I$, $^{35}S$, $^{14}C$, and preferably $^{125}I$.

It is also desirable to label the anti-ASL specific antibody with a fluorescent compound. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The anti-ASL specific antibody can also be detectably labeled using fluorescence emitting metals such as $^{152}Eu$, or others of the lanthanide series. These metals can be attached to the anti-ASL specific antibody using such metal chelating groups as diethylenetriaminepentaacetic acid (DTPA) or ethylenediaminetetraacetic acid (EDTA). The anti-ASL specific antibody also can be detectably labeled by coupling it to a chemiluminescent compound. The presence of the chemiluminescent-tagged anti-ASL specific antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

The anti-ASL specific antibody may also be labeled with biotin and then reacted with avidin. Likewise, a bioluminescent compound may be used to label the anti-ASL specific antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the anti-ASL specific antibody may be accomplished by a scintillation counter, for example, if the detectable label is a radioactive gamma emitter, or by a fluorometer, for example, if the label is a fluorescent material. In the case of an enzyme label, the detection can be accomplished by calorimetric methods that employ a substrate for the enzyme. Detection may also be accomplished by visual comparison of the extent of enzymatic reaction of a substrate in comparison with similarly prepared standards.

For the purposes of the present invention, the ASL protein and/or fragments thereof, that are detected by this assay may be present in a biological sample. Any sample containing an ASL protein or fragments thereof, can be used. However, one of the benefits of the present diagnostic invention is that invasive tissue removal may be avoided. Therefore, preferably, the sample is a biological solution such as, for example, plasma, amniotic fluid, blood, serum, urine and the like. However, the invention is not limited to assays using only these samples, it being possible for one of ordinary skill in the art to determine suitable conditions that allow the use of other samples. Thus, the diagnosis of liver injury and/or disease can be established by a simple, non-invasive blood immunoassay that reveals ASL protein levels and/or fragments thereof, greatly increased over normal levels.

There are many different in vivo labels and methods of labeling known to those of ordinary skill in the art. Examples of the types of labels that can be used in the present invention include radioactive isotopes and paramagnetic isotopes. Those of ordinary skill in the art will know of other suitable labels for binding to the antibodies used in the invention, or is able to ascertain such, using routine experimentation. Furthermore, the binding of these labels to the antibodies can be done using standard techniques common to those of ordinary skill in the art.

An important factor in selecting a radionuclide for in vivo diagnosis is that the half-life of a radionuclide be long enough so that it is still detectable at the time of maximum uptake by the target, but short enough so that deleterious radiation upon the host is minimized. Ideally, a radionuclide used for in vivo imaging will lack a particulate emission, but produce a large number of photons in the 140-200 keV range, which maybe readily detected by conventional gamma cameras.

For in vivo diagnosis radionuclides may be hound to antibody either directly or indirectly by using an intermediary functional group. Intermediary functional groups that are often used in binding radioisotopes that exist as metallic ions to immunoglobulins are DTPA and EDTA. Typical examples of ions that can be bound to immunoglobulins are $^{99m}Tc$, $^{123}I$, $^{111}In$, $^{131}I$, $^{97}Ru$, $^{67}Cu$, $^{67}Ga$, $^{125}I$, $^{68}Ga$, $^{72}As$, $^{89}Zr$, and $^{201}Tl$.

For diagnostic in vivo imaging, the type of detection instrument available is a major factor in selecting a given radionuclide. The radionuclide chosen must have a type of decay that is detectable for a given type of instrument. In general, any conventional method for visualizing diagnostic imaging can be utilized in accordance with this invention. For example, PET, gamma, beta, and MRI detectors can be used to visualize diagnostic imagining.

The antibodies useful in the invention can also be labeled with paramagnetic isotopes for purposes of in vivo diagnosis. Elements that are particularly useful, as in Magnetic Resonance Imaging (MRI), include $^{157}Gd$, $^{55}Mn$, $^{162}Dy$, and $^{56}Fe$.

The antibodies useful in the present invention are also particularly suited for use in in vitro immunoassays to detect the presence of an ASL protein or fragments thereof, in body tissue, fluids (such as CSF, blood, plasma or serum), or cellular extracts. In such immunoassays, the antibodies may be utilized in liquid phase or, preferably, bound to a solid-phase carrier, as described above.

Those of ordinary skill in the art will know of other suitable labels that may be employed in accordance with the present invention. The binding of these labels to antibodies or fragments thereof can be accomplished using standard techniques commonly known to those of ordinary skill in the art. Coupling techniques mentioned in the latter are the glutaraldehyde method, the periodate method, the dimaleimide method, the m-maleimidobenzyl-N-hydroxy-succinimide ester method, all of which methods are incorporated by reference herein.

Removing a histological specimen from a patient, and providing the combination of labeled antibodies of the present invention to such a specimen may accomplish in situ detection. The antibody is preferably provided by applying or by overlaying the labeled antibody to a biological sample. Through the use of such a procedure, it is possible to determine not only the presence of ASL protein or fragments thereof, but also the distribution of ASL protein on the examined tissue. Using the present invention, those of ordinary skill will readily perceive that any of a wide variety of histological methods (such as staining procedures) can be modified in order to achieve such in situ detection.

The binding molecules of the present invention may be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested (i.e., blood, plasma or serum) and a quantity of detectably labeled soluble antibody is added to permit detection and/or quantitation of the ternary complex formed between solid-phase antibody, antigen, and labeled antibody.

Typical, immunometric assays include "forward" assays in which the antibody bound to the solid phase is first contacted with the sample being tested to extract the antigen from the sample by formation of a binary solid phase antibody-antigen complex. After a suitable incubation period, the solid support is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support through the unlabeled antibody, the solid support is washed a second time to remove the unreacted labeled antibody. This type of forward sandwich assay may be a simple "yes/no" assay to determine whether antigen is present or may be made quantitative by comparing the measure of labeled antibody with that obtained for a standard sample containing known quantities of antigen.

In another type of "sandwich" assay, which may also be useful with the antigens of the present invention, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplexed labeled antibody, The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

The above-described in vitro or in vivo detection methods may be used in the detection and diagnosis of liver disease without the necessity of removing tissue. Such detection methods may be used to assist in the determination of the stage of liver deterioration in liver injury and/or disease by evaluating and comparing the concentration of an ASL protein or fragments thereof, in the biological sample.

Identification of New Markers

In a preferred embodiment, a biological sample is obtained from a patient with liver injury. Biological samples comprising biomarkers from other patients and control subjects (i.e. normal healthy individuals of similar age, sex, physical condition) are used as comparisons. Biological samples are extracted as discussed above. Preferably, the sample is prepared prior to detection of biomarkers. Typically, preparation involves fractionation of the sample and collection of fractions determined to contain the biomarkers. Methods of pre-fractionation include, for example, size exclusion chromatography, ion exchange chromatography, heparin chromatography, affinity chromatography, sequential extraction, gel electrophoresis and liquid chromatography. The analytes also may be modified prior to detection. These methods are useful to simplify the sample for further analysis. For example, it can be useful to remove high abundance proteins, such as albumin, from blood before analysis.

In one embodiment, a sample can be pre-fractionated according to size of proteins in a sample using size exclusion chromatography. For a biological sample wherein the amount of sample available is small, preferably a size selection spin column is used. In general, the first fraction that is eluted from the column ("fraction 1") has the highest percentage of high molecular weight proteins; fraction 2 has a lower percentage of high molecular weight proteins; fraction 3 has even a lower percentage of high molecular weight proteins; fraction 4 has the lowest amount of large proteins; and so on. Each fraction can then be analyzed by immunoassays, gas phase ion spectrometry, fragments and derivatives thereof, for the detection of markers.

In another embodiment, a sample can be pre-fractionated by anion exchange chromatography. Anion exchange chromatography allows pre-fractionation of the proteins in a sample roughly according to their charge characteristics. For example, a Q anion-exchange resin can be used (e.g., Q HyperD F, Biosepra), and a sample can be sequentially eluted with eluants having different pH's. Anion exchange chromatography allows separation of biomarkers in a sample that are more negatively charged from other types of biomarkers. Proteins that are eluted with an eluant having a high pH is likely to be weakly negatively charged, and a fraction that is eluted with an eluant having a low pH are likely to be strongly negatively charged. Thus, in addition to reducing complexity of a sample, anion exchange chromatography separates proteins according to their binding characteristics.

In yet another embodiment, a sample can be pre-fractionated by heparin chromatography. Heparin chromatography allows pre-fractionation of the markers in a sample also on the basis of affinity interaction with heparin and charge characteristics. Heparin, a sulfated mucopolysaccharide, will hind markers with positively charged moieties and a sample can be sequentially eluted with eluants having different pH's or salt concentrations. Markers eluted with an eluant having a low pH are more likely to be weakly positively charged. Markers eluted with an eluant having a high pH are more likely to be strongly positively charged. Thus, heparin chromatography also reduces the complexity of a sample and separates markers according to their binding characteristics.

In yet another embodiment, a sample can be pre-fractionated by isolating proteins that have a specific characteristic, e.g. are glycosylated. For example, a homogenized liver tissue sample, serum sample, plasma sample, blood sample, can be fractionated by passing the sample over a lectin chromatography column (which has a high affinity for sugars). Glycosylated proteins will bind to the lectin column and non-glycosylated proteins will pass through the flow through. Glycosylated proteins are then eluted from the lectin column with an eluant containing a sugar, e.g., N-acetyl-glucosamine and are available for further analysis.

Thus there are many ways to reduce the complexity of a sample based on the binding properties of the proteins in the sample, or the characteristics of the proteins in the sample.

In yet another embodiment, a sample can be fractionated using a sequential extraction protocol. In sequential extraction, a sample is exposed to a series of adsorbents to extract different types of biomarkers from a sample. For example, a sample is applied to a first adsorbent to extract certain proteins, and an eluant containing non-adsorbent proteins (i.e., proteins that did not bind to the first adsorbent) is collected. Then, the fraction is exposed to a second adsorbent. This further extracts various proteins from the fraction. This second fraction is then exposed to a third adsorbent, and so on.

Any suitable materials and methods can be used to perform sequential extraction of a sample. For example, a series of spin columns comprising different adsorbents can be used. In another example, a multi-well comprising different adsorbents at its bottom can be used. In another example, sequential extraction can be performed on a probe adapted for use in a gas phase ion spectrometer, wherein the probe surface comprises adsorbents for binding biomarkers. In this embodiment, the sample is applied to a first adsorbent on the probe, which is subsequently washed with an eluant. Markers that do not bind to the first adsorbent are removed with an eluant. The markers that are in the fraction can be applied to a second adsorbent on the probe, and so forth. The advantage of performing sequential extraction on a gas phase ion spectrometer probe is that markers that bind to various adsorbents at every stage of the sequential extraction protocol can be analyzed directly using a gas phase ion spectrometer.

In yet another embodiment, biomarkers in a sample can be separated by high-resolution electrophoresis, e.g., one or two-dimensional gel electrophoresis. A fraction containing a marker can be isolated and further analyzed by gas phase ion spectrometry. Preferably, two-dimensional gel electrophoresis is used to generate two-dimensional array of spots of biomarkers, including one or more markers. See, e.g., Jungblut and Thiede, *Mass Spear. Rev.* 16:145-162 (1997).

The two-dimensional gel electrophoresis can be performed using methods known in the art. See, e.g., Deutscher ed., *Methods In Enzymology* vol. 182. Typically, biomarkers in a sample are separated by, e.g., isoelectric focusing, during which biomarkers in a sample are separated in a pH gradient until they reach a spot where their net charge is zero (i.e., isoelectric point). This first separation step results in one-dimensional array of biomarkers. The biomarkers in one dimensional array is further separated using a technique generally distinct from that used in the first separation step. For example, in the second dimension, biomarkers separated by isoelectric focusing are further separated using a polyacrylamide gel, such as polyacrylamide gel electrophoresis in the presence of sodium dodecyl sulfate (SDS-PAGE). SDS-PAGE gel allows further separation based on molecular mass of biomarkers. Typically, two-dimensional gel electrophoresis can separate chemically different biomarkers in the molecular mass range from 1000-200,000 Da within complex mixtures.

Biomarkers in the two-dimensional array can be detected using any suitable methods known in the art. For example, biomarkers in a gel can be labeled or stained (e.g., Coomassie Blue or silver staining). If gel electrophoresis generates spots that correspond to the molecular weight of one or more markers of the invention, the spot can be further analyzed by densitometric analysis or gas phase ion spectrometry. For example, spots can be excised from the gel and analyzed by gas phase ion spectrometry. Alternatively, the gel containing biomarkers can be transferred to an inert membrane by applying an electric field. Then a spot on the membrane that approximately corresponds to the molecular weight of a marker can be analyzed by gas phase ion spectrometry. In gas phase ion spectrometry, the spots can be analyzed using any suitable techniques, such as MALDI or SELDI.

Prior to gas phase ion spectrometry analysis, it may be desirable to cleave biomarkers in the spot into smaller fragments using cleaving reagents, such as proteases (e.g., trypsin). The digestion of biomarkers into small fragments provides a mass fingerprint of the biomarkers in the spot, which can be used to determine the identity of markers if desired.

In yet another embodiment, high performance liquid chromatography (HPLC) can be used to separate a mixture of biomarkers in a sample based on their different physical properties, such as polarity, charge and size. HPLC instruments typically consist of a reservoir of mobile phase, a pump, an injector, a separation column, and a detector. Biomarkers in a sample are separated by injecting an aliquot of the sample onto the column. Different biomarkers in the mixture pass through the column at different rates due to differences in their partitioning behavior between the mobile liquid phase and the stationary phase. A fraction that corresponds to the molecular weight and/or physical properties of one or more markers can be collected. The fraction can then be analyzed by gas phase ion spectrometry to detect markers.

Optionally, a marker can be modified before analysis to improve its resolution or to determine its identity. For example, the markers may be subject to proteolytic digestion before analysis. Any protease can be used. Proteases, such as trypsin, that are likely to cleave the markers into a discrete number of fragments are particularly useful. The fragments that result from digestion function as a fingerprint for the markers, thereby enabling their detection indirectly. This is particularly useful where there are markers with similar molecular masses that might be confused for the marker in question. Also, proteolytic fragmentation is useful for high molecular weight markers because smaller markers are more easily resolved by mass spectrometry. In another example, biomarkers can be modified to improve detection resolution. For instance, neuraminidase can be used to remove terminal sialic acid residues from glycoproteins to improve binding to an anionic adsorbent and to improve detection resolution. In another example, the markers can be modified by the attachment of a tag of particular molecular weight that specifically bind to molecular markers, further distinguishing them. Optionally, after detecting such modified markers, the identity of the markers can be further determined by matching the physical and chemical characteristics of the modified markers in a protein database (e.g., SwissProt, MASCOT).

After preparation, biomarkers in a sample are typically captured on a substrate for detection. Traditional substrates include antibody-coated 96-well plates or nitrocellulose membranes that are subsequently probed for the presence of proteins. Preferably, the biomarkers are identified using immunoassays as described above. However, preferred methods also include the use of biochips. Preferably the biochips are protein biochips for capture and detection of proteins. Many protein biochips are described in the art. These include, for example, protein biochips produced by Packard Bio-Science Company (Meriden, Conn.), Zyomyx (Hayward, Calif.) and Phylos (Lexington, Mass.). In general, protein biochips comprise a substrate having a surface. A capture reagent or adsorbent is attached to the surface of the substrate. Frequently, the surface comprises a plurality of addressable locations, each of which location has the capture reagent bound there. The capture reagent can be a biological molecule, such as a polypeptide or a nucleic acid, which captures other biomarkers in a specific manner. Alternatively, the capture reagent can be a chromatographic material, such as an anion exchange material or a hydrophilic material. Examples of such protein biochips are described in the following patents or patent applications: U.S. Pat. No. 6,225,047(Hutchens and Yip, "Use of retentate chromatography to generate difference maps," May 1, 2001), International publication WO 99/51773 (Kuimelis and Wagner, "Addressable protein arrays," Oct. 14, 1999), International publication WO 00/04389 (Wagner et al., "Arrays of protein-capture agents and methods of use thereof," Jul. 27, 2000), International publication WO 00/56934 (Englert et al., "Continuous porous matrix arrays," Sep. 28, 2000).

In general, a sample containing the biomarkers is placed on the active surface of a biochip for a sufficient time to allow binding. Then, unbound molecules are washed from the surface using a suitable eluant. In general, the more stringent the eluant, the more tightly the proteins must be bound to be retained after the wash. The retained protein biomarkers now can be detected by appropriate means.

Analytes captured on the surface of a protein biochip can be detected by any method known in the art. This includes, for example, mass spectrometry, fluorescence, surface plasmon resonance, ellipsometry and atomic force microscopy. MASS spectrometry, and particularly SELDI mass spectrometry, is a particularly useful method for detection of the biomarkers of this invention.

Preferably, a laser desorption time-of-flight mass spectrometer is used in embodiments of the invention. In laser desorption mass spectrometry, a substrate or a probe comprising markers is introduced into an inlet system. The markers are desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of markers of specific mass to charge ratio.

Matrix-Assisted laser desorption/ionization mass spectrometry, or MALDI-MS, is a method of mass spectrometry that involves the use of an energy absorbing molecule, frequently called a matrix, for desorbing proteins intact from a probe surface. MALDI is described, for example, in U.S. Pat. No. 5,118,937 (Hillenkamp et al.) and U.S. Pat. No. 5,045,694 (Beavis and Chait). In MALDI-MS the sample is typically mixed with a matrix material and placed on the surface of an inert probe. Exemplary energy absorbing molecules include cinnamic acid derivatives, sinapinic acid ("SPA"), cyano hydroxy cinnamic acid ("CHCA") and dihydroxybenzoic acid. Other suitable energy absorbing molecules are known to those skilled in this art. The matrix dries, forming crystals that encapsulate the analyte molecules. Then the analyte molecules are detected by laser desorption/ionization mass spectrometry. MALD1-MS is useful for detecting the biomarkers of this invention if the complexity of a sample has been substantially reduced using the preparation methods described above.

Surface-enhanced laser desorption/ionization mass spectrometry, or SELDI-MS represents an improvement over MALDI for the fractionation and detection of biomolecules, such as proteins, in complex mixtures. SELDI is a method of mass spectrometry in which biomolecules, such as proteins, are captured on the surface of a protein biochip using capture reagents that are bound there. Typically, non-bound molecules are washed from the probe surface before interrogation. SELDI is described, for example, in: U.S. Pat. No. 5,719,060 ("Method and Apparatus for Desorption and Ionization of Analytes," Hutchens and Yip, Feb. 17, 1998,) U.S. Pat. No. 6,225,047 ("Use of Retentate Chromatography to Generate Difference Maps," Hutchens and Yip, May 1, 2001) and Weinberger et al., "Time-of-flight mass spectrometry," in Encyclopedia of Analytical Chemistry, R. A. Meyers, ed., pp 11915-11918 John Wiley & Sons Chichester, 2000.

Markers on the substrate surface can be desorbed and ionized using gas phase ion spectrometry. Any suitable gas phase ion spectrometers can be used as long as it allows markers on the substrate to be resolved. Preferably, gas phase ion spectrometers allow quantitation of markers.

In one embodiment, a gas phase ion spectrometer is a mass spectrometer. In a typical mass spectrometer, a substrate or a probe comprising markers on its surface is introduced into an inlet system of the mass spectrometer. The markers are then desorbed by a desorption source such as a laser, fast atom bombardment, high energy plasma, electrospray ionization, thermospray ionization, liquid secondary ion MS, field desorption, etc. The generated desorbed, volatilized species consist of preformed ions or neutrals which are ionized as a direct consequence of the desorption event. Generated ions are collected by an ion optic assembly, and then a mass analyzer disperses and analyzes the passing ions. The ions exiting the mass analyzer are detected by a detector. The detector then translates information of the detected ions into mass-to-charge ratios. Detection of the presence of markers or other substances will typically involve detection of signal intensity. This, in turn, can reflect the quantity and character of markers bound to the substrate. Any of the components of a mass spectrometer (e.g., a desorption source, a mass analyzer, a detector, etc.) can be combined with other suitable components described herein or others known in the art in embodiments of the invention.

In another embodiment, an immunoassay can be used to detect and analyze markers in a sample. This method comprises: (a) providing an antibody that specifically binds to a marker; (b) contacting a sample with the antibody; and (c) detecting the presence of a complex of the antibody bound to the marker in the sample.

To prepare an antibody that specifically binds to a marker, purified markers or their nucleic acid sequences can be used. Nucleic acid and amino acid sequences for markers can be obtained by further characterization of these markers. The molecular weights of digestion fragments from each marker can be used to search the databases, such as SwissProt database, for sequences that will match the molecular weights of digestion fragments generated by various enzymes. Using this method, the nucleic acid and amino acid sequences of other markers can be identified if these markers are known proteins in the databases.

Alternatively, the proteins can be sequenced using protein ladder sequencing. Protein ladders can be generated by, for example, fragmenting the molecules and subjecting fragments to enzymatic digestion or other methods that sequentially remove a single amino acid from the end of the fragment. Methods of preparing protein ladders are described, for example, in International Publication WO 93/24834 (Chait et al.) and U.S. Pat. No. 5,792,664 (Chait et al.). The ladder is then analyzed by mass spectrometry. The difference in the masses of the ladder fragments identify the amino acid removed from the end of the molecule.

If the markers are not known proteins in the databases, nucleic acid and amino acid sequences can be determined with knowledge of even a portion of the amino acid sequence of the marker. For example, degenerate probes can be made based on the N-terminal amino acid sequence of the marker. These probes can then be used to screen a genomic or cDNA library created from a sample from which a marker was initially detected. The positive clones can be identified, amplified, and their recombinant DNA sequences can be subcloned using techniques which are well known. See, e.g., *Current Protocols for Molecular Biology* (Ausubel et al., Green Publishing ASSoc. and Wiley-Interscience 1989) *and Molecular Cloning: A Laboratory Manual,* 3rd Ed. (Sambrook et al., Cold Spring Harbor Laboratory, NY 2001).

Using the purified markers or their nucleic acid sequences, antibodies that specifically bind to a marker can be prepared using any suitable methods known in the art. See, e.g., Coligan, *Current Protocols in Immunology* (1991); Harlow & Lane, *Antibodies: A Laboratory Manual* (1988); Goding, *Monoclonal Antibodies: Principles and Practice* (2d ed. 1986); and Kohler & Milstein, *Nature* 256:495-497 (1975). Such techniques include, but are not limited to, antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

After the antibody is provided, a marker can be detected and/or quantified using any of suitable immunological binding assays known in the art (see, e.g., U.S. Pat. Nos. 4,366, 241; 4,376,110; 4,517,288; and 4,837,168). Useful assays include, for example, an enzyme immune assay (EIA) such as enzyme-linked immunosorbent assay (ELISA), a radioimmune assay (RIA), a Western blot assay, or a slot blot assay. These methods are also described in, e.g., *Methods in Cell Biology: Antibodies in Cell Biology*, volume 37 (Asai, Ed. 1993); *Basic and Clinical Immunology* (Stites & Ten, eds., 7$^{th}$ ed. 1991); and Harlow & Lane, supra.

Generally, a sample obtained from a subject can be contacted with the antibody that specifically binds the marker. Optionally, the antibody can be fixed to a solid support to facilitate washing and subsequent isolation of the complex, prior to contacting the antibody with a sample. Examples of solid supports include glass or plastic in the form of, e.g., a microtiter plate, a stick, a bead, or a microbead. Antibodies can also be attached to a probe substrate or protein chip array described above. The sample is preferably a biological fluid sample taken from a subject. Examples of biological fluid samples include blood, serum, plasma, liver cells, tissues, urine, tears, saliva etc. In a preferred embodiment, the biological fluid comprises serum or plasma. The sample can be diluted with a suitable eluant before contacting the sample to the antibody.

After incubating the sample with antibodies, the mixture is washed and the antibody-marker complex formed can be detected. This can be accomplished by incubating the washed mixture with a detection reagent. This detection reagent may be, e.g., a second antibody which is labeled with a detectable label. Exemplary detectable labels include magnetic beads (e.g., DYNABEADS™), fluorescent dyes, radiolabels, enzymes (e.g., horse radish peroxidase, alkaline phosphatase and others commonly used in an ELISA), and colorimetric labels such as colloidal gold or colored glass or plastic heads. Alternatively, the marker in the sample can be detected using an indirect assay, wherein, for example, a. second, labeled antibody is used to detect bound marker-specific antibody, and/or in a competition or inhibition assay wherein, for example, a monoclonal antibody which binds to a distinct epitope of the marker is incubated simultaneously with the mixture.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, marker, volume of solution, concentrations fragments and derivatives thereof. Usually the assays is carried out at ambient temperature, although they can be conducted over a range of temperatures, such as 10° C. to 40° C.

In a preferred embodiment, the immunoassay is a sandwich ELISA. Immunoassays can be used to determine presence or absence of a marker in a sample as well as the quantity of a marker in a sample. First, a test amount of a marker in a sample can be detected using the immunoassay methods described above. If a marker is present in the sample, it will form an antibody-marker complex with an antibody that specifically binds the marker under suitable incubation conditions described above. The amount of an antibody-marker complex can be determined by comparing to a standard. A standard can be, e.g., a known compound or another protein known to be present in a sample. As noted above, the test amount of marker need not be measured in absolute units, as long as the unit of measurement can be compared to a control.

The methods for detecting these markers in a sample have many applications. For example, one or more markers can be measured to aid in the diagnosis of liver injury, liver disease, the degree of injury, alcohol and drug abuse, fetal injury due to alcohol and/or drug abuse by pregnant mothers, etc. In another example, the methods for detection of the markers can be used to monitor responses in a subject, to treatment. In another example, the methods for detecting markers can be used to assay for and to identify compounds that modulate expression of these markers in vivo or in vitro.

Data generated by desorption and detection of markers can be analyzed using any suitable means. In one embodiment, data is analyzed with the use of a programmable digital computer. The computer program generally contains a readable medium that stores codes. Certain code can be devoted to memory that includes the location of each feature on a probe, the identity of the adsorbent at that feature and the elution conditions used to wash the adsorbent. The computer also contains code that receives as input, data on the strength of the signal at various molecular masses received from a particular addressable location on the probe. This data can indicate the number of markers detected, including the strength of the signal generated by each marker.

Data analysis can include the steps of determining signal strength (e.g., height of peaks) of a marker detected and removing "outliers" (data deviating from a predetermined statistical distribution). The observed peaks can be normalized, a process whereby the height of each peak relative to some reference is calculated. For example, a reference can be background noise generated by instrument and chemicals (e.g., energy absorbing molecule) which is set as zero in the scale. Then the signal strength detected for each marker or other biomolecules can be displayed in the form of relative intensities in the scale desired (e.g., 100). Alternatively, a standard (e.g., ASL protein) may be admitted with the sample so that a peak from the standard can be used as a reference to calculate relative intensities of the signals observed for each marker or other markers detected.

The computer can transform the resulting data into various foil iats for displaying. In one format, referred to as "spectrum view or retentate map," a standard spectral view can be displayed, wherein the view depicts the quantity of marker reaching the detector at each particular molecular weight. In another format, referred to as "peak map," only the peak height and mass information are retained from the spectrum view, yielding a cleaner image and enabling markers with nearly identical molecular weights to be more easily seen. In yet another format, referred to as "gel view," each mass from the peak view can be converted into a grayscale image based on the height of each peak, resulting in an appearance similar to bands on electrophoretic gels. In yet another format, referred to as "3-D overlays," several spectra can be overlaid to study subtle changes in relative peak heights. In yet another format, referred to as "difference map view," two or more spectra can be compared, conveniently highlighting unique markers and markers which are up- or down-regulated between samples. Marker profiles (spectra) from any two samples may be compared visually. In yet another format, Spotfire Scatter Plot can be used, wherein markers that are detected are plotted as a dot in a plot, wherein one axis of the plot represents the apparent molecular mass of the markers detected and another axis represents the signal intensity of markers detected. For each sample, markers that are detected and the amount of markers present in the sample can be saved in a computer readable medium. This data can then be compared to a control (e.g., a profile or quantity of markers detected in control, e.g., normal, healthy subjects in whom liver injury is undetectable).

Kits

The assay of the present invention is also ideally suited for the preparation of a kit. Such a kit may comprise a carrier means being compartmentalized to receive in close confinement therewith one or more container means such as vials, tubes and the like, each of said container means comprising the separate elements of the immunoassay. For example, there may be a container means containing a first antibody immobilized on a solid phase support, and a further container means containing a second detectably labeled antibody in solution. Further container means may contain standard solutions comprising serial dilutions of the liver biomarkers to be detected. The standard solutions of a each liver biomarker may be used to prepare a standard curve with the concentration of each liver biomarker plotted on the abscissa and the detection signal on the ordinate. The results obtained from a sample containing any one of the liver biomarkers may be interpolated from such a plot to give the concentration of each detected biomarker.

In one embodiment, a panel of biomarkers is provided in the kit. These biomarkers include but not limited to: argininosuccinate synthetase (ASS) and argininosuccinate lyase (ASL), sulfuration (estrogen sulfotransferase (EST), squalene synthase (SQS), liver glycogen phosphorylase (GP), carbamoyl-phosphate synthetase (CPS-1), a-enolase 1, glucose-regulated protein (GRP) and spectrin breakdown products.

In another embodiment, antibodies directed to a panel of liver biomarkers is provided in the kit. Antibodies, include but not limited to antibodies specific for argininosuccinate synthetase (ASS) and argininosuccinate lyase (ASL), sulfuration (estrogen sulfotransferase (EST), squalene synthase (SQS), liver glycogen phosphorylase (GP), carbamoyl-phosphate synthetase (CPS-1), a-enolase 1, glucose-regulated protein (GRP) and spectrin breakdown products. The antibodies can be polyclonal or monoclonal.

The kit can provide both the panel of liver biomarkers and the antibodies if desired. For example, argininosuccinate synthetase (ASS) and argininosuccinate lyase (ASL), sulfuration (estrogen sulfotransferase (EST), squalene synthase (SQS), liver glycogen phosphorylase (GP), carbamoyl-phosphate synthetase (CPS-1), a-enolase 1, glucose-regulated protein (GRP) and spectrin breakdown products.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention iscome apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in pertinent part for all purposes to the same extent as if each individual publication or patent document were so individually denoted. By their citation of various references in this document, Applicants do not admit any particular reference is "prior art" to their invention.

EXAMPLES

Materials and Methods

Rat Model of Ischemia/Reperfusion Injury

Adult male Sprague Dawley rats are anesthetized with 4% isoflurane until they reach a surgical level of anaesthesia. A nose cone continues to deliver the anaesthetic gases. A midline of approximately 3 cm long incisions is made (laparotomy), and the liver is exposed. The portal vein, hepatic artery and bile duct of the left lateral and median lobes is occluded by a small vascular clamp. The blood supply to the right lobe is uninterrupted and portal blood flow is maintained through them without evidence of vascular congestion of the alimentary tract. After 30 min of normothermic ischemia, recirculation of blood through the ischemic liver is achieved by removing the clamp for additional 30 min. After end of reperfusion, euthanasia of the animals is performed by bilateral thoracotomy, blood is collected, the liver is briefly perfused with cold PBS to remove residual blood and taken for analysis.

Liver Tissue Processing and Sample Preparation.

For high throughput screening—Western blot ((HTS-WB) (PowerBlot)) and conventional Western blot analyses, liver specimens are snap frozen in liquid nitrogen after removal. Liver samples from FR, naïve and sham-operated rats are homogenized on ice using Polytron in RIPA buffer consisting of PBS, 1% Nonidet P-40, 0.5% sodium deoxycholate, 0.1% SDS, 1 mM DTT, containing 0.1 mg/ml PMSF, 1 mM sodium orthovanadate, 5 mM EDTA, 5 mM EGTA and protease inhibitor cocktail (Roche, Inc). For r-caspase-3 and r-calpain-2 treatment in vitro, livers obtained from intact (naïve) rats, are homogenized in RIPA buffer consisting of PBS, 1% Nonidet P-40, 0.5% sodium deoxycholate, 0.1% SDS, 1 mM DTT, 5 mM EDTA, 5 mM EGTA without protease inhibitors. Homogenates are left on ice for 30 min and centrifuged for 15 min at 10,000 rpm at 4° C. Supernatants are removed and protein measured using bicinechoninic acid (Pierce, Inc). Intact liver samples are treated in vitro with caspase-3 (Chemicon, specific act. 1 μg/μl) or calpain-2 (Calbiochem, 0.25 μg/μl).

High Throughput Screen Western Blot (HTS-WB) and Conventional Western Blot Analyses.

The gel is 13×10 cm, 4-15% gradient SDS-polyacrylamide, 0.5 mm thick (Bio-Rad Criterion IPG) 200 μg of protein is loaded in one big well across the entire width of the gel. This translates into ~8 μg per lane on a standard 10 well mini-gel. The gel is run for 1.5 hours at 150 volts, proteins transferred to Immobilon-P membrane (Millipore). The membrane is blocked for one hour with blocking buffer.

The membrane is clamped with a western blotting manifold that isolates 40 channels across the membrane. In each channel, a complex antibody cocktail is added and hybridized for one hour at 37° C.

The blot is removed, washed and visualized for 30 minutes at 37° C. with secondary goat anti-mouse conjugated to Alexa680 fluorescent dye (Molecular Probes). The membrane is washed, dried and scanned at 700 nm (for monoclonal antibody target detection) using the Odyssey Infrared Imaging System.

MW Standards—Lanes 4 and 40 of all blots are loaded with two standardization cocktails. Data analysis—data analysis includes raw and normalized signal intensity data from each blot with changes greater than 1.5 fold indicated. A description of characteristics of the analysis follow: 1. Quantity—total intensity of a defined spot. 2.

Normalized Quantity—All blots are normalized to the sum intensity of all valid spots on a blot then multiplied by 1,000,000. 3/. Ratio—The Normalized Quantity for experimental bands expressed as a ratio of the Normalized Quantity for the corresponding control bands. The Ratio is used to determine increases or decreases in protein expression. Results are also expressed as Fold Change, a semi-quantitative value that represents the general trend of protein changes, either increasing or decreasing, for the experimental sample relative to control.

Changes are listed in order of confidence, level 10 being the highest confidence. Confidence levels are defined as: a) Level 10—Changes greater than 2 fold in all 4 comparisons from good quality signals that also pass a visual inspection; b) Level 9—Changes 1.5 to 1.9 fold in all 4 comparisons from good quality signals that also pass a visual inspection; c) Level 8—Changes greater than 2 fold in all 4 comparisons from low signals that pass a visual inspection; d) Level 7—Changes 1.25 to 1.5 fold in all 4 comparisons from good quality signals that pass a visual inspection; e) Level 6—Changes greater than 2 fold in all 4 comparisons that do not pass visual inspection; f) Level 5—Changes 1.5 to 1.9 fold in all 4 comparisons that do not pass visual inspection.

Targeted Analysis of Liver-specific Proteins

The analysis shown in Table 1, is performed by Western blot using antibody available through various sources. Typically, 25 μg protein are loaded with two identical sets of 5 samples, separated in 4-20% polyacrylamide gel mini-slabs, and transferred onto PVDF membrane. The membrane is cut in 2 pieces, blocked, probed with two different antibodies, visualized using ECL Plus Kit (Pierce, Inc) and scanned. The membranes are stripped using stripping buffer and re-probed with other two antibody. After visualizing the bands with EDCL Plus Kit and scanning, membranes are stripped again, probed with aII-spectrin antibody and developed using alkaline phosphatase detection method. For accurate assessment of molecular mass of developed proteins, two sets of protein standards are added and developed simultaneously (Magic Markers, Invitrogen, Inc).

Liquid Chromatography, SDS-PAGE, LC/Mass Spectrometry.

Briefly, The LC system is set up to run two columns in line: S-sepharose and Q-sepharose. Samples are filtered, protein (1 mg) is loaded into the sample loop, and run using gradient of Mobile Phase A (20 mM Tris-HCl) and B (20 mM Tris-HCl containing 1M NaCl. Fractions (1 ml) are collected, 1 fraction per minute, for a total of 32 fractions. The fractions are concentrated and subjected to SDS-PAGE on BioRad Criterion Gels, 4-20% Tris-HCl 18 well gels. The samples are run in pairs: sham-operated (control); I/R; untreated in vitro (control in vitro); caspase-3- and/or calpain-2 treated next to each other for each fraction. Gels are stained with Coomassie-R250 and are used to select bands for excision.

Band excision, protein reduction, alkylation, digestion and extraction is performed as previously described (Wang, K. K., Ottens, A., Haskins, W., Liu, M. C., Kobeissy, F., Denslow, N., Chen, S., and Hayes, R. L. (2004) Proteomics studies of traumatic brain injury. Int Rev Neurobiol 61, 215-240)). The LC which is used to elute the peptides from the column has three phases: Mobile Phase A—99.6% water, 0.4% acetic acid; Mobile Phase B—the organic phase—20% water, 0.4% acetic acid, 79.6% Methanol; Mobile Phase C—used for loading the sample from the tube to the column is 0.4% acetic acid, 4% acetonitrile, and 95.6% water. For mass-spectrometry, samples reconstituted in 15 μL of Mobile Phase C solution.

The MS is a LCQ Deca XP, quadrapole ion trap mass spectrometer. The peptides are loaded on to a reverse phase column and eluted into the MS using an organic gradient and electrospray ionization. Once the ions are inside the MS, several scans take place. First the full MS scan—every mass to charge value (m/z) from the sample that has entered the ion trap at the time of the scan is recorded. Each peak represents a mass to charge value which represents the parent ion. The mass spec picks the three most intense parent ions and does another scan, the MSMS scan. Each parent ion fragments into a product ion which produces spectra unique to a peptide. So, for each MS scan, three MSMS spectra are produced, each likely representing a different peptide. The collection of all these scans plotted together is the chromatogram, which is sent to BioWorks Browser. When a spectrum in the sample matches a spectrum in the database, it is assigned an Xcorr. This value indicates the level of similarity of the two spectra.

Time-course of Rat Liver Ischemia/Reperfusion.

Total 30 min of total normothermic ischemia is followed by 10, 30 and 180 min reperfusion. Additionally, 30 min partial ischcmia are generated in the media and left hepatic lobes by clamping the proper hepatic artery, portal branches and the common bile duct. This procedure leaves the portal branch to the right lope open and diminish intestinal hypoxia. Partial ischemia (~70% in blood supply) is performed if mortality rate at 180 min of reperfusion is high after 30 min of total hepatic triad occlusion.

Liver Sample Preparation, Protein Expression Studies and Analysis.

These are performed by conventional Western blot. The antibody used for a II-spectrin determination is against full size aII-spectrin molecule (Affinity, Inc), caspase-3 cleaved 150i fragment (Cell Signalling Technologies), caspase-3 generated 120 kDa fragment (Abs from our laboratory-CNPBR-UF) and calpain-2 cleaved 150 fragment (CNPBR-UF). Antibody against hepatic biomarkers is obtained from various commercial and non-commercial sources.

Serum and Plasma Sample Preparation.

Blood is collected from rat heart at the end of experimental procedures. Plasma is obtained from K-EDTA preserved blood by centrifugation. 20 μl of plasma or serum is mixed with 180 μl of RIPA buffer (with proteases inhibitors), vortexed, incubated on ice for 30 min and centrifuged. Supernatants are removed, aliquots mixed with sample buffer 1:1, heated and loaded onto gel.

Serum Enzyme Assays.

ALT, LDH and ₇-GTP activities are determined using kinetic methods with commercial Kits according to manufacturer's instructions.

Liver Immunohistochemistry.

Liver specimens of experimental rats are taken at the end of reperfusion for analysis of tissue injury. Samples of liver tissue are placed in 10% neutral formaline for routine H&E staining according to a standard protocol, or frozen immediately in OCT buffer for immunohistochemistry.

Immunostaining of Activated Caspase 3 and Calpain-2.

Cryopreserved 4 μm liver frozen sections are fixed in ice-cold 4% paraformaldehyde in PBS or −20° C. methanol for 20 min on ice. Samples are washed 3 times with PBS for 3 minutes each, permeabilized on ice with cold 0.5% Triton X-100/PBS/0.2% sucrose, washed with PBS and quenched with 0.1% sodium borohydride for 5 min. Samples are blocked at room temperature (RT) for 30 minutes in 20% goat serum in PBS and incubated overnight (+40° C.) in 20% goat serum/PBS with activated caspase-3 (17/19 kDa protein, Cell Signaling, Inc.) or calpain-2 (Chemicon, Inc.) mouse monoclonal antibody. After extensive wash, cover slips are incubated with anti-mouse IgG conjugated with fluorescent dye (AlexaGreen 488, Molecular Probes). The cover slips are mounted and analyzed using fluorescent microscope equipped with the Optical Camera (Zeiss, Inc).

In situ TUNNEL Assays on Liver Tissue Section.

TUNNEL Assays are performed using commercial PROMEGA Kit. Liver samples are fixed in 10% buffered formalin and embedded in paraffin. Tissue sections are placed on slides and then deparaffinized and rehydrated. Slides are subjected to proteinase K digestion for 15 minutes (0.2 M Tris/0.5 M EDTA, pH 8.0, proteinase K 1 mg/ml). Slides are washed with PBS, equilibrated with buffer for 15 min and stained with FITC-conjugated nucleotide mixture and TdT for 80 minutes. The enzymatic reaction is stopped, slides are counterstained with a propidium iodide/anti-fade DNA solution and photographed using fluorescent microscope equipped with the Optical Camera (Zeiss, Inc) with appropriated filter.

ASS Antibodies

A monoclonal antibody against the C' terminus of ASS is commercially available (BD Transduction Laboratories). Additional monoclonal antibodies are being produced in the Hybridoma Core Laboratory in the Biotechnology Program at the University of Florida. Mice are immunized with the same materials that were used to prepare the specific anti-ASS polyclonal antibody in rabbits. Hybridomas producing the desired monoclonal antibodies are cloned two times to ensure their stability and purity. At least 100 aliquots of founder cloned hybridoma cells are frozen to ensure a life-long supply of the antibody.

Antibody Analysis

Antigen binding affinities of all ASS antibodies are analyzed using indirect ELISA, Western blots, and the BIAcore 3000. For each specific ELISA capture and detection antibody pairs are selected that give optimal antigen binding and affinity. The selection of antibodies is based on those antibodies that have high affinities and recognize different epitopes on the biomarkers. Antibodies are selected that have high affinity constants composed of a fast on rate and a slow off rate as determined by the BIAcore 3000 (Protein Chemistry Core at the University of Florida). The BIAcore is a chip-based device that allows determination of affinity constants (including on and off rates) of the interactions between proteins and other proteins, peptides, or DNA. The instrument uses a highly sensitive surface plasmon resonance detection system allowing precise determination of affinity constants in real time without addition of exogenous labels.

Production of Recombinant ASS Antigen and Validation of SW ELISA.

ASS cDNA is commercially available from ATCC and is used for the production of recombinant protein. For standard curve assay, a serial dilution of 50-0.001 ng of purified protein/well are analyzed. This determines the dynamic range of the assay which is anticipated to be 100-1000-fold, encompassing concentrations that are likely to be present in blood or serum. The SW ELISA data have shown that the sensitivity is greater than highly sensitive ECL Western blot (high pg level).

BIAcore:

Two pmol of biomarker protein (50 ng) in PBST was diluted in 10 mM acetate buffer (pH 4.5). FC1 was of a CM5 chip was used as control, whereas FC2 was activated and injected with 5 μl biomarker at 10 μl/min, yielding a ΔRU of 475. Antibodies were diluted 1:10 in PBST and 20 μl were injected for 2 min (kinject) followed by dissociation of 3 min. Regeneration of the surface was performed by injecting 5 μl glycine (10 mM, pH 1.5). Antibody injection and regeneration was repeated without loss of surface reactivity.

Example 1

Expression of Argininosuccinate Synthase (ASS)

The data show that the ASS protein is expressed in adult rat tissues in the liver, much lesser extent kidney, and at very low levels, in testes. (i) ASS and its caspase-3 mediated breakdown products were up-regulated in the liver, and (ii) ASS accumulated in plasma after 30 min liver ischemia followed by 30 mM reperfusion. A number of experiments were conducted using a rat model of ischemia/reperfusion with the particular emphasis on different reperfusion time with a fixed 30 min of ischemia period. Accumulation of ASS in blood was time-dependent and attained a steady state at 3 hours after reperfusion. Plasma ASS levels correlated strongly with the severity of hepatic damage determined by classical histology analysis of liver tissue and immunostaining with activated caspase-3.

Example 2

Sandwich ELISA for the Specific and Quantitative Detection of Argininosuccinate Synthase (ASS) in Biological Fluids Based on human ASS protein published sequence (P00966), two peptides were designed and synthesized: N-47-ARKKALKLGAKKV-59-C (SEQ ID NO: 1) and N-2, 4-AKAPNTPDILEIEFKK-229-C (SEQ ID NO: 2). Currently, these peptides are employed to produce rabbit polyclonal antibody.

The sandwich ELISA assay is used as a diagnostic for liver ischemic injury in humans. This includes liver transplantation, acute liver failure of various etiology, septic shock due to abdominal and multiple trauma. Data show that similarly to rats, plasma ASS is not detected in control, healthy persons.

The ELISA is normalized against a measurement of known amounts of ASS in biological fluids, such as serum and plasma and tissues including liver. The standard ASS is obtained as recombinant GST-tagged protein. It was determined that the ASS monoclonal antibody recognized ASS at 46 kDa with high specificity and sensitivity. This antibody is used as a detection antibody in the specific ELISA. The produced two rabbit polyclonal antibodies that are specific for ASS are tested using BIAcore and the concentration is optimized for use in the ELISA by varying the concentration of antibody and ASS standard in controlled titration experiments. Various concentrations of protein and antibody are tested to determine the specificity and sensitivity of the antibody. Concentrations of protein and antibody that give 80% of the highest binding are chosen for the sandwich ELISA.

To determine reactivity and specificity of the antibodies a tissue panel is probed by Western blot. An indirect ELISA method is used with the recombinant ASS protein attached to the ELISA plate to determine the optimal concentrations of the antibodies to be used in the assay. This assay determines the robust concentration of anti-ASS to use in the assay. 96-well microplates are coated with 50 ng/well and the rabbit and mouse anti-Ass antibodies are serially diluted starting with a 1:250 dilution down to 1:10,000 to determine the optimum concentration to use for the assay. A secondary anti-rabbit (or mouse)-horseradish peroxidase (HRP) labeled detection antibody and Ultra-TMB are used as detection substrates to evaluate the results.

Once the concentration of antibody is determined for maximum signal, the maximum detection limit of the indirect ELISA for each antibody is determined. 96-well microplate are coated from 50 ng/well serially diluted to <1 pg/well. For detection the antibodies are diluted to the concentration determined above. This provides a sensitivity range for the ASS ELISA assays and the choice of antibody for capture and detection.

To optimize and enhance the signal in the sandwich ELISA, the detection antibody is directly labeled with HRP to avoid any cross reactivity and to enhance the signal with the amplification system, which is very sensitive. This format and amplification has successfully worked for other biomarkers in our laboratory. To build the SW ELISA assay, the wells of the 96-well plate are coated with saturating concentrations of purified antibody (250 ng/well), the concentration of ASS antigen will range from 50 ng to <1 pg/well and the detection antibody will be at the concentration determined above. Initially the complex is detected with a HRP-labeled secondary antibody to confirm the SW ELISA format, but will replace the detection system by the HRP-labeled detection antibody.

Example 3

Identification of Altered Proteins and their Breakdown Products in Rat Liver

Rats (Sprague Dawley, male, 225-250 g) were anesthetized with isofluoran, hepatoduodenal ligament immobilized and hepatic triad (portal vein, hepatic artery and bile duct) was occluded with small vascular clamp for 30 min of normothermic ischemia followed by 30 min reperfusion. At the end, blood was withdrawn; liver was briefly perfused with ice-cold PBS and removed for analysis. Sham operated rats were subjected to anesthesia without ligation of hepatic triad. Intact liver tissue and blood were obtained immediately after rat anesthesia. Intact liver tissues were treated in vitro with recombinant caspase-3 or calpain-2. Initially, for I/R injury biomarker discovery, a custom mini-array of 40 antibodies was designed.

The results are presented as images of 40 antibody western blot mini-screen of control (sham-operated) and I/R samples, in vitro caspase-3-treated intact samples and calpain-2 treated samples.

Example 4

Characterization of Novel Hepatic Biomarkers of Liver Injury

Figure 3A:
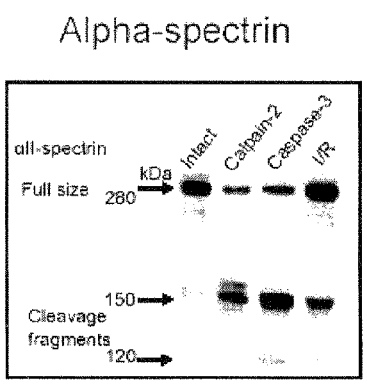
FIGS. 3A to 3B is a series of blots showing hepatic levels of aII-spectrin (A), argininosuccinate synthase (B) and γ-GTP (C) in intact, ischemia/reperfusion and intact liver treated in vitro with caspase-3 or calpain-2.
Figure 3B:
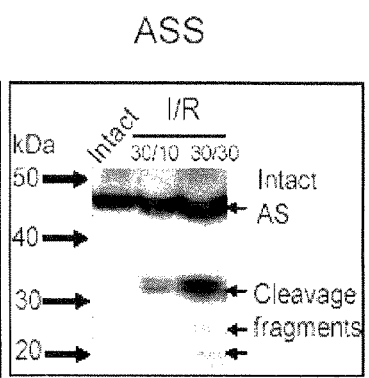

Hepatic α Thspectrin was cleaved in I/R liver via both caspase-3 and calpain-2 with accumulation of SBDP 150 kDa and 120 kDa (FIG. 3A). Characterization and comparison of three hepatic proteins as potential biomarkers of I/R-induced liver injury, included the following: argininosuccinate synthase (AS), liver isoform glutathione-S-transferase (GST-BB), and also γ-GTP and ALT, classic markers of hepatocellular injury. AS and γ-GTP were examined in liver tissues using western blot analysis with a particular emphasis on accumulation of possible breakdown products via caspase-3 and/or calpain-2 (FIGS. 3B and 3C).

Figure 3C:
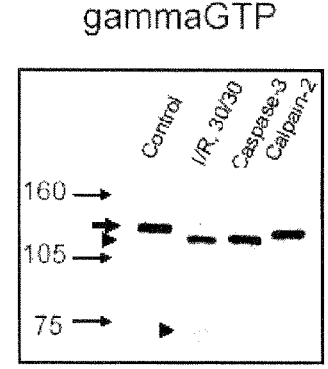
FIG. 3C shows detection of γGTP.
Figure 4A:
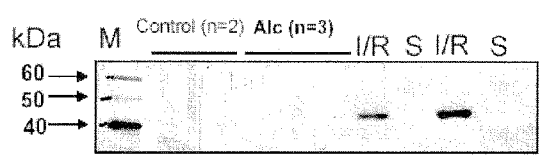
FIG. 4A shows an electro chemiluminescent (ECL) stain wherein ASS is detected in plasma.
Figure 4B:
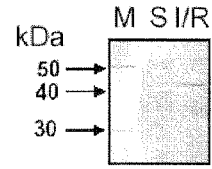
FIG. 4B shows an alkaline phosphatase detecting ASS in plasma. Alc—chronic alcohol treatment in rats. I/R—liver ischemia/reperfusion. S—sham operated rats, no vena portae ligation. C—control (normal rats). M—molecular weight markers.
Figure 5:
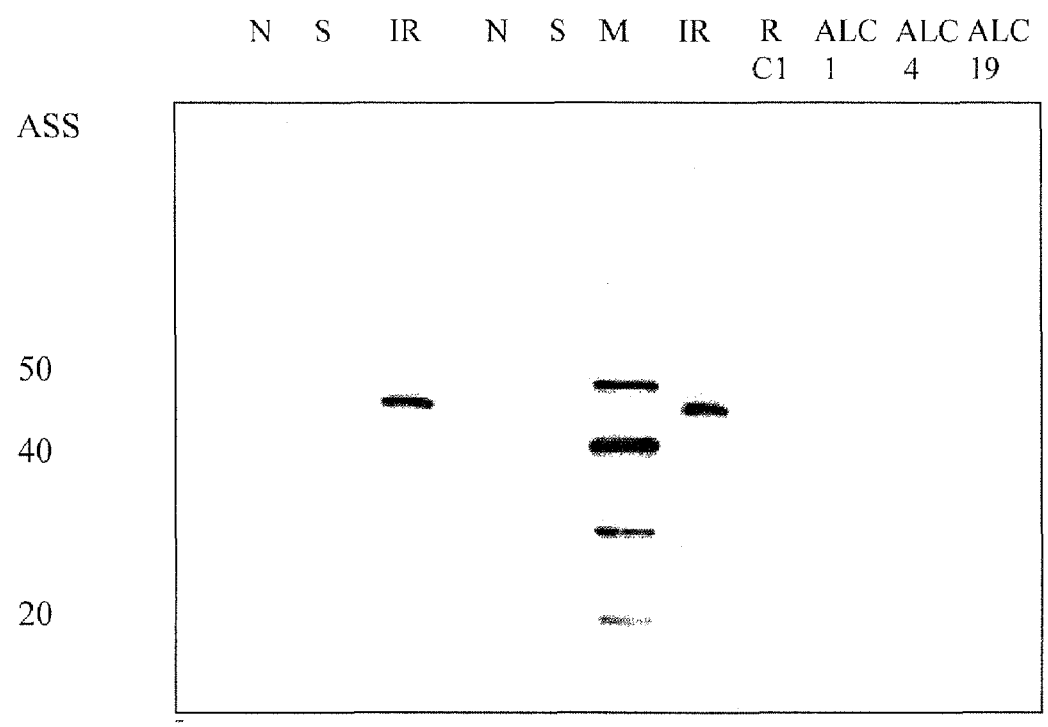
FIG. 5 is a blot showing detection of biomarker ASS in the plasma of rats with liver injury. Liver injuries included in the experiments were: Alc—chronic alcohol treatment in rats. I/R—liver ischemia/reperfusion. Controls were: S—sham operated rats, no vena portae ligation. N—naïve, intact rats. (normnal rats). RC1—high sucrose Alc control. M—molecular weight markers.
Figure 6:
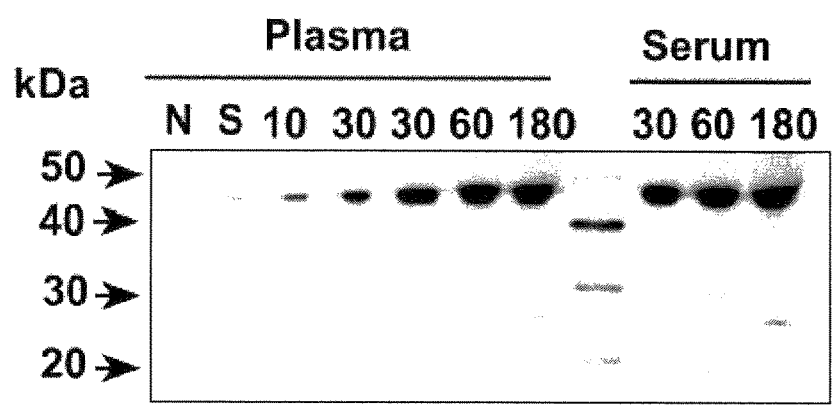
FIG. 6 is a blot showing the reperfusion time-course of ASS accumulation in rat plasma and serum after 30 minutes of ischemia.
Figure 7:
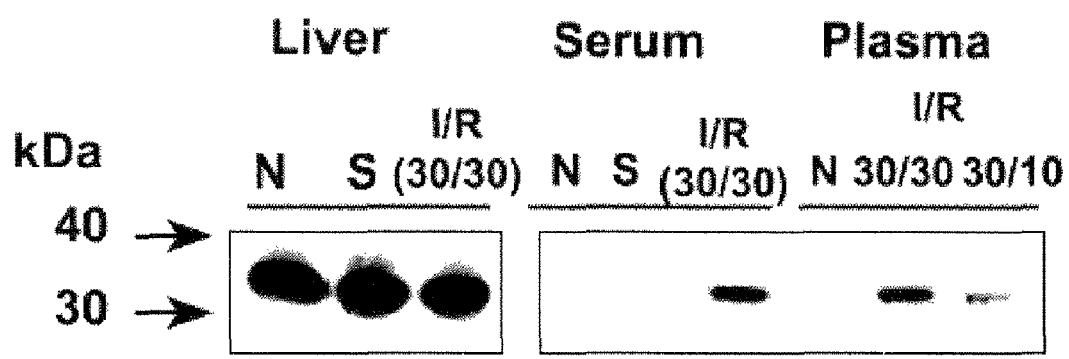
FIG. 7 is a blot showing detection of EST-1 in the liver, serum and plasma after 30 minutes of ischemia.
Figure 8:
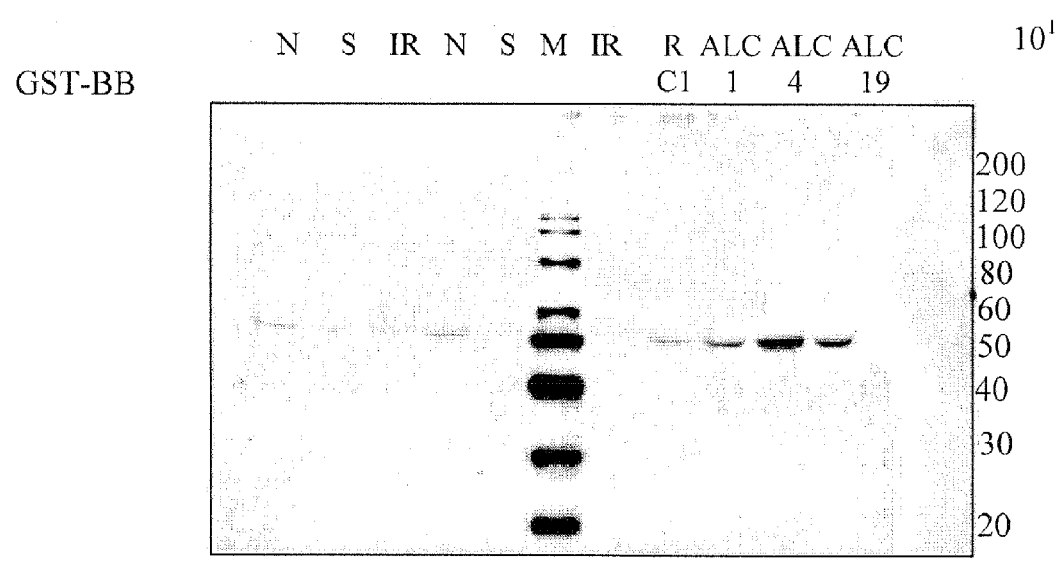
FIG. 8 is a blot showing the detection of glutathione-S-transferase in rat plasma, using ECL detection methods. Liver injuries included in the experiments were: Alc—chronic alcohol treatment in rats. I/R—liver ischemia/reperfusion. Controls were: S—sham operated rats, no vena portae ligation. N—naïve, intact rats. (normal rats). RC1—high sucrose Alc control. M—molecular weight markers.
Figure 9:
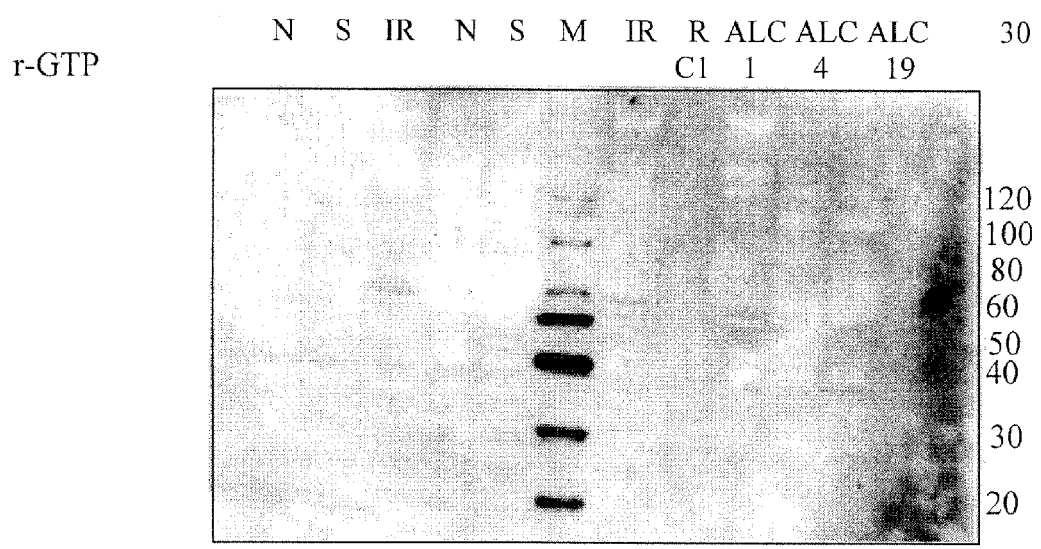
FIG. 9 is a blot showing the detection of γ-GTP in rat plasma, using ECL detection methods. Liver injuries included in the experiments were: Alc—chronic alcohol treatment in rats. I/R—liver ischemia/reperfusion. Controls were: S—sham operated rats, no vena portae ligation. N—naïve, intact rats. (normal rats). RC1—high sucrose Alc control. M—molecular weight markers.
Figure 10:
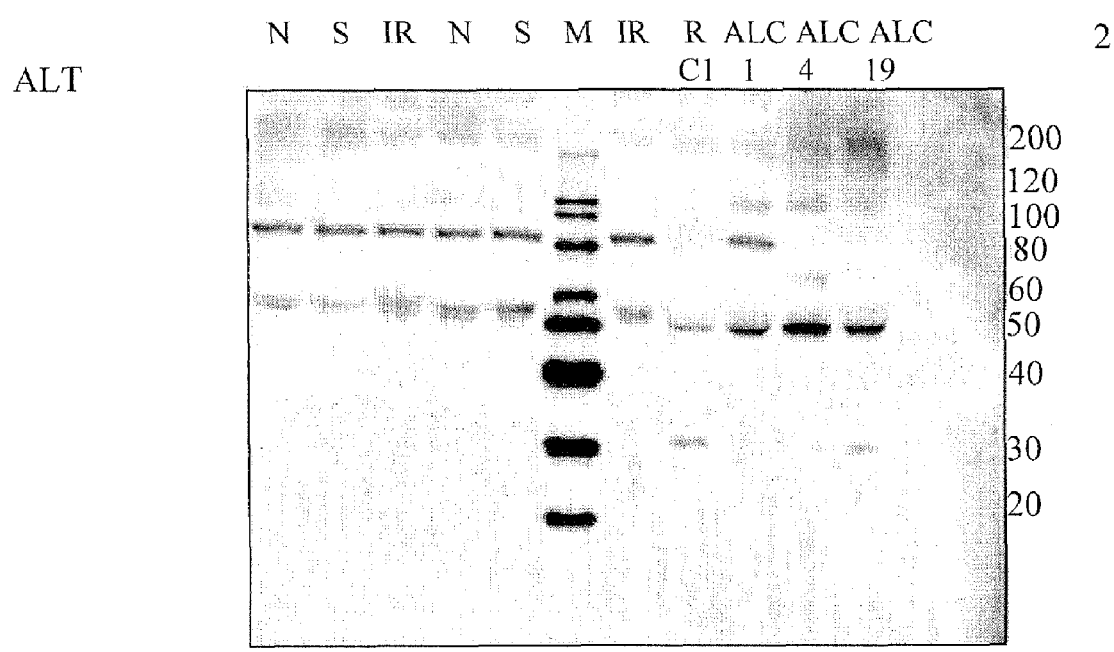
FIG. 10 is a blot showing the detection of ALT in rat plasma, using ECL detection methods. Liver injuries included in the experiments were: Alc—chronic alcohol treatment in rats. I/R—liver ischemia/reperfusion. Controls were: S—sham operated rats, no vena portae ligation. N—naive, intact rats. (normal rats). RC1—high sucrose Alc control. M—molecular weight markers.
Figures 11A, 11B, 11C, 11D:
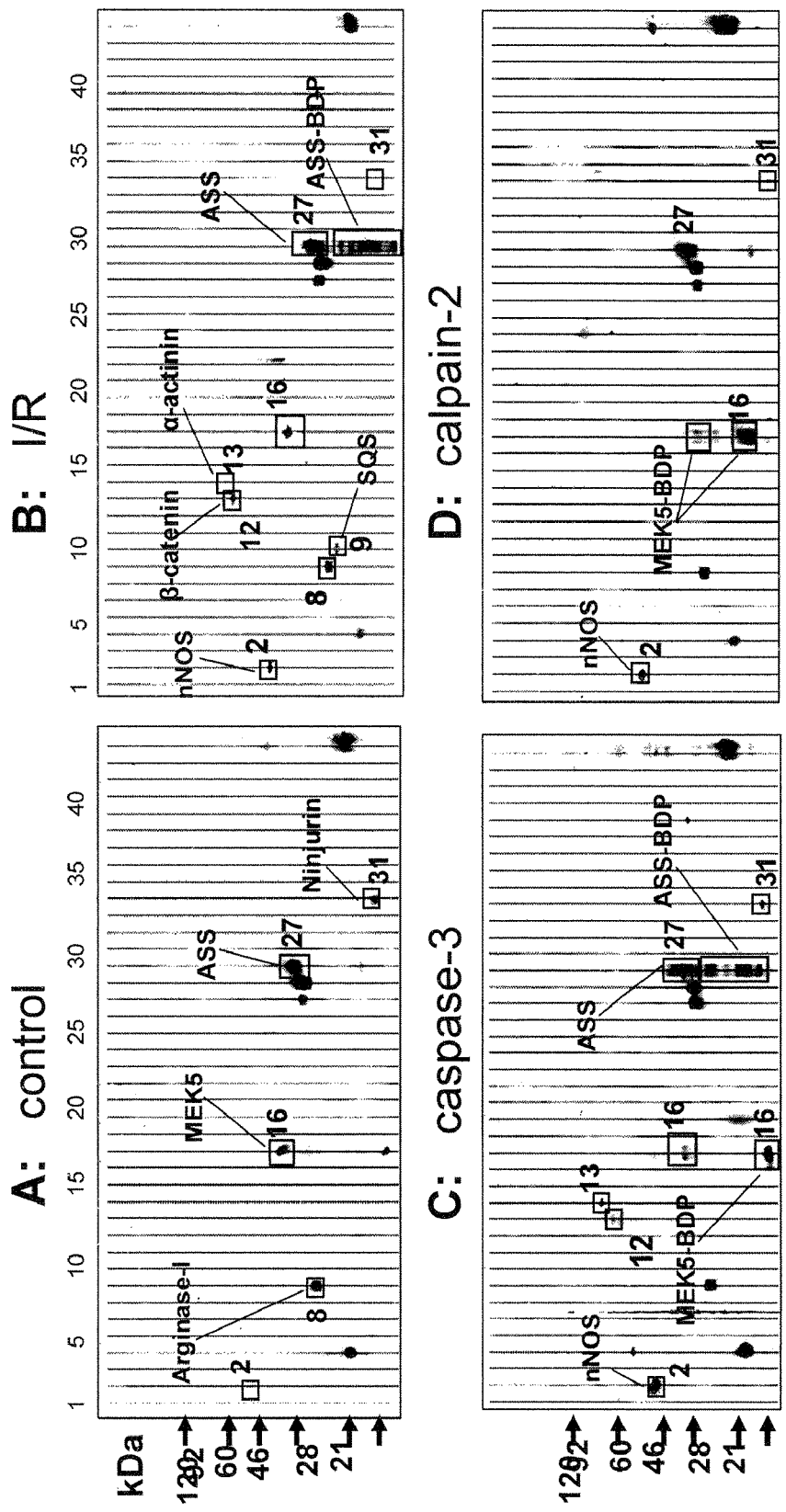
FIGS. 11A-11D are scans of immunoblots showing high throughput immunoblotting (HTPI) of liver samples using custom 40 antibody mini-screen array. Liver tissue obtained from four rats in each experimental group was pooled and processed as described in Materials and Methods in detail.
Figure 12:
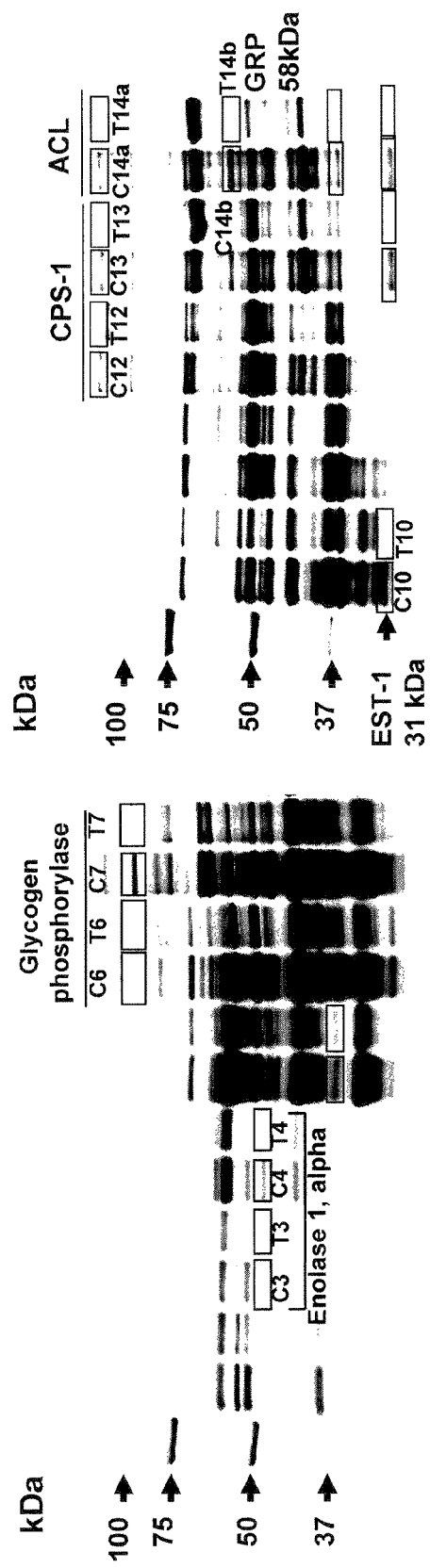
FIG. 12 shows differential SDS-PAGE display of protein fractions collected after combined cation-anion exchange (CAX) chromatography. The CAX fractions obtained from control (C) and I/R (T) samples were paired up and loaded side-by-side on SDS-PAGE. Proteins with differential expression were quantified using Phoretix 1D software. The numbers represent fraction number of control (C) or I/R sample, respectively. Portions of two gels containing fractions 1 to 15 are shown. Labeled boxes depict differentially displayed proteins already identified by RPLC-MSMS. Proteins identity determined by RPLC-MSMS are named next to each box. Unlabeled boxes show proteins to be identified.
Figure 13A:
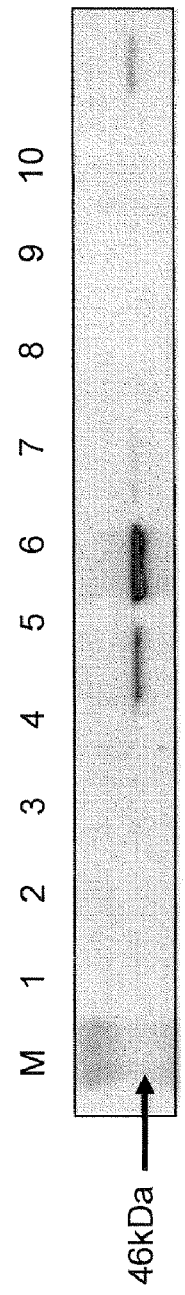
FIG. 13A shows a Western immunoblot of Rat G1 N1+N2 tissue panel probed with ASS MAb antibody, separated on 10-20%. Lane 1—Brain; Lane 2—Diaphragm; Lane 3-Heart; Lane 4—Kidney; Lane 5—Liver; Lane 6—Lung; Lane 7—Skeletal muscle; Lane 8—Skin; Lane 9—Spleen; Lane 10—Testes. Western blot screened with ASS (BD#611700) Mab.
Figure 13B:
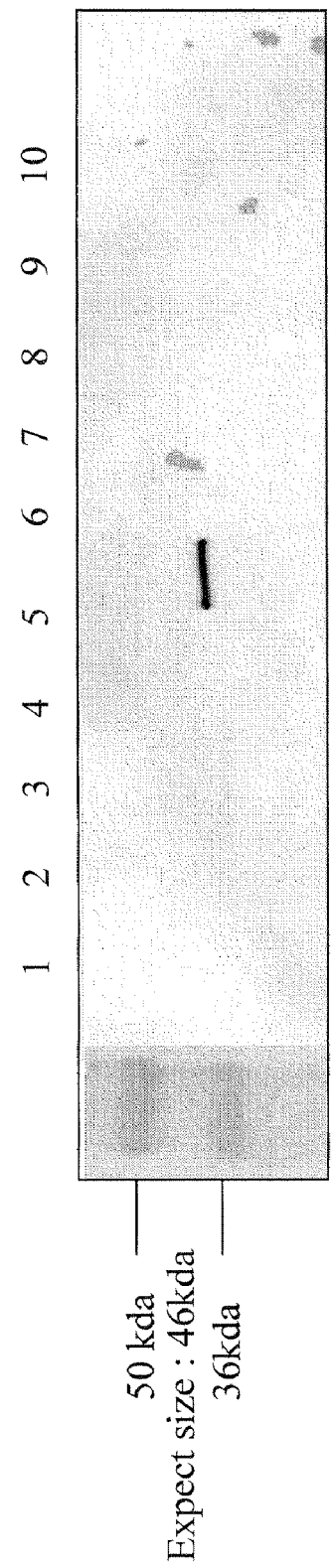
FIG. 13B shows a Western Immunoblot of a rat tissue panel probed with ASS2 PAb antibody (rabbit) separated on 10-20%. Lane 1—Brain; Lane 2—Diaphragm; Lane 3—Heart; Lane 4—Kidney; Lane 5—Liver; Lane 6—Lung; Lane 7—Skeletal muscle; Lane 8—Skin; Lane 9—Spleen; Lane 1—Testes.
Figure 14:
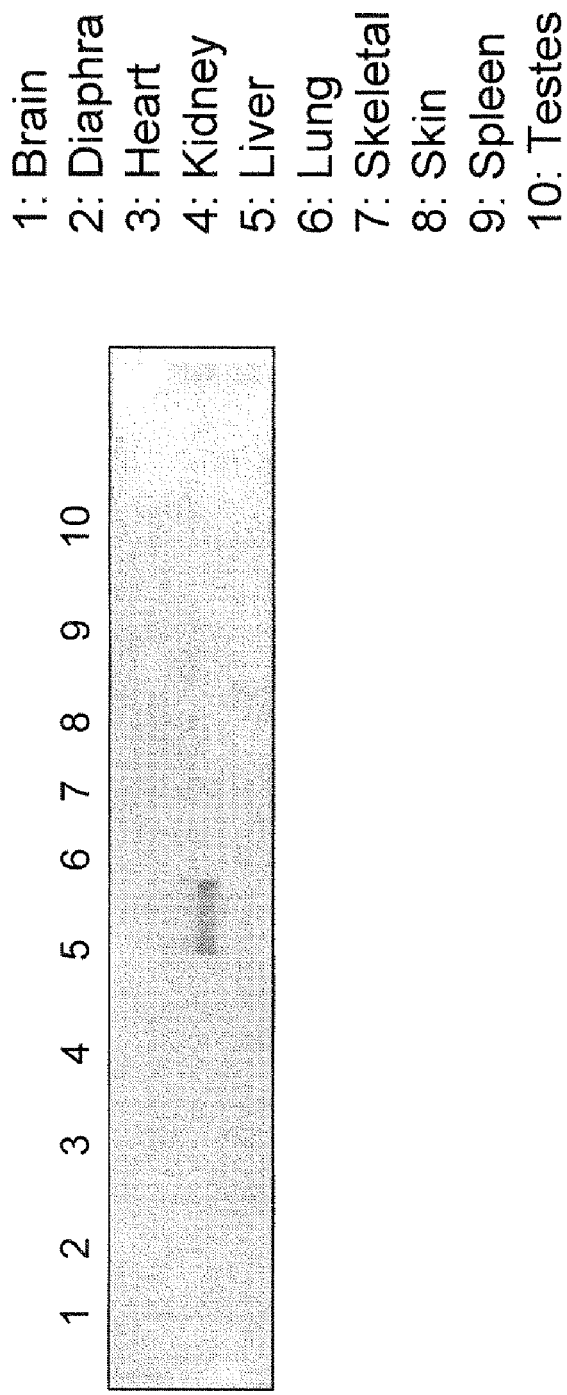
FIG. 14 is a Western blot of a rat tissue panel showing EST-1 probed with mouse antibody. Lane 1: Brain; Lane 2: Diaphra; Lane 3: Heart; Lane 4: Kidney; Lane 5: Liver; Lane 6: Lung; Lane 7: Skeletal; Lane 8: Skin; Lane 9: Spleen; Lane 10: Testes.
Figure 15:
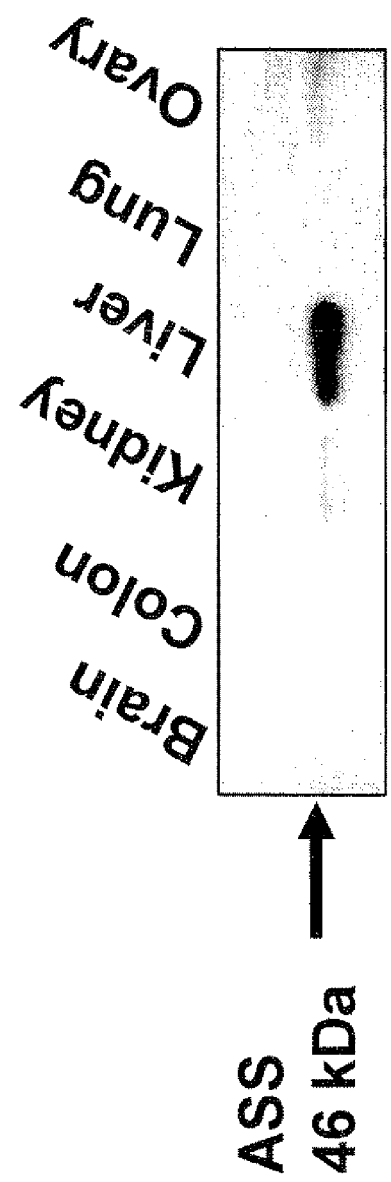
FIG. 15 is a Western blot showing ASS partial human tissue panel, 2 microgram protein/lane; BD monoclonal ASS antibody.
Figures 16A, 16B, 16C, 16D:
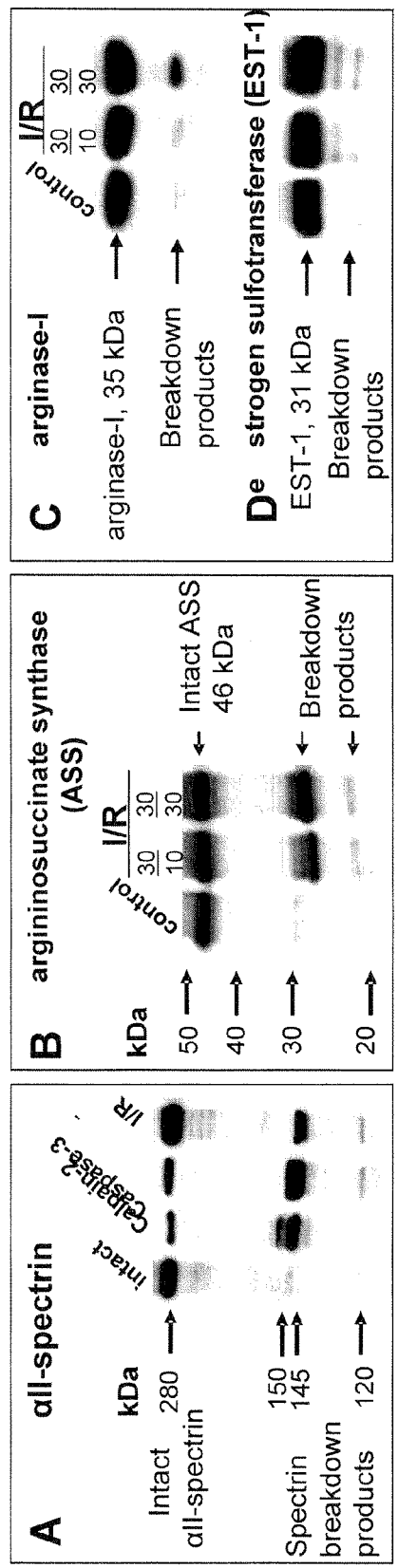
FIGS. 16A-16D are Western blots showing hepatic expression of cytoskeletal αII-spectrin, liver-specific marker proteins, and their breakdown products following liver ischemia/reperfusion injury. Liver samples were obtained from intact animals, control (sham operated) or rats subjected to 30 min hepatic ischemia (I/R) followed by 10 and 30 min reperfusion. Intact liver tissue lysates were treated in vitro with recombinant caspase-3 or calpain-2 (FIG. 16A) as described in Materials and Methods. Hepatic proteins (25 μg) were analyzed by SDS-PAGE/Western blotting with antibodies to non-erytroid αII-spectrin (FIG. 16A), argininosuccinate synthase (FIG. 16B), arginase-I (FIG. 16C) and estrogen sulfotransferase (FIG. 16D), and visualized using ECL.
Figure 17:
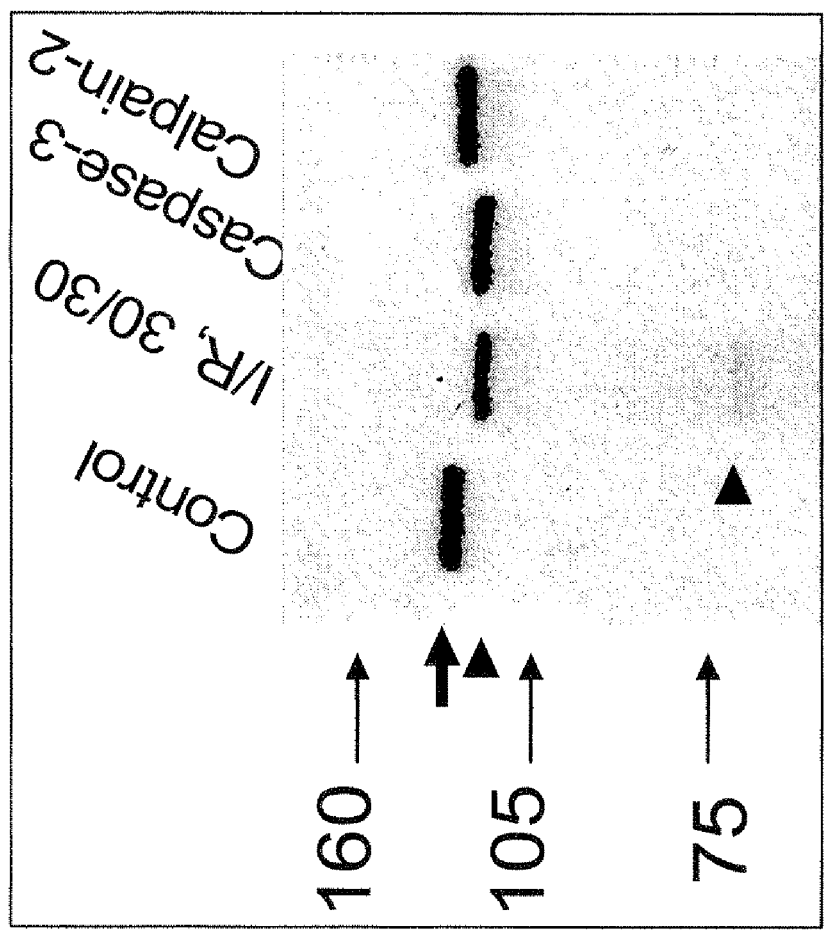
FIG. 17 is a Western blot showing γGTP in the liver tissue of I/R and normal rats and normal liver tissue treated with caspase-3 and calpain-2.
Figure 18A:
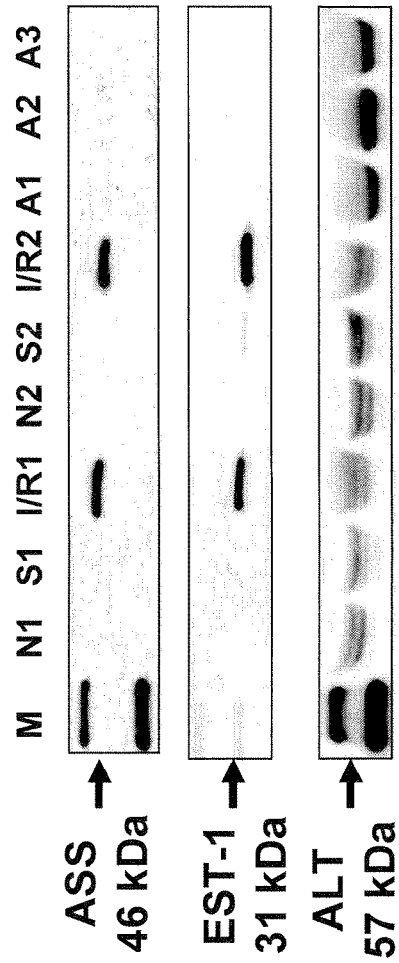
FIGS. 18A and 18B are Western blots showing accumulation of biomarkers of liver injury in blood after hepatic ischemia/reperfusion, chronic alcoholic disease and acute endotoxic liver injury.
Figure 18B:
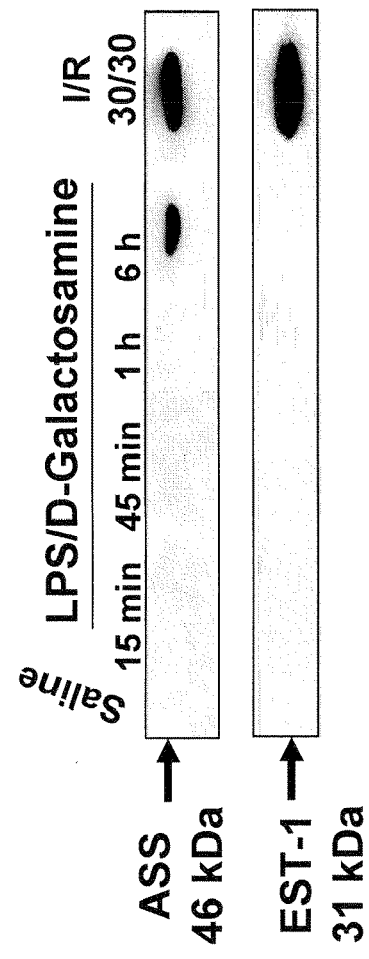
Figure 19A:
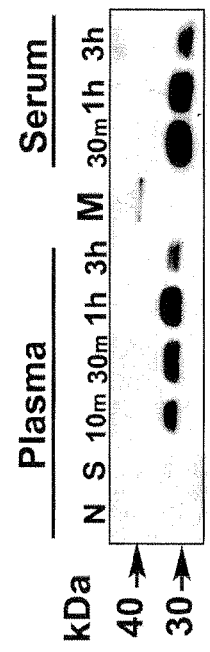
FIGS. 19A-19D show Western blots (FIGS. 19A, 19B) and graphs (FIGS. 19C and 19D) showing time-dependent accumulation of blood ASS and EST-1 after I/R in rats. Blood was withdrawn from rat heart following 30 min ischemia followed by different times of reperfusion as described in Experimental Procedures. Proteins were separated by SDS-PAGE/Western blot with antibody against ASS (FIG. 19A) and EST-1 (FIG. 19B). Images were captured and protein bands were calculated using ImageJ software (FIGS. 19C, 19D). Representative blots from 5 performed using at least 4 different experiments are shown. N-intact, naïve rats (n=5), S-sham operated rats (n=4); I/R-30 min ischemia followed by 10-180 min of reperfusion (n=4).
Figure 19B:
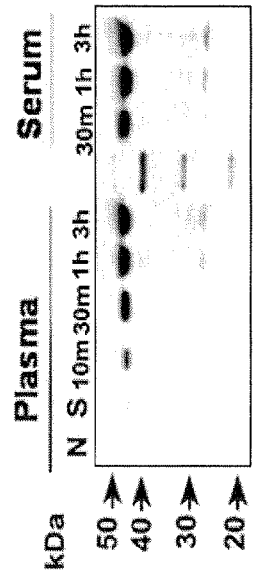
Figure 19C:
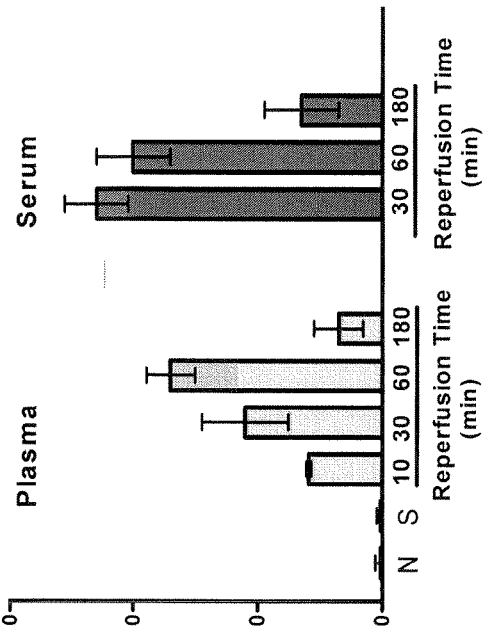
Figure 19D:
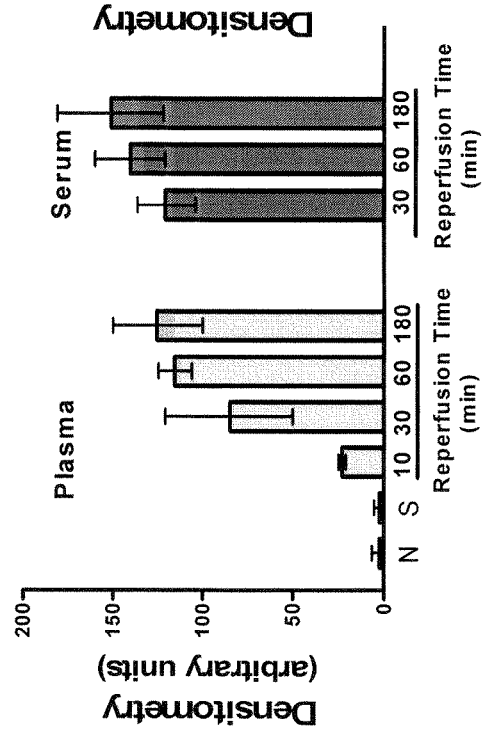
Figure 20:
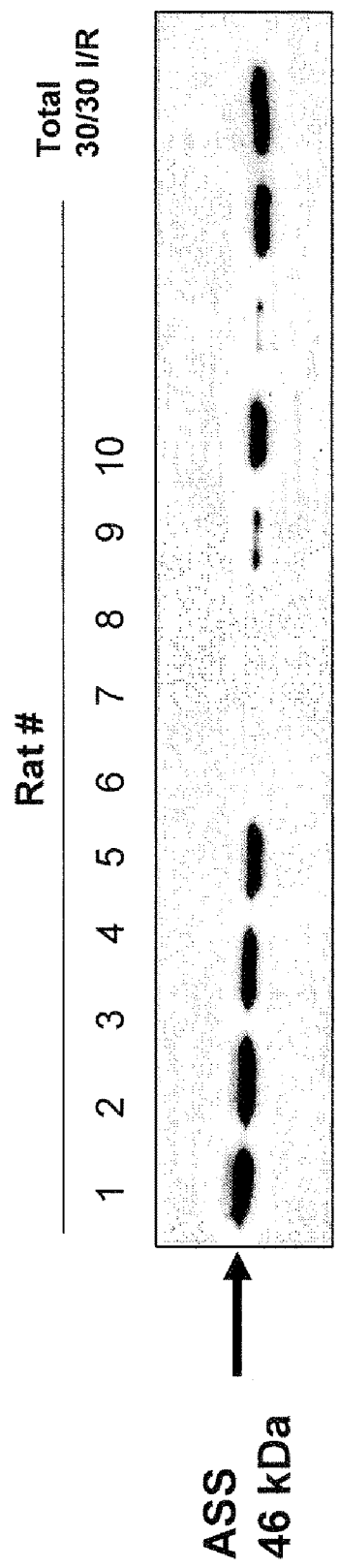
FIG. 20 shows a Western blot of partial 60 min ischemia/24 hours reperfusion with antibody against ASS.
Figure 21:
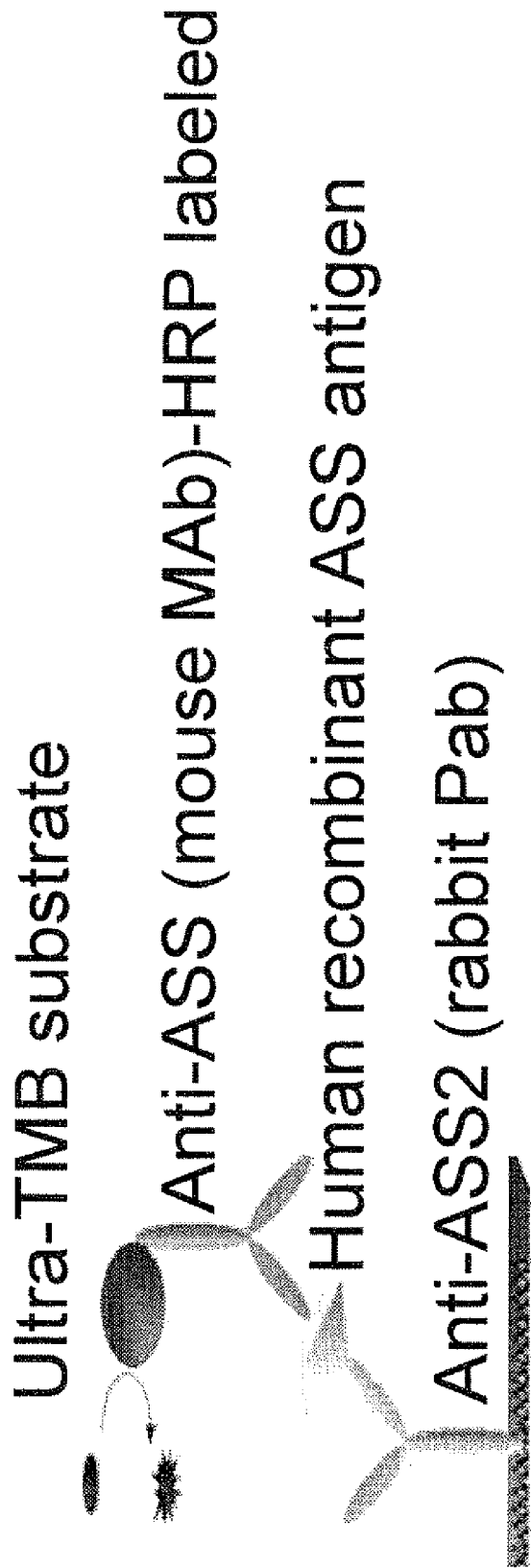
FIG. 21 is a schematic representation of the method used in a sandwich ELISA.
Figures 22A, 22B:
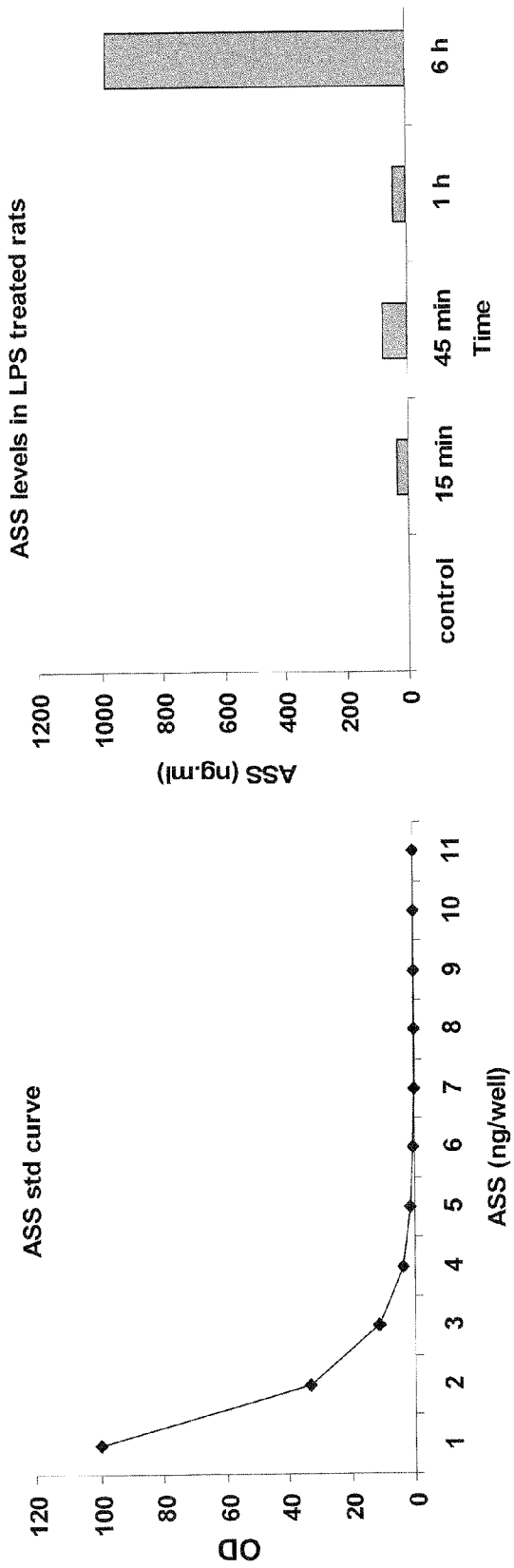
FIGS. 22A-22B are graphs showing the calibration curve for detection of rASS (FIG. 22A) and levels of serum ASS determined by SW ELISA in rats subjected to LPS/D-Gal treatment (FIG. 22B).
Figure 24:
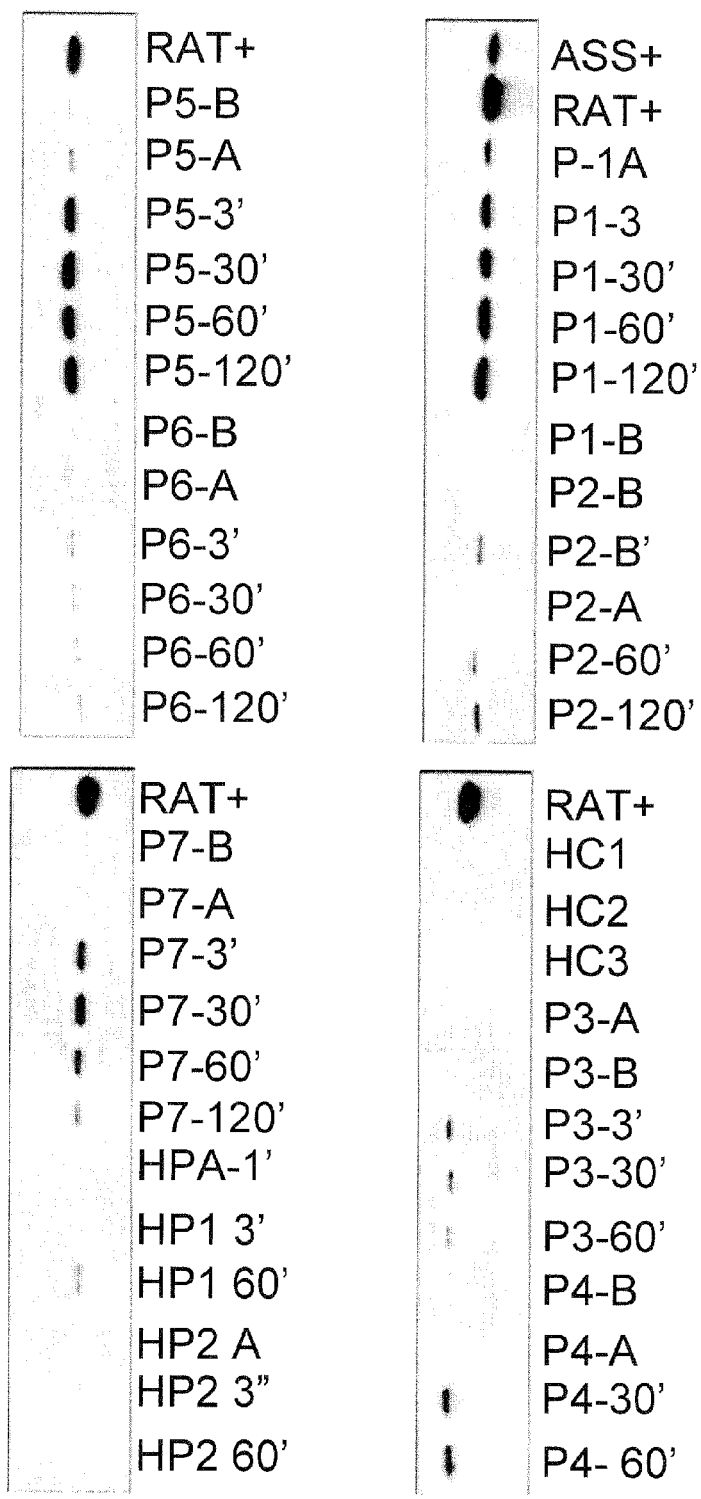
FIG. 24 is a Western blot of human transplantation primary data. P# is patient #; B-baseline (before surgery), A-ahepatic state; 3',30',60',120'-min after reperfusion of transplanted liver.
Figure 25:
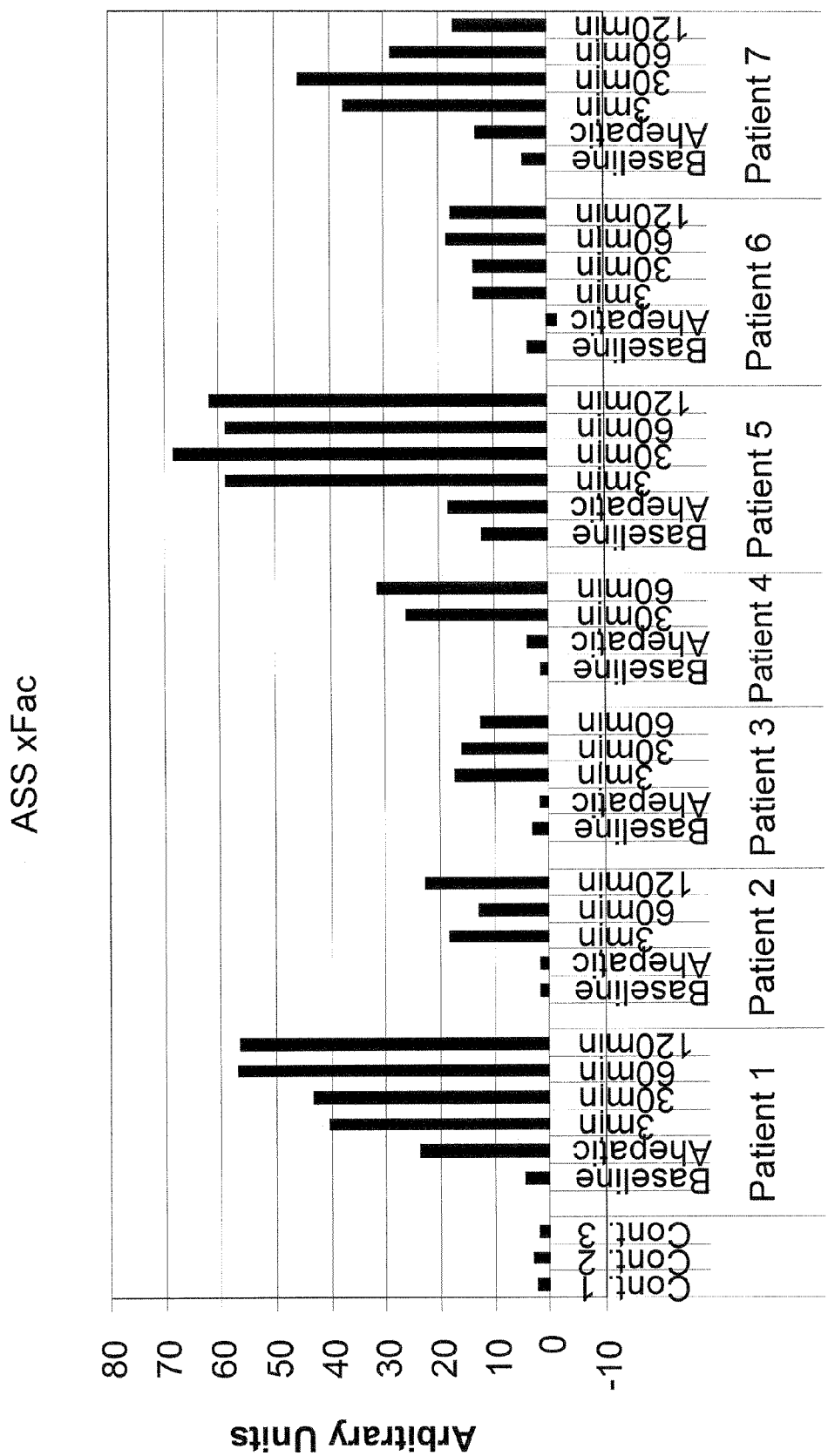
FIG. 25 is a graph showing ASS detection in patients.
Figure 26:
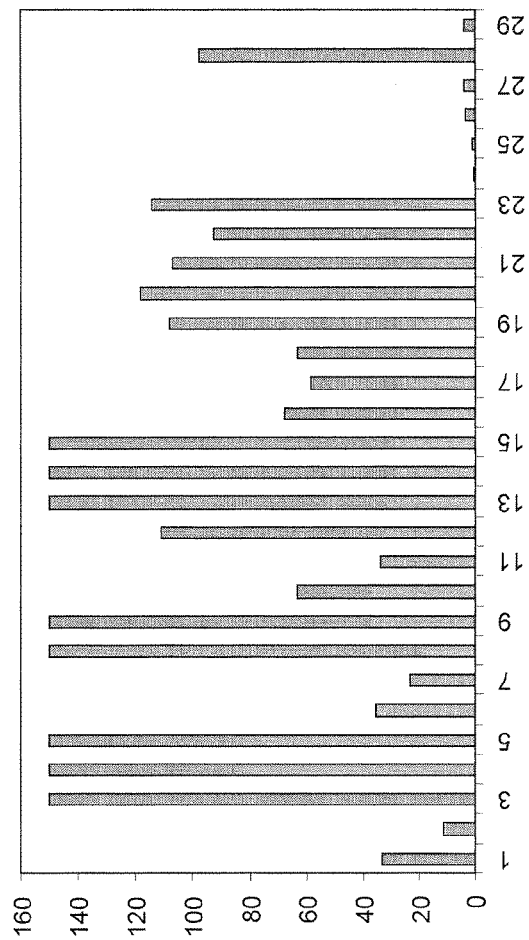
FIG. 26 is a graph showing results from a sandwich ELISA. ASS samples from UF (patient 1-4). Capture antibody: ASS-rabbit 1000 ng/well; ASS protein: 100 ng/1st well; Serum sample: 100 µl; Detection Ab: 1:500 (BD-mouse).
Figure 27:
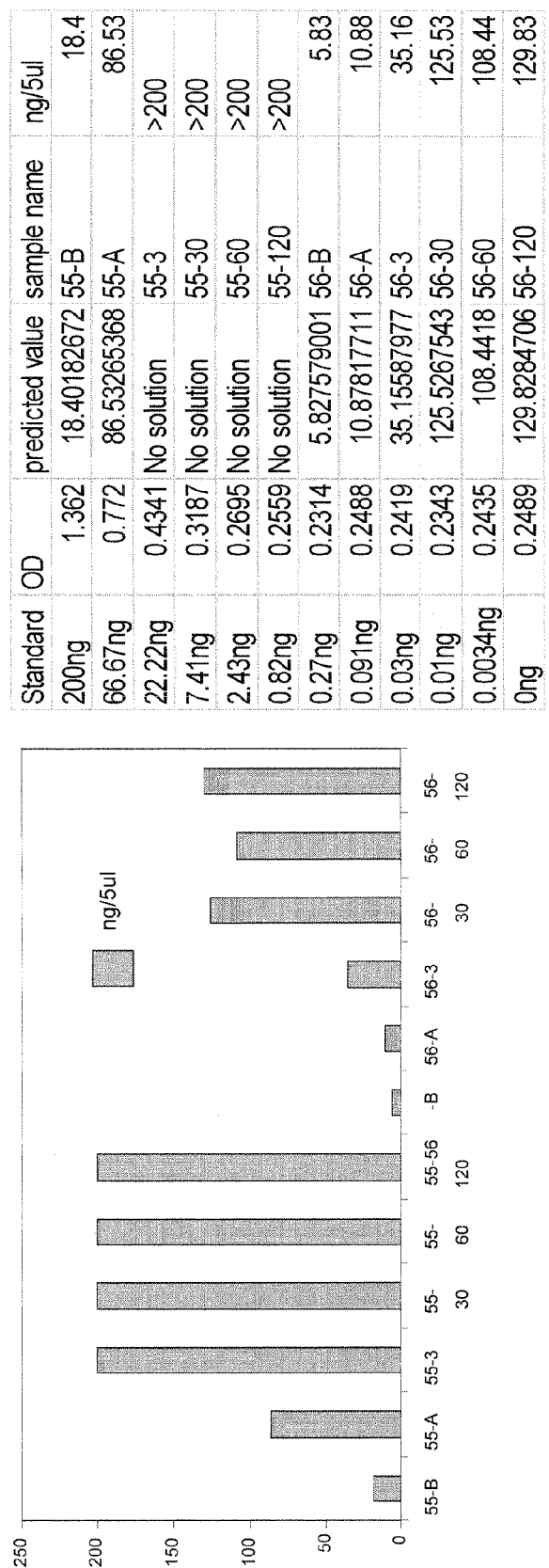
FIG. 27 is a graph showing the results of a sandwich ELISA (SW-ELISA) with ASS serum sample (patient 5-6).
Figure 28:
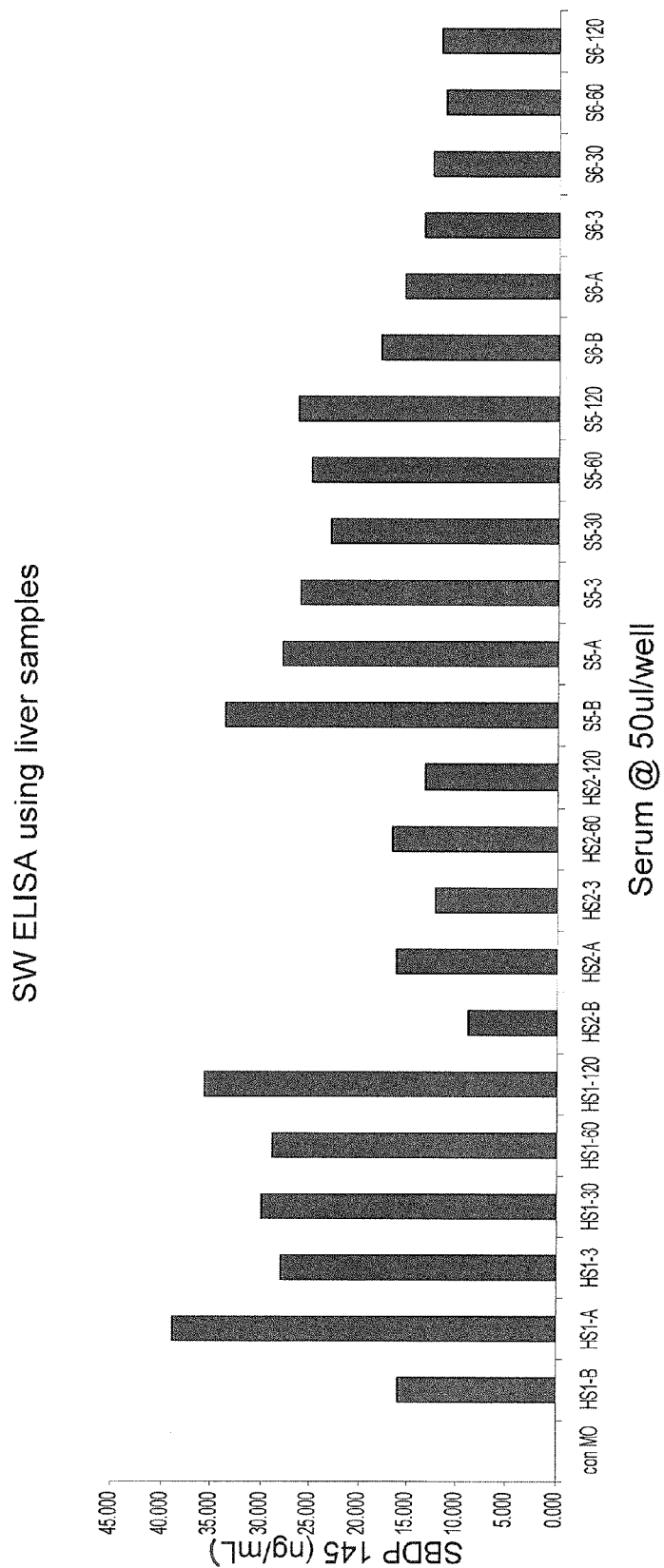
FIG. 28 is a graph showing results of detection of SDBP from a sandwich ELISA using liver samples.

As seen in FIG. 3C, a major band of γ-GTP in the liver (~140 kDa) is different from a predicted M.W. of 90 kDa, and appears to be modified in I/R liver similarly to caspase-3 treated livers with additional accumulation of ~70 kDa minor immunoreactivity. Preliminary validation of diagnostic values of novel hepatic biomarkers was performed in blood plasma.

It has been found that intact ASS protein (46 kDa) accumulated in plasma of rats subjected to 30/30 min ischemia/reperfusion, but it was absent in plasma from normal or sham-operated rats and in rats with chronic alcoholic administration. Surprisingly, there were no ASS cleavage fragments in I/R plasma contrary to what was observed in liver tissue at this time point (FIG. 3 B). Very low levels of GST-BB, hepatic isoform of GST, were detectable in normal rat plasma as ~51 kDa protein (predicted M.W.—23-25 kDa). GST-BB was disappeared in sham and I/R rats, while there was a significant increase in GST-BB in rats chronically treated with alcohol. Plasma ALT levels (57 kDa predicted. M.W) were unchanged in I/R and sham rats. In contrast, ALT in chronic alcohol rat plasma was increased together with a slight shift of immunoreactive bands and appearance of fragments, which may indicate ALT cleavage.

Example 5

Proteomic Analysis

Proteomic analysis is applied to the rat I/R liver. Proteins are resolved by biphasic ion-exchange chromatography on a consecutive S- and Q-sepharose columns in tandem with gel electrophoresis (CAX-PAGE). Differential display of proteins are accomplished by Coomassie Blue visible staining, all performed in tandem on the same gels. Proteins with differential expression or modifications are identified using HT analyzer 1D software (Nonlinear Dynamics) and extracted for in-gel trypsin digestion. Digests are analyzed using nanospray liquid chromatography online with tandem mass spectrometry (nano-LC/MSMS). Resulting tandem mass spectra are correlated with tryptic peptide sequences extracted from a non-redundant mammalian protein database utilizing the Sequest algorithm. Several possible homologous proteins are usually generated using this approach. The molecular mass of protein band on SDS-PAGE gel is compared with the predicted molecular masses for sequenced proteins found in databases.

TABLE 1

Biomarkers of liver ischemia/reperfusion injury.

| Liver Biomarker | Molecular mass | Cleavage fragments in I/R liver | Change rate in I/R liver vs sham | Detection method |
|---|---|---|---|---|
| Argininosuccinate synthetase (AS) | 46 kDa | 34 kDa, 31 kDa and 24 kDa breakdown products by caspase-3 | 31 and 34 kDa expressed in I/R livers; 24 kDa is increased >> 10-fold | HTS-WB, Western blot, |
| Squalene synthase (SQS) | 48 kDa | 36 kDa, cleaved via unknown mechanism | Appeared as 36 kDa in I/R liver | HTS-WB. |
| Liver glycogen phosphorylase (GP) | 97 kDa | Cleaved; breakdown products are not determined | 97 kDa band substantially reduced in I/R liver | LC/MS followed by sequencing. |
| Sulfotransferase (ST) | 31 kDa | Cleaved; fragments are not determined | 31 kDa nearly disappeared in I/R liver | LC/MS followed by sequencing. |

Samples were also run as tandem for sham-operated liver samples (C) and I/R samples (T). Proteins with differential expression were identified using HT analyzer 1D software (Nonlinear Dynamics) and squared. Protein bands were excised from gel (C band and T hand if present), and digested with trypsin. Digests were analyzed using nano-spray liquid chromatography online with tandem mass spectrometry (nano-LC/MSMS). Resulting tandem mass spectra were correlated with tryptic peptide sequences extracted from a non-redundant mammalian protein database utilizing the Sequest algorithm. Peptide matches only of high spectral correlation were collected by use of DTASelect software data filtering, and IR vs sham liver proteomes were compared using Contrast software. Identification and analysis of most relevant hepatic proteins performed so far is presented below. These proteins were either decreased significantly (e.g. T7A vs. C7A) or disappeared completely (e.g. T4 vs. C4) in I/R liver tissue compared to sham-operated livers.

Example 6

Liver Transplant Patients

Figure 29:
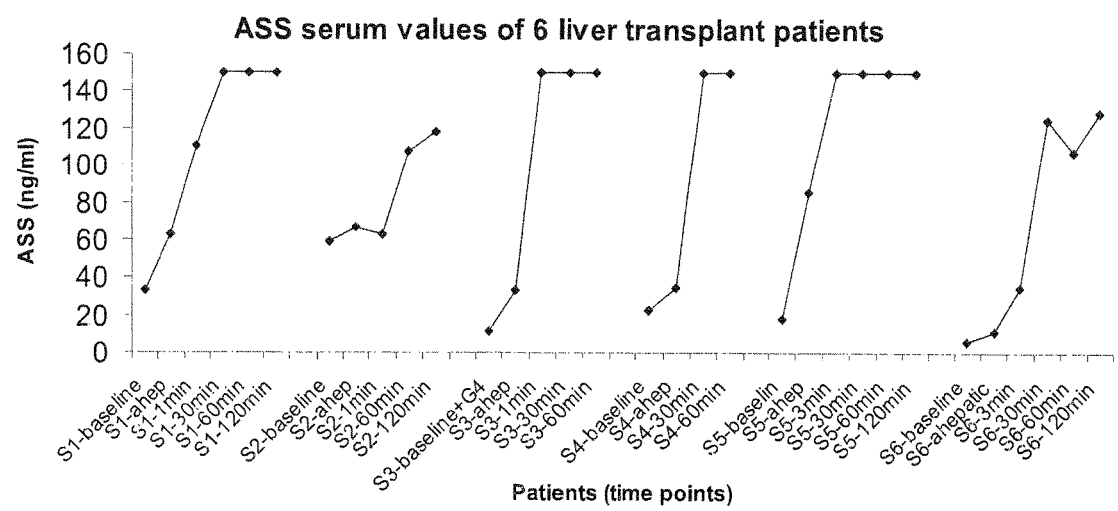
FIG. 29 is a graph showing ASS serum values from six liver transplant patients. Serum samples were collected from liver transplant patients (n=6) before the transplant occurred (baseline), while the liver was removed (ahepatic) and at various time points after the new liver was inserted into the patients (1 or 3 min, 30 min, 45 min, 60 min, 120 min). Serum ASS levels were measured by ASS specific SW ELISA (in ng/ml). Values of 150 ng/ml exceeded the sensitivity of the assay.

FIG. 29 shows ASS serum values from six liver transplant patients. Serum samples were collected from liver transplant patients (n=6) before the transplant occurred (baseline), while the liver was removed (ahepatic) and at various time points after the new liver was inserted into the patients (1 or 3 min, 30 min, 45 min, 60 min, 120 min). Serum ASS levels were measured by ASS specific SW ELISA (in ng/ml). Values of 150 ng/ml exceeded the sensitivity of the assay.

TABLE 2

Hepatic proteins identified by nano-spray liquid chromatography with tandem mass spectrometry (nano-LC/MSMS), which are decreased or disappeared in I/R liver tissue vs sham operated liver after differential display on SDS-PAGE.

| Band | GI | Protein Name | Predicted Mass | Observed Mass | C pep | C % | T pep | T % |
|---|---|---|---|---|---|---|---|---|
| 4 | Gi:6978809 | enolase 1, alpha. [Rattus norvegicus] | 47.5 | 47 | 4 | 11 | | |
| 6A | Gi:1560087 | liver glycogen phosphorylase [Rattus norvegicus]. | 97.9 | 99 | 2 | 2.1 | | |
| 7A | Gi:11560087 | liver glycogen phosphorylase [Rattus norvegicus]. | 97.9 | 99 | 8 | 17.5 | 2 | 4.8 |
| 10 | Gi:6981594 | Estrogen sulfotransferase [Rattus norvegicus] | 35.4 | 35 | 2 | 7.1 | | |
| 12 | Gi:8393186 | carbamoyl-phosphate synthetase 1; [;Rattus norvegicus] | 164.6 | 120 | 2 | 1.5 | | |
| 13 | Gi:8393186 | carbamoyl-phosphate synthetase 1; [Rattus norvegicus] | 164.6 | 120 | 3 | 2.3 | | |
| 14A | Gi:8392839 | ATP citrate lyase [Rattus norvegicus] | 121.5 | 120 | 2 | 2.8 | | |
| | Gi:8393186 | carbamoyl-phosphate synthetase 1; [Rattus norvegicus] | 164.6 | 120 | 5 | 4.1 | | |
| 14C | Gi:8393322 | glucose regulated protein, 58 kDa [Rattus norvegicus] | 51 | 56 | 6 | 13.1 | | |

Example 7

ASS and ALT as Biomarkers of Chlorinated Hydrocarbon Liver Injury

Figures 30A, 30B:
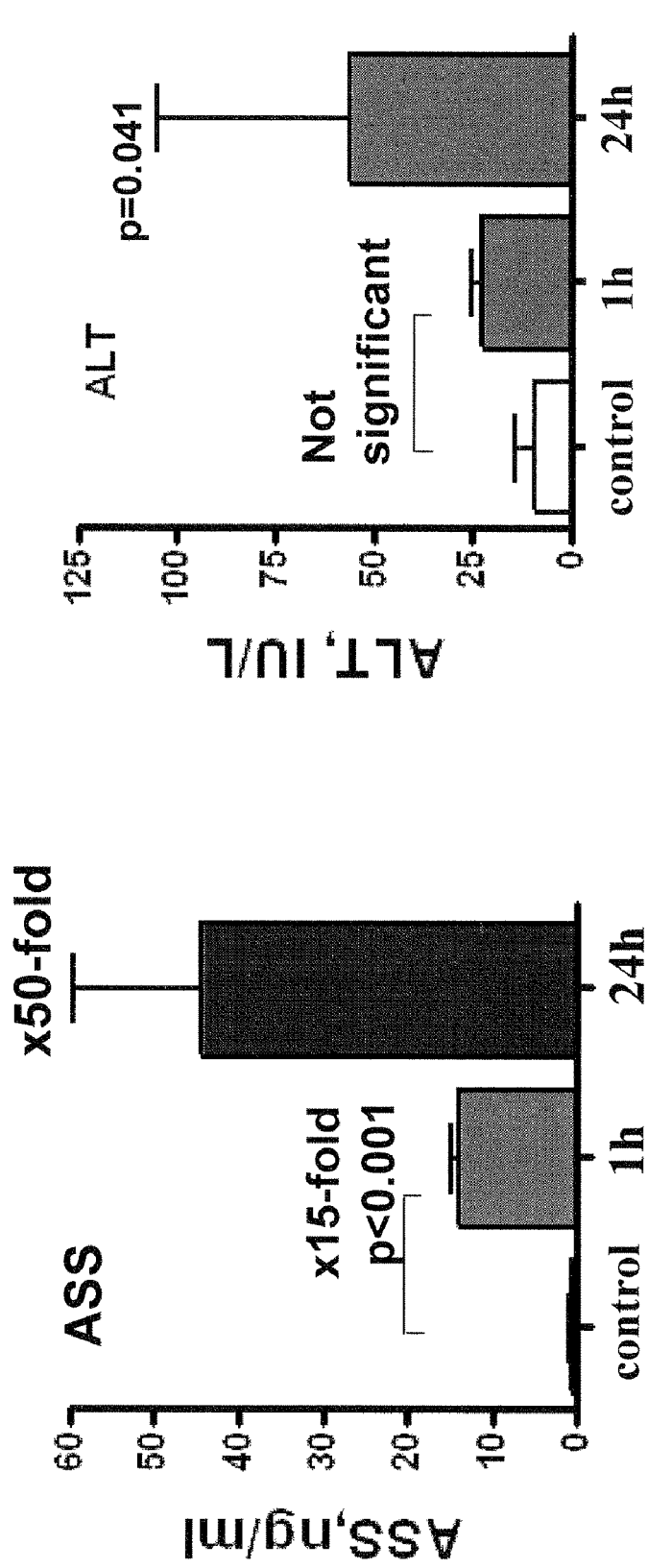
FIG. 30A shows plasma ASS accumulation after injection of carbon tetrachloride in a rat model. The increase 1 hr after injection was 15 times that of a control and after 50 times greater than the control 24 hr post injection.
FIG. 30B shows plasma ALT accumulation in the rat model corresponding to the model in FIG. 30B compared to plasma levels in the control. The increase 1 hr after injection was not significant; after 24 hr the increase over control values showed a significance of p=0.041.

Rats (n=6) were injected with 0.5 ml/kg of carbon tetrachloride ($CCL_4$) in vegetable oil. Plasma arginosuccinate synthetase (ASS) and alanine transaminase (ALT) accumulation was measured 1 hr and 24 hr after injection. ASS increased over 15-fold compared to controls after 1 hr and over 50-fold compared to controls after 24 hr (p<0.0001), as shown in FIG. 30A. ALT did not increase significantly after 1 hr but showed a significant increase (p=0.041) 24 hr after injection as shown in FIG. 30B.

Example 8

ASS, CPS-1 and SULTA1 as Biomarkers of Ecstasy Liver Injury

Figures 31A, 31B:
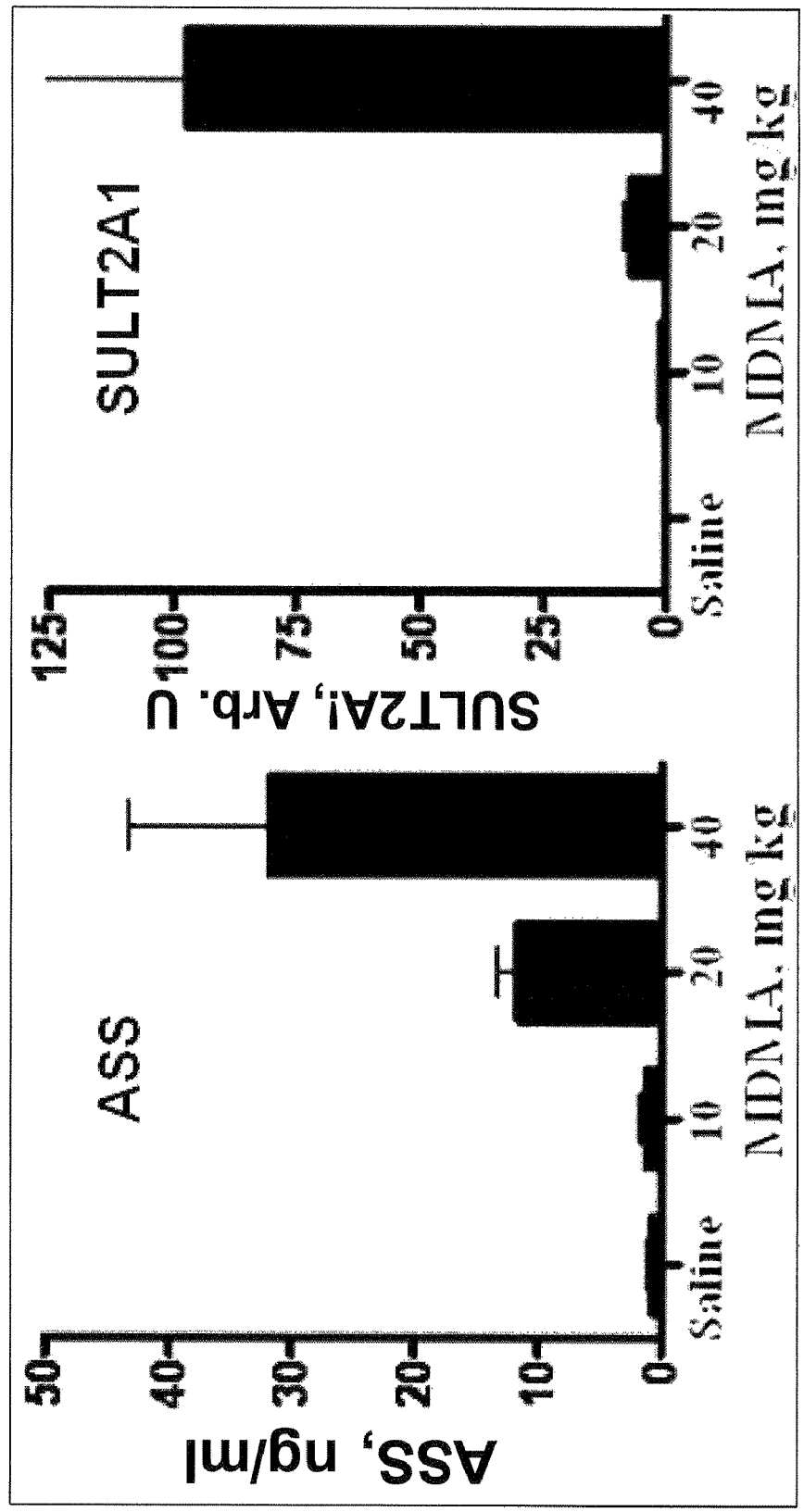
FIG. 31A shows an increase in serum ASS after repeated i.p. injection of Ecstasy (MDMA) after injection of a total of 40 mg/kg.
FIG. 31B shown an increase in serum SULT2A1 after repeated i.p. injection of MDMA after injection of a total of 40 mg/kg.
Figure 32:
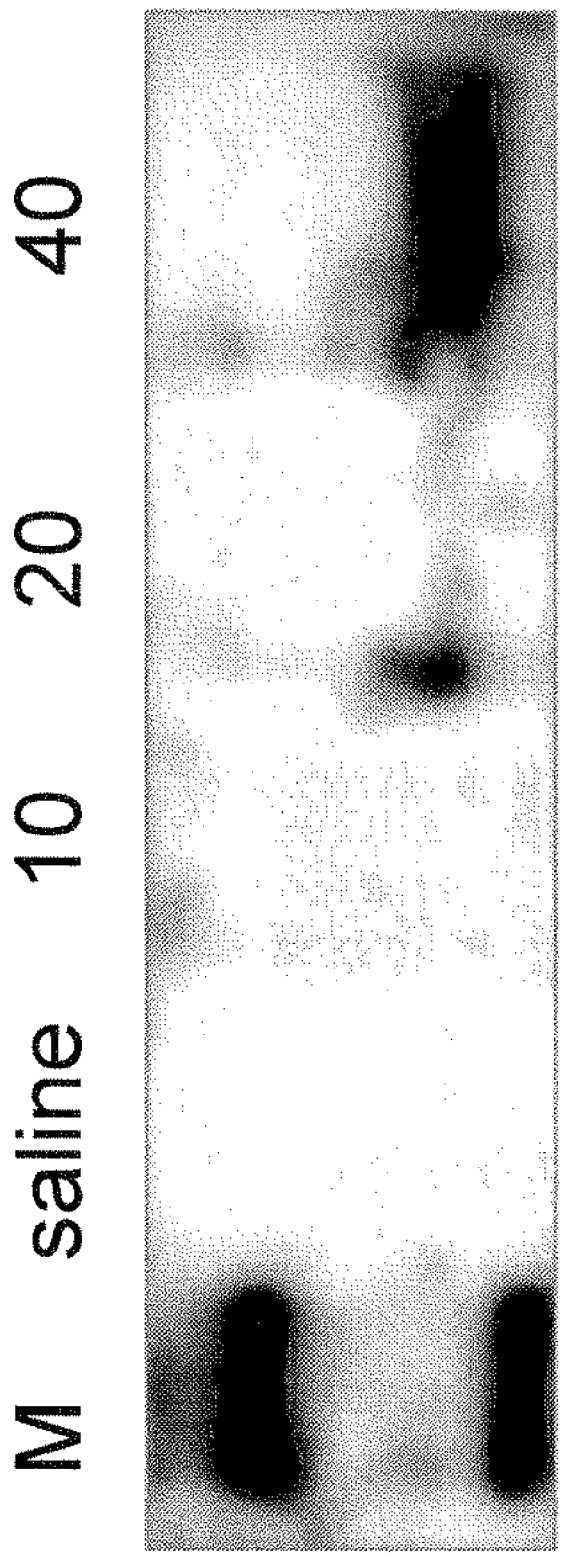
FIG. 32 shows increased levels of serum carhamoylphosphate synthase-1 (CPS-1) after repeated i.p. injection of a total 40 mg/kg MDMA.

Serum arginosuccinate synthetase (ASS), carbamoylphosphate synthase-1 (CPS-1) and sulfur transferase isoform A1 (SULT2A1) levels were measured after repeated injections of 10 mg/kg of methylenedioxyacetamine (MDMA) at 1.5 hr intervals. A significant increase in ASS compared to control serum levels in rats was observed after i.p. injection of 20 mg/kg (p<0.01), after a total of 40 mg/kg (p<0.001), and in SULT2A1 after a total of 20 mg/kg (p<0.001) and 40 mg/kg (p<0.0001), FIG. 31A and FIG. 31B. No increase was observed in alanine transferase (ALT). Rats were sacrificed 24 hr after the last ecstasy injection and CPS-1 was detected by PAGE on 4-12% gels (4 injections of MDMA (10 mg/kg administered 1.5 hr apart). FIG. 32 shows no detectable MDMA in the saline control.

Example 9

Biomarkers of Bacterial Endotoxin Liver Injury

Figure 33A:
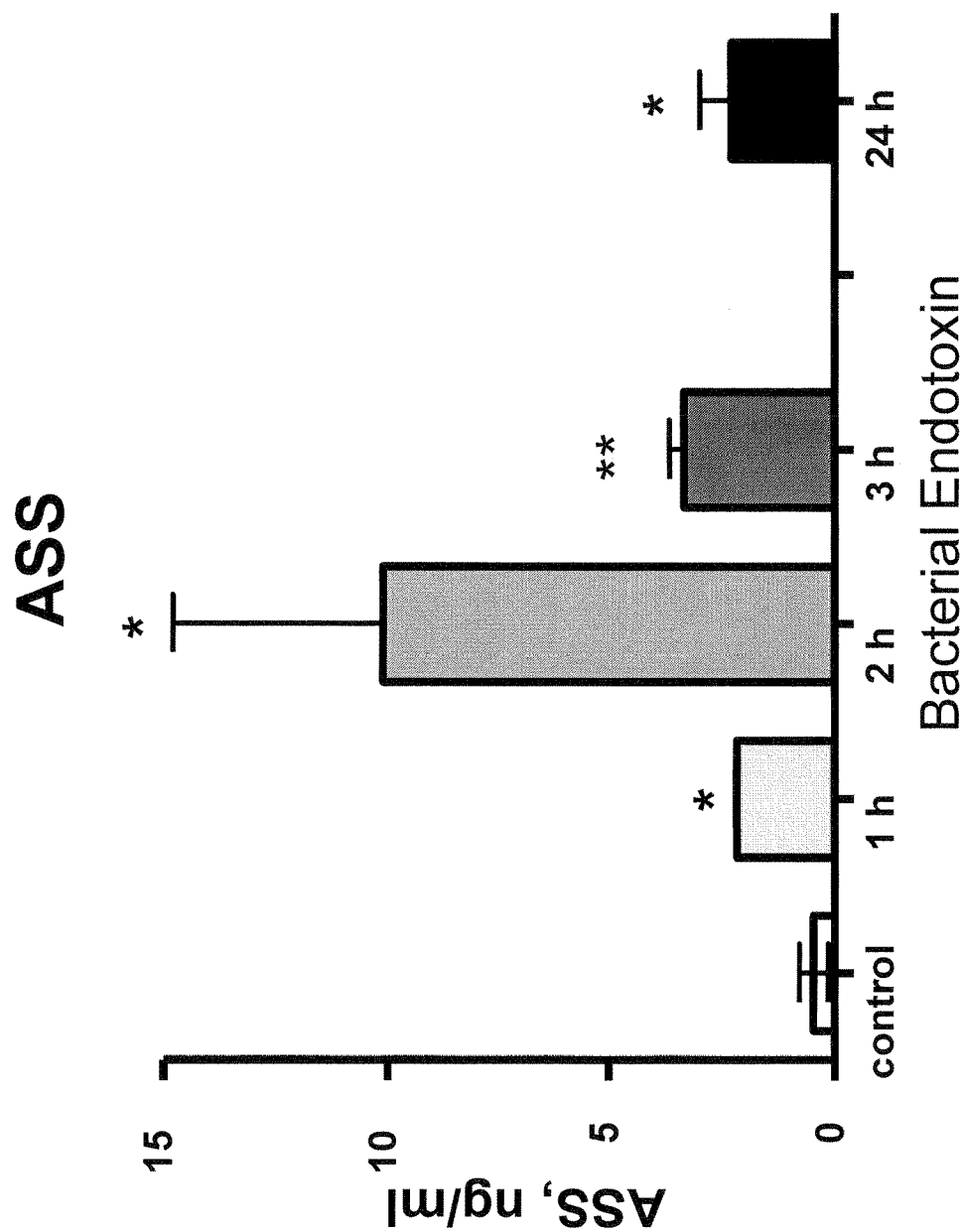
FIG. 33A shows bacterial hepatotoxicity indicated by ASS accumulation in serum after i.p. injection of 100 ug/kg bacterial endotoxin. A significant increase over controls is shown after 1 hr and at least up to 24 hr after injection.
Figures 33B, 33C:
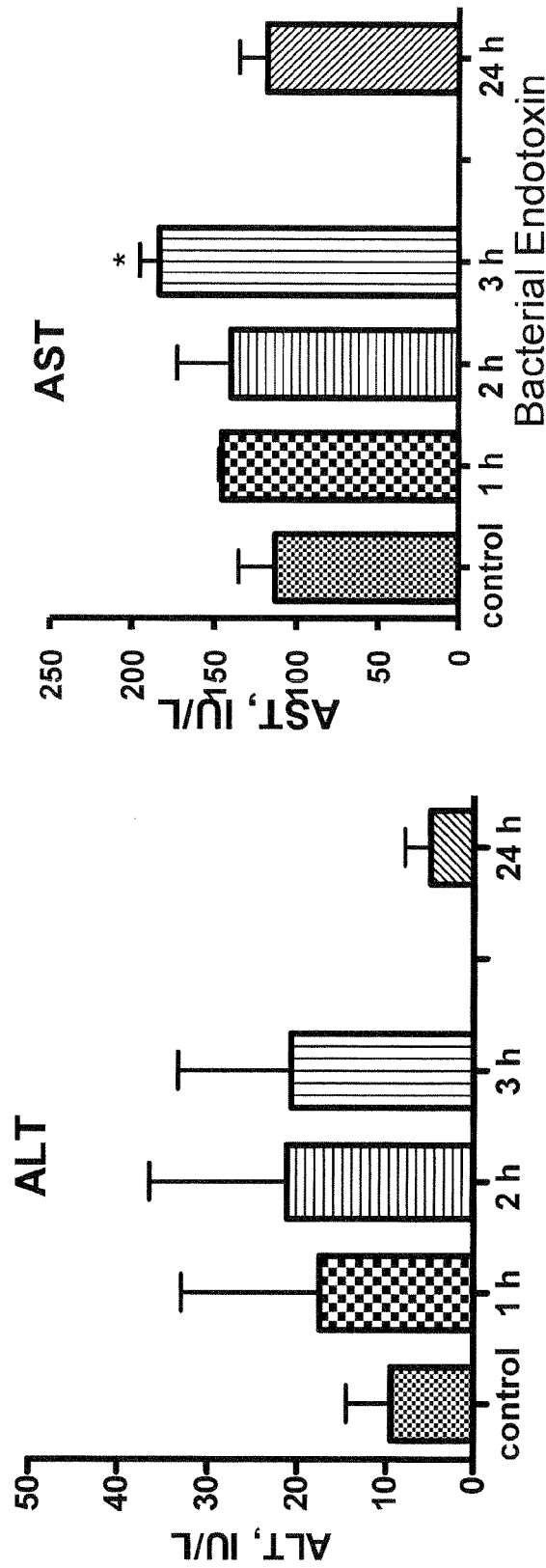
FIG. 33B shows no significant increase in serum AST 24 hr after i.p injection of 100 ug/kg bacterial endotoxin.
FIG. 33C shows no significant increase in serum ALT 24 hr after i.p. injection of 100 ug/kg bacterial endotoxin.

Rats were injected with 100 ug/kg of bacterial endotoxin (E-LPS). Serum arginosuccinate synthetase (ASS) significantly increased after 1 hr and remained increased compared to controls at least up to 24 hr after injection, see FIG. 33A. There was no significant increase in ALT or aspartate transaminase (AST) even 24 hr post injection, see FIG. 33B and FIG. 33C.

Figure 34B:
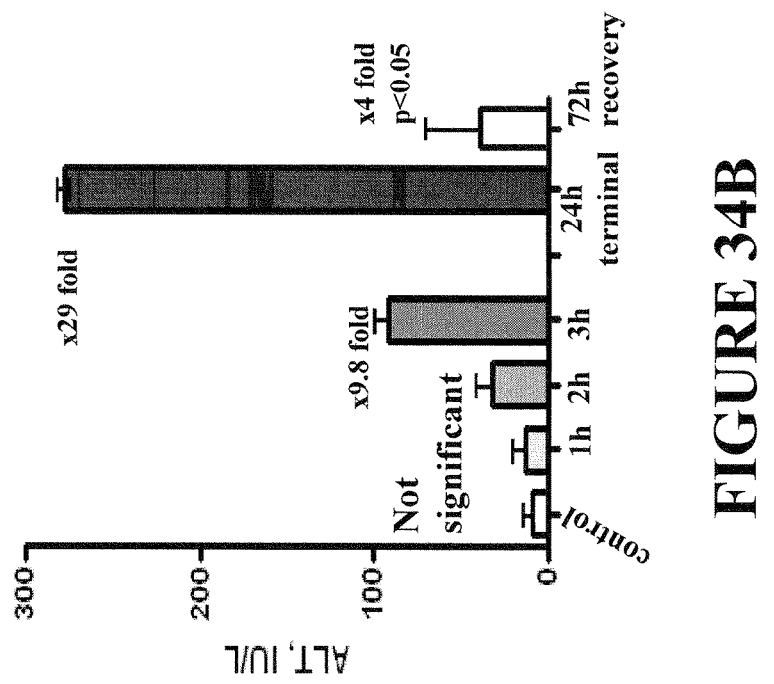
FIG. 34B shows the effect of combined bacterial and chemical hepatotoxicity on serum levels of ALT and after i.p. injection of LPS and D-galactosamine and recovery of ALT levels 72 hrs post injection.
Figure 34A:
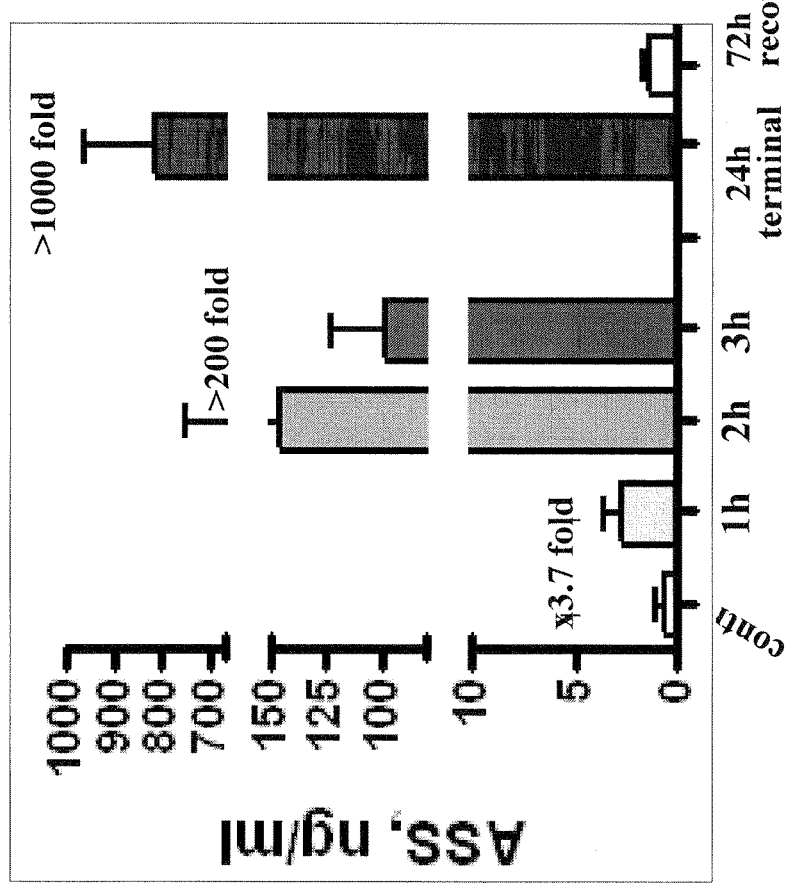
FIG. 34A shows the effect of combined bacterial and chemical hepatotoxicity on serum levels of ASS and after i.p. injection of LPS and D-galactosamine and recovery of ASS levels 72 hrs post injection.

When the rats were injected with E-LPS and D-galactosamine, 10 ug/kg and 500 mg/kg respectively, ASS levels increased dramatically by 24 hr, showing an increased serum level of >3.7 fold after 1 hr, >200 fold after 3 hr and >1000 fold after 24 hr. ALT levels also increased, peaking at >29-fold at 24 hr. Both ASS recovered to baseline or control levels after 24 hr while ALT decreased to about 4-fold over controls after 72 hr. The levels of ASS and ALT up to 72 hr are shown in FIG. 34A and FIG. 34B.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

---

We claim:

1. A method for detecting physical liver damage in a subject, comprising:
    detecting the presence of arginosuccinate synthetase (ASS), and at least one of sulfotransferase 2A1 (SULT2A1) and carbamoylphosphate synthase-1 (CPS-1) in a biological sample of a subject suspected of having been exposed to at least one hepatotoxic substance wherein an increased amount of ASS one hour after exposure and an increased amount of at least one of SULT2A1 or CPS-1 after up to about 24 hours of exposure compared to a normal subject not exposed to at least one hepatotoxic substance is indicative of physical liver damage.

2. The method of claim 1 wherein the hepatotoxic substance is a chlorinated hydrocarbon.

3. The method of claim 2 wherein the chlorinated hydrocarbon is carbon tetrachloride.

4. The method of claim 1 wherein the hepatotoxic substance is D-galactosamine.

5. The method of claim 1 wherein the hepatotoxic substance is a bacterial endotoxin and D-galactosamine.

6. The method of claim 5 wherein the bacterial endotoxin is LPS.

7. The method of claim 1 wherein the biological sample is liver tissue, blood, serum, plasma, liver cells, urine, tears or saliva.

8. The method of claim 1 wherein the at least one hepatotoxic substance is the combination of D-galactosamine and bacterial endotoxin LPS.

9. The method of claim 8 wherein ASS plasma levels about 72 hours after exposure of a subject suspected of having liver damage to bacterial LPS and D-glucosamine are comparable to ASS plasma levels in a normal subject.

10. The method of claim 1 wherein the hepatotoxic substance is Methylenedioxymethamphetamine (MDMA).

11. The method of claim 10 wherein the MDMA exposure is about 40 mg/kg.

12. The method of claim 11 wherein CPS-1 and SULT2A1 plasma levels are increased compared to levels in normal subjects not exposed to up to 40 mg/kg MDMA.

13. The method of claim 1 further comprising detecting for the presence of alanine transaminase (ALT) in the biological sample.

14. A process for detecting physical liver damage in a subject, comprising:
    collecting a sample of a bodily fluid or a tissue in contact with liver tissue from a subject suspected of having been exposed to at least one hepatotoxic substance or a bacterial endotoxin; and
    analyzing said sample or a fraction thereof for an amount of sulfotransferase 2A1(SULT2A1); and
    optionally analyzing said sample or a fraction thereof for at least one additional protein biomarker associated with physical liver damage; and correlating the presence or amount of the detected protein biomarkers with the presence or type of physical liver damage in the subject;
    wherein an increased amount of SULT2A1 levels compared to a normal subject not exposed to at least one hepatotoxic substance is indicative of physical liver damage.

15. The process of claim 14 wherein said optional additional protein biomarker is selected from the group consisting of arginosuccinate synthetase (ASS), alanine transaminase (ALT), carbamoylphosphate synthase-1 (CPS-1) or combinations thereof.

16. The process of claim 14 wherein the optional additional protein biomarker is ASS and an increased amount of ASS one hour after exposure and an increased amount of SULT2A1 or an additional protein biomarker selected from the group of CPS-1 and ALT after up to about 24 hr of exposure compared to a normal subject not exposed to at least one hepatotoxic substance is indicative of physical liver damage.

17. The process of claim 14 wherein the biological sample is liver tissue, blood, serum or plasma.

18. A kit using the method of claim 14, the kit comprising:
    (a) a substrate for holding a biological sample isolated from a human subject,
    (b) an agent that specifically interacts with SULT2A1;
    (c) an optional additional agent that specifically interacts with at least one additional protein biomarker upon contact with said sample; and
    (d) printed instructions for reacting the agent and the optional additional agent with the sample or a portion of the sample to detect the presence or amount of the biomarker for diagnosing a damaged nerve cell in the subject;
    wherein said optional additional protein biomarker is selected from the group consisting of arginosuccinate synthetase (ASS), alanine transaminase (ALT), carbamoylphosphate synthase-1 (CPS-1) or combinations thereof.

19. The kit of claim 18, wherein the agent is an antibody that specifically and independently binds to its respective enzyme biomarker.

* * * * *

UNITED STATES PATENT AND TRADEMARK OFFICE
CERTIFICATE OF CORRECTION

PATENT NO.         : 8,048,638 B2
APPLICATION NO.    : 12/685822
DATED              : November 1, 2011
INVENTOR(S)        : Stanislav Svetlov et al.

It is certified that error appears in the above-identified patent and that said Letters Patent is hereby corrected as shown below:

Column 2,
Line 24, "a-enolase 1" should read --α-enolase 1--.
Lines 33-34, "a-enolase 1" should read --α-enolase 1--.
Line 45, "a-enolase 1" should read --α-enolase 1--.
Lines 53-54, "a-enolase 1" should read --α-enolase 1--.

Column 3,
Line 48, "a-enolase 1" should read --α-enolase 1--.
Line 58, "chlorofoim" should read --chloroform--.

Column 4,
Line 28, "a-spectrin" should read --α-spectrin--.
Line 30, "γGTP." should read --γ-GTP.--.
Line 38, "liver injury. Liver injuries" should read
    --liver injury and a predicted molecular weight of 46 kDa. Liver injuries--.
Line 42, "(normnal rats)" should read --(normal rats)--.
Line 50, "methods. Liver" should read
    --methods and a predicted molecular weight of 23-25 kDa. Liver--.
Line 57, "methods. Liver" should read
    --methods and a predicted molecular weight of 90 kDa. Liver--.
Line 64, "methods. Liver" should read
    --methods and a predicted molecular weight of 57 kDa. Liver--.

Column 5,
Line 38, "Mab." should read --MAb.--.

Column 6,
Line 8, "γGTP" should read --γ-GTP--.
Line 57, "in a384" should read --in a 384--.

Signed and Sealed this
Third Day of April, 2012

David J. Kappos
*Director of the United States Patent and Trademark Office*

Column 7,
Lines 31-32, "carhamoylphosphate" should read --carbamoylphosphate--.
Line 38, "AST 24 hr" should read --ALT 24 hr--.
Line 40, "ALT 24 hr" should read --AST 24 hr--.

Column 8,
Line 10, "The tell" should read --The term--.

Column 9,
Line 27, "about 80%," should read --about 180%,--.
Line 47, "in absolute amount" should read --an absolute amount--.
Line 52, "in absolute amount" should read --an absolute amount--.
Line 59, "in absolute amount" should read --an absolute amount--.

Column 12,
Line 7, "thereof. may" should read --thereof, may--.

Column 14,
Line 2, "but not" should read --but are not--.
Line 4, "sullotransferase" should read --sulfotransferase--.
Line 19, "of any" should read --of many--.
Line 62, "Paraminosalicylic" should read --Paraaminosalicylic--.

Column 15,
Line 5, "Disulfuram" should read --Disulfiram--.
Line 6, "Paraminobenzoic" should read --Paraaminobenzoic--.
Lines 8-9, "Phenyloin, Paramino" should read --Phenytoin, Paraamino--.

Column 17,
Line 9, "a-enolase 1" should read --α-enolase 1--.

Column 18,
Line 20, "a-enolase 1" should read --α-enolase 1--.
Lines 53-54, "a-enolase 1" should read --α-enolase 1--.

Column 19,
Line 65, "a-enolase 1" should read --α-enolase 1--.

Column 22,
Line 34, "may be hound" should read --may be bound--.

Column 24,
Line 53, "will hind" should read --will bind--.

CERTIFICATE OF CORRECTION (continued)
U.S. Pat. No. 8,048,638 B2

Column 29,
Line 42, "Stiles & Ten" should read -- Stites & Terr--.

Column 31,
Line 59, "a-enolase 1" should read --α-enolase 1--.

Column 32,
Line 1, "a-enolase 1" should read --α-enolase 1--.
Line 9, "a-enolase l" should read --α-enolase 1--.
Line 19, "iscome" should read --become--.
Line 39, "incisions is" should read --incision is--.
Line 55, "from FR," should read --from I/R,--.

Column 35,
Line 7, "₇-GTP" should read --γ-GTP--.

Column 36,
Lines 57-58, "N-2,4-AKAPNTPDILEIEFKK-229-C" should read
           --N-214-AKAPNTPDILEIEFKK-229-C--.

Column 38,
Line 11, "a Thspectrin" should read --αII-spectrin--.

Column 39,
Line 25, "T hand" should read --T band--.

Column 40,
Line 46, "Gi: 1560087" should read --Gi: 11560087--.
Line 63, "51" should read --57--.